(12) United States Patent
Chen et al.

(10) Patent No.: US 11,813,317 B2
(45) Date of Patent: Nov. 14, 2023

(54) METHOD FOR PREVENTING OR TREATING METABOLIC DISORDER

(71) Applicants: Academia Sinica, Taipei (TW); National Yang Ming Chiao Tung University, Taipei (TW)

(72) Inventors: Ruey-Hwa Chen, Taipei (TW); Yu-Hsuan Chen, Taipei (TW); Tzu-Yu Huang, Taipei (TW); Wen-Hsin Li, Taipei (TW); Ting-Fen Tsai, Taipei (TW); Zhao-Qing Shen, Taipei (TW)

(73) Assignees: Academia Sinica, Taipei (TW); National Yang Ming Chiao Tung University, Taipei (TW)

( * ) Notice: Subject to any disclaimer, the term of this patent is extended or adjusted under 35 U.S.C. 154(b) by 33 days.

(21) Appl. No.: 17/540,289

(22) Filed: Dec. 2, 2021

(65) Prior Publication Data
US 2022/0175895 A1    Jun. 9, 2022

Related U.S. Application Data

(60) Provisional application No. 63/121,306, filed on Dec. 4, 2020.

(51) Int. Cl.
*A61P 3/00* (2006.01)
*C12N 15/86* (2006.01)
*A61K 38/48* (2006.01)
*A61P 3/04* (2006.01)
*A61K 45/06* (2006.01)
*C12N 9/48* (2006.01)

(52) U.S. Cl.
CPC .......... *A61K 38/4813* (2013.01); *A61K 45/06* (2013.01); *A61P 3/04* (2018.01); *C12N 9/485* (2013.01); *C12N 15/86* (2013.01); *C12Y 304/19012* (2013.01); *C12N 2750/14111* (2013.01)

(58) Field of Classification Search
CPC .................................. A61P 3/00; C12N 15/86
See application file for complete search history.

(56) References Cited

U.S. PATENT DOCUMENTS

2020/0263159 A1* 8/2020 Colecraft et al. .... C12N 9/6472

\* cited by examiner

*Primary Examiner* — James D Schultz
*Assistant Examiner* — James Joseph Graber
(74) *Attorney, Agent, or Firm* — AMIN, TUROCY & WATSON, LLP

(57) ABSTRACT

Provided is a method for preventing or treating a metabolic disorder, including administering to a subject a therapeutically effective amount of TRABID protein or a functionally related variant thereof, or a nucleic acid encoding TRABID protein or a functionally related variant thereof. Also provided is a method for reducing fat accumulation through TRABID-induced deubiquitination to promote autophagy activity and lipid metabolism.

16 Claims, 69 Drawing Sheets
(27 of 69 Drawing Sheet(s) Filed in Color)
Specification includes a Sequence Listing.

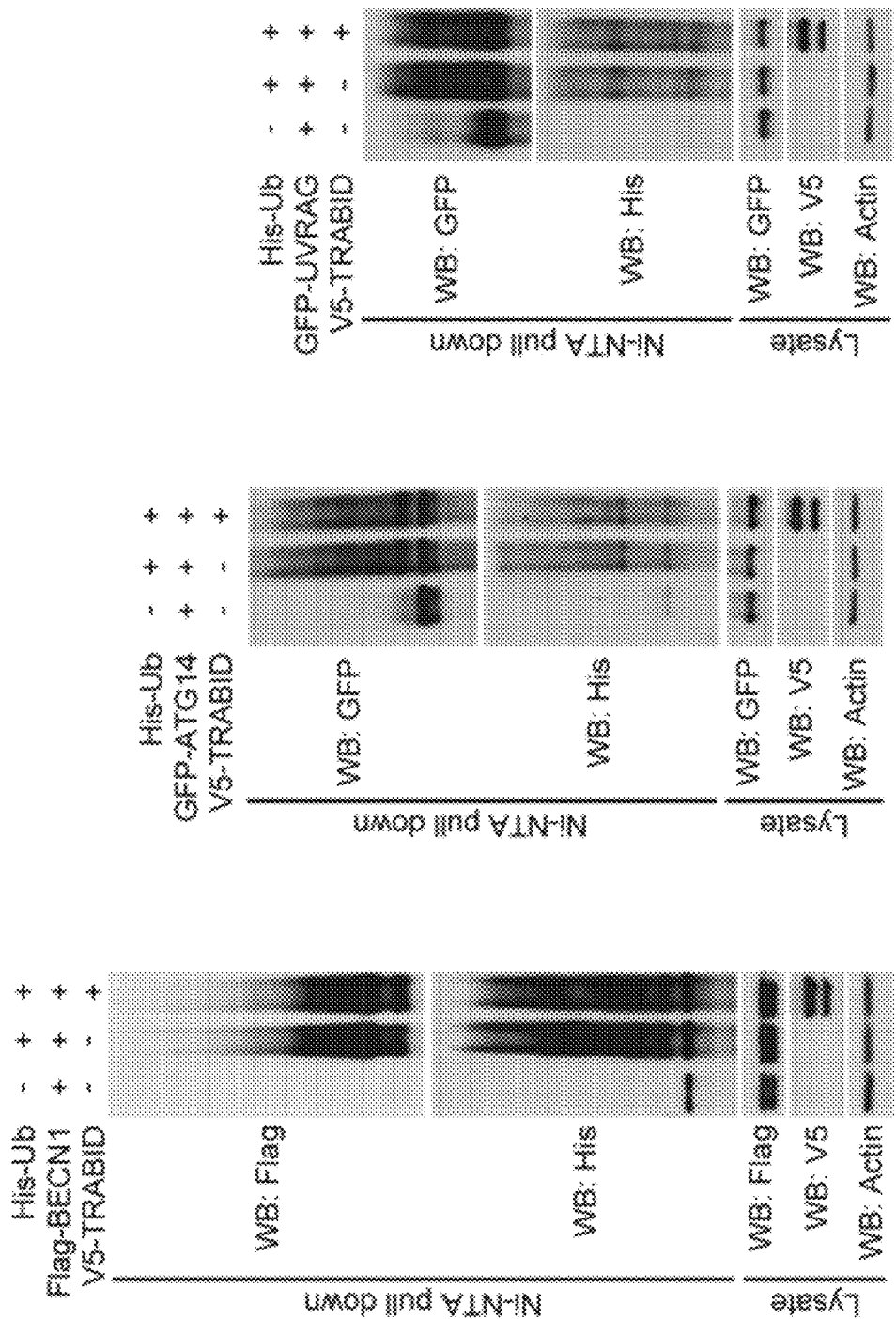

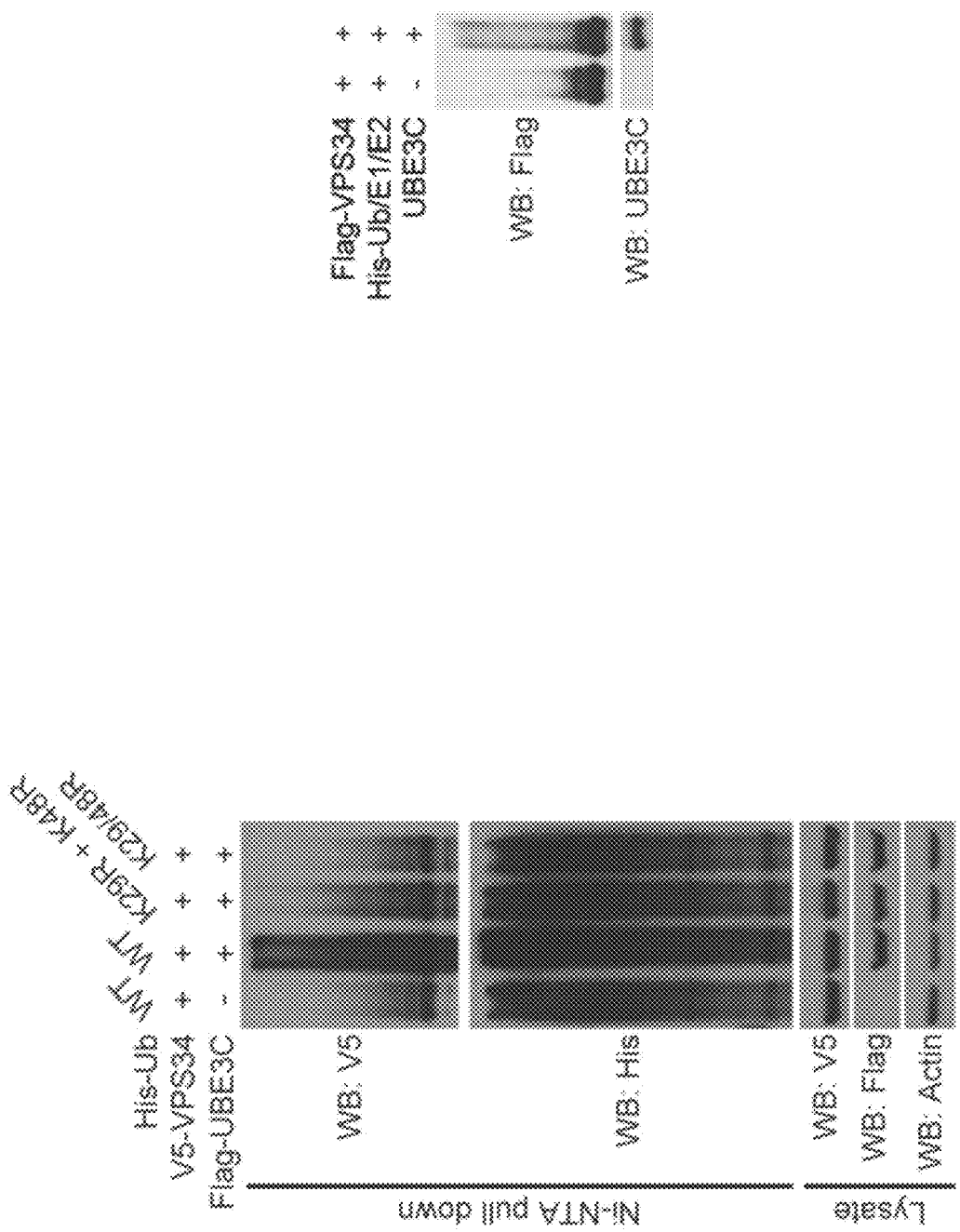

SEQUENCE LISTING

```
<160> NUMBER OF SEQ ID NOS: 13

<210> SEQ ID NO 1
<211> LENGTH: 708
<212> TYPE: PRT
<213> ORGANISM: Homo sapiens

<400> SEQUENCE: 1

Met Ser Glu Arg Gly Ile Lys Trp Ala Cys Glu Tyr Cys Thr Tyr Glu
1               5                   10                  15

Asn Trp Pro Ser Ala Ile Lys Cys Thr Met Cys Arg Ala Gln Arg Pro
```

```
                20                  25                  30
Ser Gly Thr Ile Ile Thr Glu Asp Pro Phe Lys Ser Gly Ser Ser Asp
            35                  40                  45

Val Gly Arg Asp Trp Asp Pro Ser Ser Thr Glu Gly Gly Ser Ser Pro
50                  55                  60

Leu Ile Cys Pro Asp Ser Ser Ala Arg Pro Arg Val Lys Ser Ser Tyr
65                  70                  75                  80

Ser Met Glu Asn Ala Asn Lys Trp Ser Cys His Met Cys Thr Tyr Leu
                85                  90                  95

Asn Trp Pro Arg Ala Ile Arg Cys Thr Gln Cys Leu Ser Gln Arg Arg
            100                 105                 110

Thr Arg Ser Pro Thr Glu Ser Pro Gln Ser Ser Gly Ser Gly Ser Arg
            115                 120                 125

Pro Val Ala Phe Ser Val Asp Pro Cys Glu Glu Tyr Asn Asp Arg Asn
130                 135                 140

Lys Leu Asn Thr Arg Thr Gln His Trp Thr Cys Ser Val Cys Thr Tyr
145                 150                 155                 160

Glu Asn Trp Ala Lys Ala Lys Arg Cys Val Val Cys Asp His Pro Arg
            165                 170                 175

Pro Asn Asn Ile Glu Ala Ile Glu Leu Ala Glu Thr Glu Glu Ala Ser
            180                 185                 190

Ser Ile Ile Asn Glu Gln Asp Arg Ala Arg Trp Arg Gly Ser Cys Ser
            195                 200                 205

Ser Gly Asn Ser Gln Arg Arg Ser Pro Pro Ala Thr Lys Arg Asp Ser
            210                 215                 220

Glu Val Lys Met Asp Phe Gln Arg Ile Glu Leu Ala Gly Ala Val Gly
225                 230                 235                 240

Ser Lys Glu Glu Leu Glu Val Asp Phe Lys Lys Leu Lys Gln Ile Lys
            245                 250                 255

Asn Arg Met Lys Lys Thr Asp Trp Leu Phe Leu Asn Ala Cys Val Gly
            260                 265                 270

Val Val Glu Gly Asp Leu Ala Ala Ile Glu Ala Tyr Lys Ser Ser Gly
            275                 280                 285

Gly Asp Ile Ala Arg Gln Leu Thr Ala Asp Glu Val Arg Leu Leu Asn
            290                 295                 300

Arg Pro Ser Ala Phe Asp Val Gly Tyr Thr Leu Val His Leu Ala Ile
305                 310                 315                 320

Arg Phe Gln Arg Gln Asp Met Leu Ala Ile Leu Leu Thr Glu Val Ser
            325                 330                 335

Gln Gln Ala Ala Lys Cys Ile Pro Ala Met Val Cys Pro Glu Leu Thr
            340                 345                 350

Glu Gln Ile Arg Arg Glu Ile Ala Ser Leu His Gln Arg Lys Gly
            355                 360                 365

Asp Phe Ala Cys Tyr Phe Leu Thr Asp Leu Val Thr Phe Thr Leu Pro
            370                 375                 380

Ala Asp Ile Glu Asp Leu Pro Pro Thr Val Gln Glu Lys Leu Phe Asp
385                 390                 395                 400

Glu Val Leu Asp Arg Asp Val Gln Lys Glu Leu Glu Glu Glu Ser Pro
            405                 410                 415

Ile Ile Asn Trp Ser Leu Glu Leu Ala Thr Arg Leu Asp Ser Arg Leu
            420                 425                 430

Tyr Ala Leu Trp Asn Arg Thr Ala Gly Asp Cys Leu Leu Asp Ser Val
            435                 440                 445
```

Leu Gln Ala Thr Trp Gly Ile Tyr Asp Lys Asp Ser Val Leu Arg Lys
    450                 455                 460

Ala Leu His Asp Ser Leu His Asp Cys Ser His Trp Phe Tyr Thr Arg
465                 470                 475                 480

Trp Lys Asp Trp Glu Ser Trp Tyr Ser Gln Ser Phe Gly Leu His Phe
                485                 490                 495

Ser Leu Arg Glu Glu Gln Trp Gln Glu Asp Trp Ala Phe Ile Leu Ser
                500                 505                 510

Leu Ala Ser Gln Pro Gly Ala Ser Leu Glu Gln Thr His Ile Phe Val
            515                 520                 525

Leu Ala His Ile Leu Arg Arg Pro Ile Ile Val Tyr Gly Val Lys Tyr
        530                 535                 540

Tyr Lys Ser Phe Arg Gly Glu Thr Leu Gly Tyr Thr Arg Phe Gln Gly
545                 550                 555                 560

Val Tyr Leu Pro Leu Leu Trp Glu Gln Ser Phe Cys Trp Lys Ser Pro
                565                 570                 575

Ile Ala Leu Gly Tyr Thr Arg Gly His Phe Ser Ala Leu Val Ala Met
                580                 585                 590

Glu Asn Asp Gly Tyr Gly Asn Arg Gly Ala Gly Ala Asn Leu Asn Thr
            595                 600                 605

Asp Asp Asp Val Thr Ile Thr Phe Leu Pro Leu Val Asp Ser Glu Arg
        610                 615                 620

Lys Leu Leu His Val His Phe Leu Ser Ala Gln Glu Leu Gly Asn Glu
625                 630                 635                 640

Glu Gln Gln Glu Lys Leu Leu Arg Glu Trp Leu Asp Cys Cys Val Thr
                645                 650                 655

Glu Gly Gly Val Leu Val Ala Met Gln Lys Ser Ser Arg Arg Arg Asn
                660                 665                 670

His Pro Leu Val Thr Gln Met Val Glu Lys Trp Leu Asp Arg Tyr Arg
            675                 680                 685

Gln Ile Arg Pro Cys Thr Ser Leu Ser Asp Gly Glu Glu Asp Glu Asp
        690                 695                 700

Asp Glu Asp Glu
705

<210> SEQ ID NO 2
<211> LENGTH: 2124
<212> TYPE: DNA
<213> ORGANISM: Homo sapiens

<400> SEQUENCE: 2
atgtcagaac gtggaattaa gtgggcttgt gaatattgta cgtatgaaaa ctggccatct     60
gcaatcaagt gtactatgtg tcgtgcccaa agacctagtg aacaattat tacagaagat    120 ccatttaaaa gtggttcaag tgatgttggt agagattggg atccttccag caccgaagga    180
ggaagtagtc ctttgatatg tccagactct agtgcaagac caagggtgaa atcttcgtat    240
agcatggaaa atgcaaataa gtggtcatgc acatgtgta catatttgaa ctggccaaga    300
gcaatcagat gtacccagtg cttatcccaa cgtaggacca ggagtcctac agaatctcct    360
cagtcctcag gatctggctc aagaccagtt gcttttttctg ttgatccttg tgaggaatac    420
aatgatagaa ataaactgaa cactaggaca cagcactgga cttgctctgt tgcacatat    480 gaaaactggg ccaaggctaa agatgtgtt gtttgtgatc atcccagacc taataacatt    540
gaagcaatag aattggcaga gactgaagag gcttcttcaa taataaatga gcaagacaga    600

-continued

```
gctcgatgga ggggaagttg cagtagtggt aatagccaaa ggagatcacc tcctgctacg    660
aagcgggact ctgaagtgaa aatggatttt cagaggattg aattggctgg tgctgtggga    720
agcaaggagg aacttgaagt agactttaaa aaactaaagc aaattaaaaa caggatgaaa    780
aagactgatt ggctcttcct caatgcttgt gtggggttg tagaaggtga tttagctgcc     840
atagaagcat acaagtcatc aggaggagac attgcacgtc agctcaccgc agatgaagta    900
cgcttgctga atcgtccttc tgcctttgat gttggctata ctcttgtaca cttggctata    960
cgttttcaga ggcaggatat gctagcaata ttgcttacag aggtgtctca acaagcagca   1020
aagtgtattc cagcaatggt gtgtcctgaa ctgacagaac aaatccggag agagatagct   1080
gcctctcttc atcagagaaa gggggatttt gcttgctatt ttctgactga ccttgtaaca   1140
tttacattgc cagcagatat tgaagatttg cccccaacag tccaagaaaa attatttgat   1200
gaggtgcttg atagagacgt tcaaaaagaa ttagaagaag aatctccaat tattaactgg   1260
tccttggaat tggctacacg tttggacagt cgactgtatg cactttggaa ccggactgca   1320
ggagactgcc tacttgattc agttctacaa gctacctggg gcatctatga caaggactca   1380
gtgcttcgga aagccctgca tgacagcctg catgactgtt cacattggtt ttacacacgc   1440
tggaaagatt gggaatcatg gtattctcag agctttggtt tacatttttc cttgagagaa   1500
gaacagtggc aagaagactg gcatttata ctctctcttg ctagtcagcc tggagcaagc    1560
ttggagcaga cgcacatttt tgtactggca catattctta gacgaccaat tatagtttat   1620
ggagtaaaat attacaagag tttccgggga gaaactttag gatatactcg gtttcaaggt   1680
gtttatctgc ctttgttgtg ggaacagagt ttttgttgga aaagtccgat tgctctgggt   1740
tatacgaggg gccacttctc tgctttggtt gccatggaaa atgatggcta tggcaaccga   1800
ggtgctggtg ctaatctcaa taccgatgat gatgtcacca tcacattttt gcctctggtt   1860
gacagtgaaa ggaagctact ccatgtgcac ttcctttctg ctcaggagct aggtaatgag   1920
gaacagcaag aaaaactgct cagggagtgg ctggactgct gtgtgacgga gggggagtt   1980 ctggttgcca tgcagaagag ttctcggcgg cgaaatcacc ccctggtcac tcagatggta   2040
gaaaaatggc ttgaccgcta ccgacagatc cggccgtgta catccctgtc tgatggagag   2100
gaagatgagg atgatgaaga tgaa                                          2124
```

<210> SEQ ID NO 3
<211> LENGTH: 725
<212> TYPE: PRT
<213> ORGANISM: Artificial Sequence
<220> FEATURE:
<223> OTHER INFORMATION: V5-TRABID

<400> SEQUENCE: 3

```
Met Ser Glu Arg Gly Ile Lys Trp Ala Cys Glu Tyr Cys Thr Tyr Glu
1               5                   10                  15

Asn Trp Pro Ser Ala Ile Lys Cys Thr Met Cys Arg Ala Gln Arg Pro
            20                  25                  30

Ser Gly Thr Ile Ile Thr Glu Asp Pro Phe Lys Ser Gly Ser Ser Asp
        35                  40                  45

Val Gly Arg Asp Trp Asp Pro Ser Ser Thr Glu Gly Ser Ser Pro
    50                  55                  60

Leu Ile Cys Pro Asp Ser Ser Ala Arg Pro Arg Val Lys Ser Ser Tyr
65                  70                  75                  80

Ser Met Glu Asn Ala Asn Lys Trp Ser Cys His Met Cys Thr Tyr Leu
```

```
                        85                  90                  95
Asn Trp Pro Arg Ala Ile Arg Cys Thr Gln Cys Leu Ser Gln Arg Arg
                100                 105                 110
Thr Arg Ser Pro Thr Glu Ser Pro Gln Ser Ser Gly Ser Gly Ser Arg
            115                 120                 125
Pro Val Ala Phe Ser Val Asp Pro Cys Glu Glu Tyr Asn Asp Arg Asn
        130                 135                 140
Lys Leu Asn Thr Arg Thr Gln His Trp Thr Cys Ser Val Cys Thr Tyr
145                 150                 155                 160
Glu Asn Trp Ala Lys Ala Lys Arg Cys Val Val Cys Asp His Pro Arg
                165                 170                 175
Pro Asn Asn Ile Glu Ala Ile Glu Leu Ala Glu Thr Glu Glu Ala Ser
                180                 185                 190
Ser Ile Ile Asn Glu Gln Asp Arg Ala Arg Trp Arg Gly Ser Cys Ser
            195                 200                 205
Ser Gly Asn Ser Gln Arg Arg Ser Pro Pro Ala Thr Lys Arg Asp Ser
        210                 215                 220
Glu Val Lys Met Asp Phe Gln Arg Ile Glu Leu Ala Gly Ala Val Gly
225                 230                 235                 240
Ser Lys Glu Glu Leu Glu Val Asp Phe Lys Lys Leu Lys Gln Ile Lys
                245                 250                 255
Asn Arg Met Lys Lys Thr Asp Trp Leu Phe Leu Asn Ala Cys Val Gly
                260                 265                 270
Val Val Glu Gly Asp Leu Ala Ala Ile Glu Ala Tyr Lys Ser Ser Gly
            275                 280                 285
Gly Asp Ile Ala Arg Gln Leu Thr Ala Asp Glu Val Arg Leu Leu Asn
        290                 295                 300
Arg Pro Ser Ala Phe Asp Val Gly Tyr Thr Leu Val His Leu Ala Ile
305                 310                 315                 320
Arg Phe Gln Arg Gln Asp Met Leu Ala Ile Leu Leu Thr Glu Val Ser
                325                 330                 335
Gln Gln Ala Ala Lys Cys Ile Pro Ala Met Val Cys Pro Glu Leu Thr
                340                 345                 350
Glu Gln Ile Arg Arg Glu Ile Ala Ala Ser Leu His Gln Arg Lys Gly
            355                 360                 365
Asp Phe Ala Cys Tyr Phe Leu Thr Asp Leu Val Thr Phe Thr Leu Pro
        370                 375                 380
Ala Asp Ile Glu Asp Leu Pro Pro Thr Val Gln Glu Lys Leu Phe Asp
385                 390                 395                 400
Glu Val Leu Asp Arg Asp Val Gln Lys Glu Leu Glu Glu Ser Pro
                405                 410                 415
Ile Ile Asn Trp Ser Leu Glu Leu Ala Thr Arg Leu Asp Ser Arg Leu
                420                 425                 430
Tyr Ala Leu Trp Asn Arg Thr Ala Gly Asp Cys Leu Leu Asp Ser Val
            435                 440                 445
Leu Gln Ala Thr Trp Gly Ile Tyr Asp Lys Asp Ser Val Leu Arg Lys
        450                 455                 460
Ala Leu His Asp Ser Leu His Asp Cys Ser His Trp Phe Tyr Thr Arg
465                 470                 475                 480
Trp Lys Asp Trp Glu Ser Trp Tyr Ser Gln Ser Phe Gly Leu His Phe
                485                 490                 495
Ser Leu Arg Glu Glu Gln Trp Gln Glu Asp Trp Ala Phe Ile Leu Ser
            500                 505                 510
```

```
Leu Ala Ser Gln Pro Gly Ala Ser Leu Glu Gln Thr His Ile Phe Val
            515                 520                 525

Leu Ala His Ile Leu Arg Arg Pro Ile Ile Val Tyr Gly Val Lys Tyr
        530                 535                 540

Tyr Lys Ser Phe Arg Gly Glu Thr Leu Gly Tyr Thr Arg Phe Gln Gly
545                 550                 555                 560

Val Tyr Leu Pro Leu Leu Trp Glu Gln Ser Phe Cys Trp Lys Ser Pro
                565                 570                 575

Ile Ala Leu Gly Tyr Thr Arg Gly His Phe Ser Ala Leu Val Ala Met
            580                 585                 590

Glu Asn Asp Gly Tyr Gly Asn Arg Gly Ala Gly Ala Asn Leu Asn Thr
        595                 600                 605

Asp Asp Asp Val Thr Ile Thr Phe Leu Pro Leu Val Asp Ser Glu Arg
    610                 615                 620

Lys Leu Leu His Val His Phe Leu Ser Ala Gln Glu Leu Gly Asn Glu
625                 630                 635                 640

Glu Gln Gln Glu Lys Leu Leu Arg Glu Trp Leu Asp Cys Cys Val Thr
                645                 650                 655

Glu Gly Gly Val Leu Val Ala Met Gln Lys Ser Ser Arg Arg Arg Asn
            660                 665                 670

His Pro Leu Val Thr Gln Met Val Glu Lys Trp Leu Asp Arg Tyr Arg
        675                 680                 685

Gln Ile Arg Pro Cys Thr Ser Leu Ser Asp Gly Glu Glu Asp Glu Asp
    690                 695                 700

Asp Glu Asp Glu Val Glu Met Gly Lys Pro Ile Pro Asn Pro Leu Leu
705                 710                 715                 720

Gly Leu Asp Ser Thr
                725

<210> SEQ ID NO 4
<211> LENGTH: 2181
<212> TYPE: DNA
<213> ORGANISM: Artificial Sequence
<220> FEATURE:
<223> OTHER INFORMATION: V5-TRABID

<400> SEQUENCE: 4
atgtcagaac gtggaattaa gtgggcttgt gaatattgta cgtatgaaaa ctggccatct      60
gcaatcaagt gtactatgtg tcgtgcccaa agacctagtg gaacaattat tacagaagat    120
ccatttaaaa gtggttcaag tgatgttggt agagattggg atccttccag caccgaagga    180
ggaagtagtc ctttgatatg tccagactct agtgcaagac caagggtgaa atcttcgtat    240
agcatggaaa atgcaaataa gtggtcatgc cacatgtgta catatttgaa ctggccaaga    300
gcaatcagat gtacccagtg cttatcccaa cgtaggacca ggagtcctac agaatctcct    360
cagtcctcag gatctggctc aagaccagtt gctttttctg ttgatccttg tgaggaatac    420
aatgatagaa ataaactgaa cactaggaca cagcactgga cttgctctgt ttgcacatat    480
gaaaactggg ccaaggctaa agatgtgttt gtttgtgatc atcccagacc taataacatt    540
gaagcaatag aattggcaga gactgaagag cttcttcaa taataaatga gcaagacaga     600
gctcgatgga ggggaagttg cagtagtggt aatagccaaa ggagatcacc tcctgctacg    660
aagcgggact ctgaagtgaa aatggatttt cagaggattg aattggctgg tgctgtggga    720
agcaaggagg aacttgaagt agactttaaa aaactaaagc aaattaaaaa caggatgaaa    780
```

```
aagactgatt ggctcttcct caatgcttgt gtggggttg tagaaggtga tttagctgcc    840
atagaagcat acaagtcatc aggaggagac attgcacgtc agctcaccgc agatgaagta    900
cgcttgctga atcgtccttc tgcctttgat gttggctata ctcttgtaca cttggctata    960
cgttttcaga ggcaggatat gctagcaata ttgcttacag aggtgtctca acaagcagca   1020
aagtgtattc cagcaatggt gtgtcctgaa ctgacagaac aaatccggag agagatagct   1080
gcctctcttc atcagagaaa gggggatttt gcttgctatt ttctgactga ccttgtaaca   1140
tttacattgc cagcagatat tgaagatttg cccccaacag tccaagaaaa attatttgat   1200
gaggtgcttg atagagacgt tcaaaaagaa ttagaagaag aatctccaat tattaactgg   1260
tccttggaat tggctacacg tttggacagt cgactgtatg cactttggaa ccggactgca   1320
ggagactgcc tacttgattc agttctacaa gctacctggg gcatctatga caaggactca   1380
gtgcttcgga aagccctgca tgacagcctg catgactgtt cacattggtt ttacacacgc   1440
tggaaagatt gggaatcatg gtattctcag agctttggtt acatttttc cttgagagaa   1500
gaacagtggc aagaagactg gcatttata ctctctcttg ctagtcagcc tggagcaagc   1560
ttggagcaga cgcacatttt tgtactggca catattctta gacgaccaat tatagtttat   1620
ggagtaaaat attacaagag tttccgggga gaaactttag gatatactcg gtttcaaggt   1680
gtttatctgc ctttgttgtg ggaacagagt ttttgttgga aagtccgat tgctctgggt   1740
tatacgaggg gccacttctc tgctttggtt gccatggaaa atgatggcta tggcaaccga   1800
ggtgctggtg ctaatctcaa taccgatgat gatgtcacca tcacattttt gcctctggtt   1860
gacagtgaaa ggaagctact ccatgtgcac ttcctttctg ctcaggagct aggtaatgag   1920
gaacagcaag aaaaactgct cagggagtgg ctggactgct gtgtgacgga gggggagtt   1980
ctggttgcca tgcagaagag ttctcggcgg cgaaatcacc ccctggtcac tcagatggta   2040
gaaaaatggc ttgaccgcta ccgacagatc cggccgtgta catccctgtc tgatggagag   2100
gaagatgagg atgatgaaga tgaagtcgag atgggtaagc ctatccctaa ccctctcctc   2160
ggtctcgatt ctacgtgata a                                             2181
```

<210> SEQ ID NO 5
<211> LENGTH: 14
<212> TYPE: PRT
<213> ORGANISM: Artificial Sequence
<220> FEATURE:
<223> OTHER INFORMATION: V5 tag

<400> SEQUENCE: 5

Gly Lys Pro Ile Pro Asn Pro Leu Leu Gly Leu Asp Ser Thr
1               5                   10

<210> SEQ ID NO 6
<211> LENGTH: 42
<212> TYPE: DNA
<213> ORGANISM: Artificial Sequence
<220> FEATURE:
<223> OTHER INFORMATION: V5 tag

<400> SEQUENCE: 6
ggtaagccta tccctaaccc tctcctcggt ctcgattcta cg                       42

<210> SEQ ID NO 7
<211> LENGTH: 21
<212> TYPE: DNA
<213> ORGANISM: Artificial Sequence
<220> FEATURE:

<223> OTHER INFORMATION: Luciferase shRNA

<400> SEQUENCE: 7
cttcgaaatg tccgttcggt t                                              21

<210> SEQ ID NO 8
<211> LENGTH: 21
<212> TYPE: DNA
<213> ORGANISM: Artificial Sequence
<220> FEATURE:
<223> OTHER INFORMATION: TRABID shRNA#6

<400> SEQUENCE: 8
ccatagaagc atacaagtca t                                              21

<210> SEQ ID NO 9
<211> LENGTH: 21
<212> TYPE: DNA
<213> ORGANISM: Artificial Sequence
<220> FEATURE:
<223> OTHER INFORMATION: TRABID shRNA#9

<400> SEQUENCE: 9
caagggtgaa atcttcgtat a                                              21

<210> SEQ ID NO 10
<211> LENGTH: 21
<212> TYPE: DNA
<213> ORGANISM: Artificial Sequence
<220> FEATURE:
<223> OTHER INFORMATION: UBE3C shRNA#2

<400> SEQUENCE: 10
gtcctatttc tatctccact t                                              21

<210> SEQ ID NO 11
<211> LENGTH: 21
<212> TYPE: DNA
<213> ORGANISM: Artificial Sequence
<220> FEATURE:
<223> OTHER INFORMATION: UBE3C shRNA#4

<400> SEQUENCE: 11
gcagataagc aagaagttca a                                              21

<210> SEQ ID NO 12
<211> LENGTH: 20
<212> TYPE: DNA
<213> ORGANISM: Artificial Sequence
<220> FEATURE:
<223> OTHER INFORMATION: UBE3C sgRNA#1

<400> SEQUENCE: 12
cggcggcgct gcccgcacat                                                20

<210> SEQ ID NO 13
<211> LENGTH: 20
<212> TYPE: DNA
<213> ORGANISM: Artificial Sequence
<220> FEATURE:
<223> OTHER INFORMATION: UBE3C sgRNA#2

<400> SEQUENCE: 13
ctggactcgg ggccgagact                                                20

METHOD FOR PREVENTING OR TREATING METABOLIC DISORDER

BACKGROUND

1. Technical Field

The present disclosure relates to methods for improving disorders susceptible to amelioration by tumor-necrosis factor receptor-associated factor (TRAF)-binding protein domain (TRABID)-induced deubiquitination, and particularly to methods for preventing or treating metabolic disorders such as obesity and fatty liver disease that comprises increasing TRABID expression in a subject in need thereof.

2. Description of Related Art

The current epidemic of obesity and metabolic disorders such as type II diabetes are global health problems. These disorders are associated with an excessive nutritional intake and lack of exercise of the Western lifestyle and increasingly that of the rest of the world. It is estimated that over 500 million individuals are obese, and obesity per se increases the risk of mortality and has been long strongly associated with insulin resistance and type II diabetes.

In addition, the growing incidence of obesity in the population as a whole has made fatty liver disease and its complications a leading public health issue. The liver has a predominate role in fat metabolism and normally accumulates lipids, but only to "normal levels." Excessive lipid accumulation in hepatocytes results in hepatic steatosis, which is metabolically harmful and can result from a variety of liver dysfunctions, such as decreased beta-oxidation or decreased secretion of lipoproteins.

Nonalcoholic fatty liver disease (NAFLD) is the most common liver disease with a global prevalence about 25% and is characterized by increased liver fat content, and autophagy represents one mechanism to degrade lipid droplets, which are an organelle for fat storage. NAFLD covers a spectrum of diseases from steatosis to nonalcoholic steatohepatitis (NASH) and is linked to other metabolic disorders such as cardiovascular disorder, type II diabetes and hypertension. NASH is the most extreme form of NAFLD and is regarded as a major cause of cirrhosis of the liver of an unknown cause. Liver transplantation is the only curative option for patients with advanced liver cirrhosis. However, such procedure can only be applied to a minority of patients due to the presence of surgical contraindications and organ scarcity.

Accordingly, despite the obvious health benefits, compliance with lifestyle changes to achieve sustained improvements in diet or obesity has proved challenging for the general population. Hence, agents to lower excessive fat accumulation as well as prevent or treat metabolic disorders, e.g., NAFLD, would be attractive and of a practical benefit.

SUMMARY

In view of the foregoing, the present disclosure provides a method for preventing or treating a condition or a disorder susceptible to amelioration by increasing TRABID expression.

In at least one embodiment of the present disclosure, a method for preventing or treating a metabolic disorder in a subject in need thereof is provided. The method comprising administering to the subject a therapeutically effective amount of TRABID protein or a functionally related variant thereof, or a nucleic acid encoding the TRABID protein or a functionally related variant thereof.

In at least one embodiment of the present disclosure, the TRABID protein may comprise an amino acid sequence of SEQ ID NO:1 or SEQ ID NO:3, and the nucleic acid encoding the TRABID protein comprises a nucleic acid sequence of SEQ ID NO:2 or SEQ ID NO:4.

In at least one embodiment of the present disclosure, the functionally related variant of the TRABID protein comprises an amino acid sequence having at least 80% (e.g., 80%, 85%, 90%, 95%, 97%, 98%, 99% or 100%) sequence identity to SEQ ID NO:1 or SEQ ID NO:3, and the functionally related variant of the nucleic acid encoding the TRABID protein comprises a nucleic acid sequence having at least 80% (e.g., 80%, 85%, 90%, 95%, 97%, 98%, 99% or 100%) sequence identity to SEQ ID NO:2 or SEQ ID NO:4.

In at least one embodiment of the present disclosure, the metabolic disorder to be prevented or treated by the method may be pre-diabetes, diabetes, obesity, diabetic dyslipidemia, hyperlipidemia, hypertriglyceridemia, hyperfattyacidemia, hypercholesterolemia, or fatty liver disease. In some embodiments, the fatty liver disease may be non-alcoholic fatty liver disease (NAFLD), alcoholic fatty liver disease, alcoholic steatohepatitis, non-alcoholic steatohepatitis (NASH), liver steatosis, liver cirrhosis, or liver fibrosis. In some embodiments, the metabolic disorder is obesity or fatty liver disease.

In at least one embodiment of the present disclosure, a method for reducing fat accumulation in a subject in need thereof is also provided. The method comprises administering to the subject a therapeutically effective amount of TRABID protein or a functionally related variant thereof, or a nucleic acid encoding the TRABID protein or a functionally related variant thereof.

In at least one embodiment of the present disclosure, the reduction of fat accumulation comprises reducing body fat accumulation in the subject, reducing excessive fat from liver of the subject, reducing weight of the subject, preventing weight gain in the subject or any combination thereof.

In at least one embodiment of the present disclosure, the administration of the TRABID protein, the nucleic acid encoding the TRABID protein, or the functionally related variant thereof results in autophagosome biogenesis in the subject. In some embodiments, the administration promotes at least one of autophagy activity and lipid metabolism, as well as reduction of a serum level of at least one of alanine aminotransferase (ALT) and aspartate aminotransferase (AST) in the subject.

In at least one embodiment of the present disclosure, the nucleic acid encoding the TRABID protein or the functionally related variant thereof is administered to the subject by a recombinant adeno-associated virus (rAAV) viral vector. In some embodiments, the method of the present disclosure comprises administering to the subject an rAAV viral vector comprising the nucleic acid encoding the TRABID protein or the functional variant thereof. In some embodiments, the viral vector further comprises an AAV8 capsid.

In at least one embodiment of the present disclosure, the method further comprises administering at least one additional therapy for the metabolic disorder to the subject. In some embodiments, the additional therapy may be a medication for a metabolic disorder, including, but not limited to, insulin or an insulin analog, a lipid-lowering agent, an α-glucosidase inhibitor, a glucagon-like peptide-1 (GLP-1)

analog, a sodium glucose transporter-2 (SGLT2) inhibitor, sulfonylurea, meglitinide, thiazolidinedione, or any combination thereof.

In at least one embodiment of the present disclosure, an artificial nucleic acid molecule that is useful for the methods of the present disclosure is further provided. The artificial nucleic acid molecule comprises a nucleic acid encoding a TRABID protein or a functionally related variant thereof, as mentioned above, and a nucleotide tag sequence encoding a peptide tag. In some embodiments, the methods of the present disclosure comprise administering to the subject an rAAV viral vector comprising the artificial nucleic acid molecule.

In at least one embodiment of the present disclosure, the artificial nucleic acid molecule comprises a nucleic acid sequence of SEQ ID NO:3, and encodes the TRABID protein with the peptide Tag. In some embodiments, the TRABID protein with the peptide Tag comprises an amino acid sequence of SEQ ID NO:4.

In the present disclosure, an autophagy promoting factor, TRABID, is provided to stabilize an autophagy player, VPS34, through deubiquitination. By increasing TRABID expression, the method provided in the present disclosure may improve the balance between a ubiquitin ligase and a deubiquitinating enzyme on autophagy regulation. Hence, the method of the present disclosure is effective in preventing or treating a metabolic disorder, alleviating disorder-related symptoms, as well as reducing fat accumulation.

BRIEF DESCRIPTION OF THE DRAWINGS

This patent application/patent file contains at least one drawing executed in color. Copies of this patent or patent application publication with color drawing(s) will be provided by the Office upon request and payment of the necessary fee.

The present disclosure can be more fully understood by reading the following descriptions of the embodiments, with reference made to the accompanying drawings.

FIG. 1A shows that HeLa-GFP-LC3 cells stably expressing control or TRABID shRNAs are starved for indicated time points and then analyzed for GFP-LC3 puncta, wherein representative confocal images are shown on the left and quantitative data are on the right. Dashed lines: outlines of cells. Bar: 10 μm. FIGS. 1B and 1C show the results of Western blot analysis of LC3 in HeLa cells stably expressing control or TRABID shRNA cultured in starvation for 0 or 4 h (FIG. 1B) or cultured in starvation with 100 nM bafilomycin A1 for 0 or 2 h (FIG. 1C). The knockdown efficiencies are shown on the bottom panel of FIG. 1B. FIG. 1D shows immunofluorescence staining of LC3 in HeLa cells stably expressing Flag-TRABID and cultured in starvation for 0 or 2 h, wherein representative confocal images are shown on the left and quantitative data are on the right. Bar: 10 μm. FIG. 1E shows the result of Western blot analysis of LC3 in cells as in FIG. 1D cultured in fed or starved conditions in the presence of bafilomycin A1 for 2 h. FIGS. 1F and 1G show the results of Western blot analysis of S6, ULK1 and ATG13 phosphorylation in HeLa cells stably expressing TRABID shRNAs cultured in fed or starvation for 2 h. FIGS. 1H to 1J show that HeLa-derived cells as in FIG. 1B are transiently transfected with GFP-DFCP1 (FIG. 1H) or untransfected (FIG. 1I) or transfected with GFP-ATG14 (FIG. 1J), and cultured in fed or starved conditions for indicated time periods, and then GFP-DFCP1 puncta are analyzed directly by confocal microcopy, whereas ATG16 puncta are analyzed by immunofluorescence staining followed by confocal microscopy. Representative images are shown on the left, and quantitative data are on the right. Bar: 10 μm. Data are mean±SD (n=3 independent experiments, and 30 cells per group per experiment are counted); *P<0.5, P<0.01, *P<0.001.

FIGS. 2A to 2E and 2H show the results of Western blot analysis of VPS34, AMBRA1, Beclin1, ATG14, UVRAG and VPS34 K48 ubiquitination in 293T cells transfected with indicated constructs, respectively. WT: wild type. cs: TRABID catalytically dead mutant.

FIGS. 2S and 2T show the results of immunofluorescence analysis of autophagosome maturation in HeLa-RFP-GFP-LC3 cells stably expressing TRABID shRNAs or TRABID construct cultured in starvation for 0 or 2 h, wherein representative images are shown on the left, boxed areas are enlarged, and the ratios of red puncta to total puncta are quantified and plotted on the right. Bar: 10 μm. Data are mean±SD (n=3 independent experiments, and 10 cells per group per experiment are counted); ***P<0.001 by t test.

FIGS. 3A to 3S are graphs illustrating that UBE3C induces VPS34 K29/K48 branched ubiquitination, leading to an enhanced VPS34 proteasomal degradation. FIG. 3A shows the results of reciprocal immunoprecipitation analysis of the interaction between UBE3C and VPS34 in 293T cells. FIG. 3B shows in vitro interaction of baculovirally purified Flag-VPS34 with separately purified HA-UBE3C. FIG. 3C shows the analysis results of VPS34 ubiquitination in 293T cells transfected with indicated constructs, wherein VPS34 is immunoprecipitated by M2 beads, followed by Western blot analysis with indicated antibodies. FIGS. 3D to 3H show the analysis results of VPS34 ubiquitination in 293T cells transfected with indicated constructs, wherein the ubiquitinated proteins are pulled down by Ni-NTA agarose under denaturing conditions and analyzed by Western blot with indicated antibodies. WT: wild type. cs: TRABID catalytically dead mutant. FIG. 3I shows the in vitro ubiquitination of Flag-VPS34 purified from 293T cells in the presence or absence of baculovirally purified UBE3C, wherein the reaction mixture is analyzed by Western blot with indicated antibodies. FIGS. 3O and 3P shows the results of Western blot analysis of VPS34 levels in HeLa cells stably expressing UBE3C shRNAs (FIG. 3O) or in the two clones of 293T UBE3C KO cells (FIG. 3P). FIG. 3Q shows the results of immunoprecipitation analysis for the binding of proteasome subunit S5A with ubiquitinated VPS34 in wild type (WT) or K29R ubiquitin replacement cells transfected with indicated constructs and treated with or without doxycycline. FIGS. 3R and 3S show the results of Western blot analysis of VPS34 levels in indicated ubiquitin replacement cells transfected with or without UBE3C siRNA and treated with doxycycline for at least 96 h together with cycloheximide (CHX) for MG132 for 16 h (FIG. 3R) or indicated time points (FIG. 3S). The knockdown efficiency of UBE3C siRNA is shown on the right panel of FIG. 3S.

FIGS. 4A to 4H are graphs illustrating that UBE3C and TRABID coordinately lead to a balanced autophagy activity. FIGS. 4A and 4C shows the results of immunofluorescence staining of LC3 in HeLa cells stably expressing UBE3C shRNA and cultured in fed conditions or starved for 2 h in the absence (FIG. 4A) or presence (FIG. 4C) of bafilomycin A1, and FIGS. 4B and 4D shows the results of immunofluorescence staining of LC3 in 293T UBE3C KO cells cultured in fed or starved conditions in the absence (FIG. 4B) or presence (FIG. 4D) of bafilomycin A1 for 2 h, wherein representative confocal images are shown on the left and quantitative data are on the right. Bar: 10 μm. FIG. 4E shows the results of immunoprecipitation analysis of the interaction between UBE3C and indicated subunits of VPS34 complexes I and II in 293T cells transfected with Flag-UBE3C. FIG. 4F shows the results of immunofluorescence analysis of autophagosome maturation in indicated HeLa-RFP-GFP-LC3 cells cultured in fed or starvation conditions for 2 h, wherein representative images are shown on the left, and the ratios of red puncta to total puncta are quantified and plotted on the right. Bar: 10 μm. FIG. 4G shows the results of Western blot analysis of UBE3C, TRABID and VPS34 in HeLa cells stably expressing UBE3C shRNA and/or TRABID shRNA. FIG. 4H shows the immunofluorescence staining of LC3 in HeLa-derived cells as in FIG. 4G and cultured in fed conditions or starved for 2 h, wherein representative confocal images are shown on the left, and quantitative data are on the right. Bar: 10 μm. Data are mean±SD (n=3 independent experiments, and 30 cells or 10 cells (FIG. 4H) per group per experiment are counted); *P<0.5, P<0.01, *P<0.001 by two-way ANOVA with Turkey's post hoc test.

FIG. 5A shows the results of immunoprecipitation analysis of the interaction between UBE3C and VPS34 in 293T cells treated with 500 μM thapsigargin (Tg), 10 μg/mL tunicamycin (Tu), 10 μM MG132, 10 μM 17-DMAG, 10 μM 17-AAG, 10 μg/mL puromycin (Puro) or starved (EBSS) for 30 min. FIG. 5N shows the results of immunoprecipitation analysis of the interaction between UBE3C and proteasome subunit SSA in 293T cells treated with indicated agents for 30 min. Data are mean±SD (n=3 independent experiments, and 5 cells per group per experiment were counted); *P<0.05, P<0.01,*P<0.001 by t test.

FIGS. 6A and 6B show that 293T UBE3C KO-derived targeting (T) or control cells (C) are treated with 10 μg/mL puromycin or tunicamycin together with or without 0.5 μM rapalog for 30 min (FIG. 6A) or 2 h (FIG. 6B) and analyzed by Western blot for the interaction between transfected UBE3C and VPS34. FIG. 6C shows the results of immunofluorescence analysis of 293T UBE3C KO-derived targeting or control cells treated with puromycin and/or rapalog for 2 h, wherein representative images are on the left and quantitative data are on the right. Boxed regions are enlarged images. Bar: 10 μm. FIG. 6D shows that 293T UBE3C KO-derived targeting or control cells are treated as the scheme outlined and analyzed by immunostaining for ubiquitin/p62 double-positive aggregates. Representative images are on the left and quantitative data are on the right. Arrowheads indicate the double positive dots. Bar: 10 μm. FIG. 6E shows that 293T UBE3C KO-derived targeting or control cells are treated with puromycin for 2 h; after washing out puromycin, cells are treated with rapalog and recovered for 4 h and analyzed by immunofluorescence staining for ubiquitin. Representative images are on the left and quantitative data are on the right. Bar: 10 μm. FIG. 6F shows that 293T UBE3C KO-derived targeting or control cells are treated as in FIG. 6E, stained by PROTEOSTAT dye and analyzed by flow cytometry for mean fluorescence intensity (MFI). FIG. 6G shows the immunostaining of 293T UBE3C KO-derived targeting or control cells treated with tunicamycin and/or rapalog for 6 h, wherein representative images are on the left and quantitative data are on the right, and arrowheads indicate double positive dots. Bar: 10 μm. FIG. 6H shows the results of Western blot analysis of cells as in FIG. 6G treated with tunicamycin, rapalog, and/or bafilomycin A1 for 6 h. FIGS. 6I and 6J show that 293T UBE3C KO-derived targeting or control cells as in FIG. 6B are treated with puromycin or tunicamycin together with rapalog for 3 h (FIG. 6I) or 6 h (FIG. 6J) and analyzed for apoptosis. Data are mean±SD (n=3 independent experiments, and 30 cells per group per experiment are counted), ***P<0.001 by two-way ANOVA with Turkey's post hoc test.

FIGS. 7A to 7J are graphs illustrating that TRABID-mediated VPS34 stabilization controls liver metabolism to alleviate NAFLD. FIG. 7A is schematic representation of the experimental design to evaluate the role of TRABID-mediated VPS34 regulation in the NAFLD mouse model. FIGS. 7B and 7H show the results of Western blot analysis of the expression levels of indicated proteins in liver tissues taken from mice on normal diet (ND) or high fat diet (HFD). FIG. 7C shows the immunofluorescence staining of LC3 in liver sections from indicated mice, wherein representative images are on the left and quantitative data are on the right. Bar: 10 μm. Data are mean±SD (n=6, 40-70 cells/section were counted). FIGS. 7D and 7G show the percentage of liver per body weight and liver triglyceride (TG) levels in indicated mice. Data are mean±SD from 6 mice. FIG. 7E shows H&E and Oil Red O staining of liver sections taken from indicated mice. Bar: 50 μm, wherein the percentages of area stained positive for Oil Red O are quantified and shown on the right. FIG. 7F shows gross view for the livers taken from indicated mice. Bar: 1 cm. FIGS. 7I and 7J show the results of AST and ALT assays in indicated mice. Data are mean±SD from 6 mice. ***P<0.001 by one-way ANOVA with Turkey's post hoc test.

DETAILED DESCRIPTION OF THE EMBODIMENTS

Figure 1A:
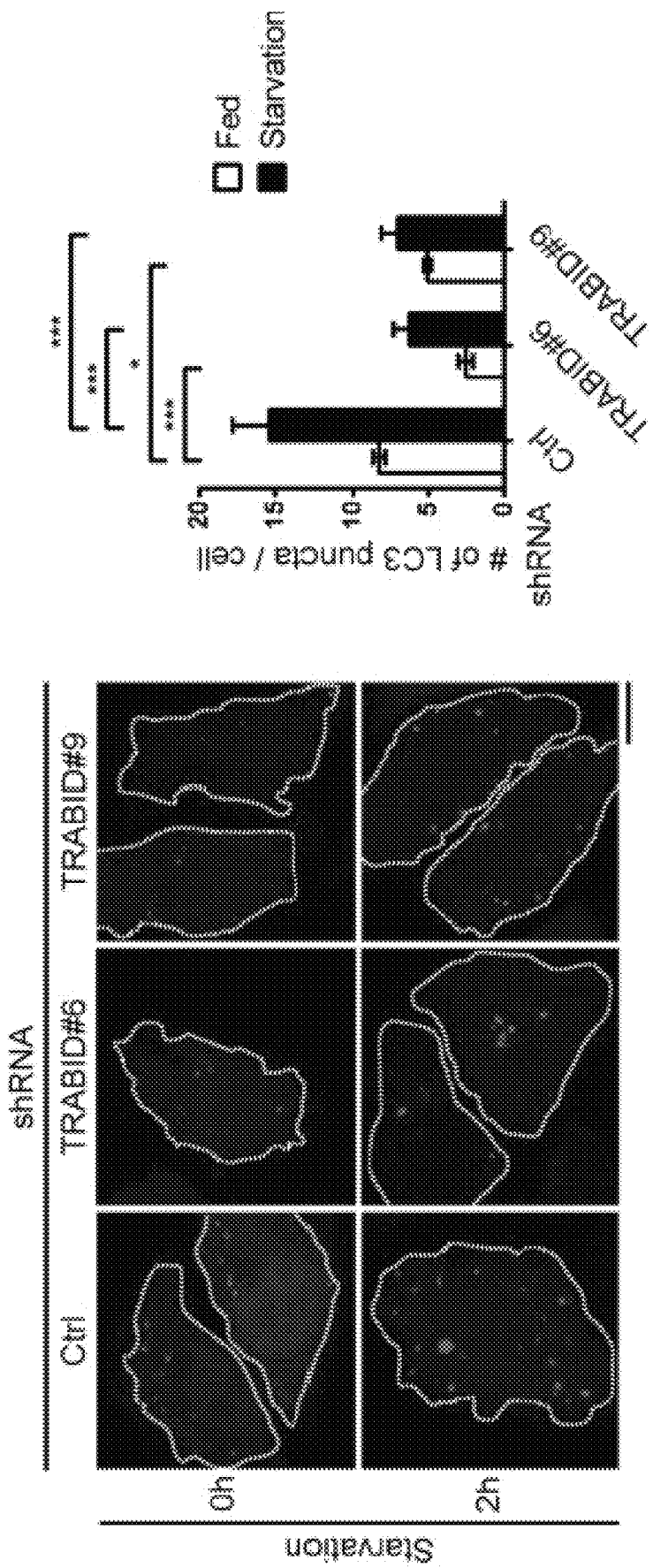
FIGS. 1A to 1J are graphs illustrating that TRABID promotes autophagosome biogenesis without affecting mTOR, AMPK and ULK1 activities.

The following examples are used for illustrating the present disclosure. A person skilled in the art can easily conceive the other advantages and effects of the present disclosure, based on the disclosure of the specification. The present disclosure can also be implemented or applied as described in different examples. It is possible to modify or alter the following examples for carrying out this disclosure without contravening its scope, for different aspects and applications.

It is further noted that, as used in this disclosure, the singular forms "a," "an," and "the" include plural referents, unless expressly and unequivocally limited to one referent. The term "or" is used interchangeably with the term "and/or," unless the context clearly indicates otherwise.

As used herein, the term "comprising" or "comprises" is used in reference to compositions, methods, and respective component(s) thereof, which are included in the present disclosure, yet open to the inclusion of unspecified elements.

The present disclosure is directed to a method for preventing or treating a metabolic disorder in a subject in need thereof. The method comprises administering to the subject a therapeutically effective amount of a TRABID protein or a functionally related variant thereof, or a nucleic acid encoding the TRABID protein or a functionally related variant thereof, thereby increasing the TRABID expression in the subject.

The present disclosure is also directed to a method for reducing fat accumulation in a subject in need thereof by increasing the TRABID expression. In at least one embodiment of the present disclosure, the reduction of fat accumulation comprises reducing body fat accumulation in the subject, reducing excessive fat from liver of the subject, reducing weight of the subject, or preventing weight gain in the subject.

As used herein, the term "TRABID" refers to a deubiquitinating enzyme (DUB) with its general meaning in the art. In addition, TRABID is identified in the preset disclosure to potentiate vacuolar protein sorting 34 (VPS34) deubiquitination and stabilization so as for autophagosome biogenesis.

As used herein, the terms "VPS34" and "VPS34 complex" (also known as the class III phosphoinositide 3 (PI3)-kinase complex) are used interchangeably and refer to a hub of ubiquitin-dependent regulation. The VPS34 complex catalyzes the production of phosphatidylinositol-3-phosphate (PI3P) and is required for both bulk and selective types of autophagy by controlling both autophagosome formation and maturation. In addition, VPS34 is regulated by K29/K48 branched ubiquitination through the reciprocal actions of a ubiquitin ligase, ubiquitin-protein ligase E3C (UBE3C), and a deubiquitinating enzyme, tumor-necrosis factor receptor-associated factor (TRAF)-binding protein domain (TRABID).

As used herein, the term "ubiquitination" refers to the attachment of the ubiquitin protein to a lysine residue of other molecules. Ubiquitination of a molecule, such as a peptide or protein, can act as a signal for its rapid cellular degradation, and for targeting to the proteasome complex. As used herein, the term "ubiquitin ligase" refers to a family of proteins that facilitate the transfer of ubiquitin to a substrate protein and target that substrate protein for degradation.

In at least one embodiment of the present disclosure, the TRABID protein or the functionally related variant thereof may be tagged with a peptide tag, or the nucleic acid encoding the TRABID protein or the functionally related variants thereof may be tagged with a nucleotide tag sequence encoding a peptide tag. In some embodiments, the peptide tag may be V5-tag, Flag tag, poly(His), myc-tag, or Halo-tag.

As used herein, the term "nucleotide tag sequence" refers to a predetermined nucleotide sequence that is added to a target nucleotide sequence (e.g., a nucleic acid encoding the TRABID protein). The nucleotide tag sequence encodes a peptide tag for reporting an item of information about the target nucleotide sequence, such as the identity of the target nucleotide sequence. In some embodiments, the nucleotide tag sequence may encode one or more peptide tags.

In at least one embodiment of the present disclosure, the TRABID protein comprises an amino acid sequence of SEQ ID NO:1 or SEQ ID NO:3. In some embodiments, the functionally related variant of the TRABID protein comprises an amino acid sequence having at least 80%, at least 85%, at least 90%, at least 92%, at least 95%, at least 96%, at least 97%, at least 98% or at least 99% sequence identity to SEQ ID NO:1 or SEQ ID NO:3. In at least one embodiment of the present disclosure, the TRABID protein is represented by SEQ ID NO:1. In at least one embodiment of the present disclosure, the TRABID protein is tagged with V5-tag (i.e., SEQ ID NO:5) and represented by SEQ ID NO:3.

In at least one embodiment of the present disclosure, the nucleic acid encoding the TRABID protein comprises a nucleic acid sequence of SEQ ID NO:2 or SEQ ID NO:4. In some embodiments, the functionally related variant of the nucleic acid encoding the TRABID protein comprises a nucleic acid sequence having at least 80%, at least 85%, at least 90%, at least 92%, at least 95%, at least 96%, at least 97%, at least 98% or at least 99% sequence identity to SEQ ID NO:2 or SEQ ID NO:4. In at least one embodiment of the present disclosure, the nucleic acid encoding the TRABID protein is represented by SEQ ID NO:2. In at least one embodiment of the present disclosure, the nucleic acid encoding the TRABID protein is tagged with nucleotide V5-tag sequence (i.e., SEQ ID NO:6) and represented by SEQ ID NO:4.

As used herein, the term "functionally related variant" refers to a polypeptide or a polynucleotide, which is homologous to the reference polypeptide or polynucleotide (e.g., the TRABID protein or a nucleic acid encoding the TRABID protein) and has the same or enhanced functional activity of the reference, but differs from the reference in sequence. The functionally related variant is derived in that one or more amino acids or nucleotides are added into the reference sequence and/or one or more amino acids or nucleotides within the reference sequence are deleted or substituted for other amino acids or nucleotides.

Amino acid substitutions may be regarded as "conservative" where an amino acid is replaced with a different amino acid with broadly similar properties. Non-conservative substitutions are where amino acids are replaced with amino acids of a different type. Generally speaking, fewer non-conservative substitutions are possible without altering the biological activity of the polypeptide.

As used herein, the term "sequence identity" or, for example, comprising a "sequence having 80% sequence identity to" refers to the extent that sequences are identical on a nucleotide-by-nucleotide basis or an amino acid-by-amino acid basis over a window of comparison. Therefore, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence homology. Included are polynucleotides and polypeptides having at least about 80%, at least about 85%, at least about 90%, at least about 95%, at least about 97%, at least about 98%, at least about 99% or about 100% sequence homology to any of the reference sequences described herein (e.g., in the Sequence Listing), typically where the polypeptide variant maintains at least one biological activity or function of the reference polypeptide.

As used herein, the term "administering" or "administration" refers to the placement of an active agent (e.g., the TRABID protein) into a subject by a method or route which results in at least partial localization of the active agent at a desired site such that a desired effect is produced. The active agent described herein can be administered by any appropriate route known in the art including, but not limited to, oral or parenteral routes, including intraperitoneal, intravenous, intradermal, intramuscular, subcutaneous, or transdermal routes.

In at least one embodiment of the present disclosure, the nucleic acid encoding the TRABID protein or the functionally related variants thereof may be administered to the subject by a method selected from the group consisting of electroporation, diethylaminoethyl (DEAE) dextran transfection, calcium phosphate transfection, cationic liposome fusion, protoplast fusion, creation of an in vivo electric field, DNA-coated microprojectile bombardment, injection with recombinant replication-defective viruses, homologous recombination, a viral vector, and naked DNA transfer.

In at least one embodiment of the present disclosure, the TRABID protein or the functionally related variants thereof, or the nucleic acid encoding the TRABID protein or the functionally related variants thereof may be administered to the subject in combination with one or more additional therapies. In some embodiments, the active agent described herein (e.g., the TRABID protein) and one or more additional therapies are administered either together in a single formulation, or administered separately in different formulations. In some embodiments, the administration of the active agent described herein and the additional therapy are done concomitantly, or in series.

As used herein, the terms "therapies" and "therapy" refer to any protocol(s), method(s), composition(s), formulation(s), and/or agent(s) that can be used in prevention or treatment of a metabolic disorder or symptom associated therewith. In some embodiments, the terms "therapies" and "therapy" may refer to biological therapy, supportive therapy, and/or other therapies useful in treatment or prevention of a metabolic disorder or symptom associated therewith known to one of skill in the art.

As used herein, the phrase "a therapeutically effective amount" refers to the amount of an active agent (e.g., the TRABID protein) that is required to confer a desired therapeutic effect (e.g., reduction of excessive fat accumulation) on the treated subject. Effective doses will vary, as recognized by those skilled in the art, depending on routes of administration, excipient usage, the possibility of co-usage with other therapeutic treatment, and the condition to be treated.

As used herein, the terms "treat," "treating," and "treatment" refer to acquisition of a desired pharmacologic and/or physiologic effect, e.g., alleviating or abrogating a disorder, disease, or condition, or one or more of the symptoms associated with the disorder, disease, or condition, or alleviating or eradicating the cause(s) of the disorder, disease, or condition itself. The effect may be prophylactic in terms of completely or partially preventing a disease or symptom thereof or may be therapeutic in terms of completely or partially curing, alleviating, relieving, remedying, or ameliorating a disease or an adverse effect attributable to the disease or symptom thereof.

As used herein, the terms "prevent," "preventing," and "prevention" refer to inclusion of a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

As used herein, the term "subject" refers to a mammal, such as a human, but can also be another animal such as a domestic animal (e.g., a dog, a cat, or the like), a farm animal (e.g., a cow, a sheep, a pig, a horse, or the like) or a laboratory animal (e.g., a monkey, a rodent, a murine, a rabbit, a guinea pig, or the like). The term "patient" refers to a "subject" who is suspected to be, or afflicted with a disease or condition.

Many examples have been used to illustrate the present disclosure. The examples below should not be taken as a limit to the scope of the present disclosure.

EXAMPLES

Materials and Methods

The materials and methods used in the following Examples 1 to 10 were described in detail below. The materials used in the present disclosure but unannotated herein were commercially available.

(1) Plasmid Preparation

Plasmids encoding RFP-GFP-LC3, GFP-DFCP1, GFP-ATG14L, GFP-UVRAG, and TagRFP-ATG16L were kindly provided by Wei-Yuan Yang (Academia Sinica, Taipei, Taiwan).

Plasmids encoding His-ubiquitin and its KR mutant and K-only mutant, V5-TRABID, Flag-Beclin1, and Flag-VPS34 were described previously[1,2]. His-K29/K48-only ubiquitin, His-K29R/K48R ubiquitin, and V5-TRABID C443S were generated by site-directed mutagenesis.

The cDNAs for V5-VPS34 and His-VPS34 were generated by polymerase chain reaction (PCR) and subcloned to pRK5 (kindly provided by Dr. Rik Derynck (University of California, San Francisco)) and pET32a (SnapGene, Inc.), respectively. The cDNA for TRABID was subcloned to pRK5-V5 (prepared by inserting a V5 tag into pRK5), pEGFP-C1 (Clontech, Inc.) and pLAS5W.Pneo (National RNAi Core Facility, Taiwan). The cDNA for UBE3C (NCBI/NP_055486.2; 1 to 1083 aa) was synthesized by AllBio Science, Inc. (Taichung, Taiwan) and subcloned to pRK5F (prepared by inserting a Flag tag into pRK5), pEBFP-C1 (Clontech, Inc.), pEGFP-C2 (Clontech, Inc.) and pVL1392 (Thermo Fisher Scientific, Inc.). UBE3C C1051S (cs) was generated by site-directed mutagenesis and subcloned to pRK5F. AMBRA1 cDNA was amplified from mRNA derived from 293T cells by real time (RT)-PCR and subcloned to pRK5F.

Plasmids encoding Flag-FKBP12-UBE3C and V5-FRB-VPS34 were generated by inserting the FKBP12 fragment (from pmCherry-FKBP12-C1; Plasmid #67900; Addgene) and FRB fragment (from pEGFP-FRB; Plasmid #25919; Addgene) into pRK5-Flag-UBE3C (i.e., pRK5 with a Flag tag and UBE3C) and pRK5-V5-VPS34 (i.e., pRK5 with a V5 tag and VPS34), respectively.

(2) Antibodies and Reagents

To generate polyclonal antibodies against TRABID, two TRABID fragments corresponding to the three Np14-like zinc finger domains (3NZF; residues 1 to 200) and the ankyrin-repeat domain (Ank; residues 260 to 340) were cloned to pET32a to generate 6×His-tagged recombinant proteins. The recombinant proteins were purified using Ni Sepharose (GE Healthcare) under denaturing conditions and used as antigens. Antiserum production and affinity purification were performed by LTK BioLaboratories (Taipei, Taiwan).

Other antibodies used in this disclosure are described in the following Table 1.

TABLE 1

Antibody details

| Antibody | Company | Cat. Number | Source | Note |
|---|---|---|---|---|
| TRABID (3NZF) | LTK BioLaboratories | Homemade | Rabbit | WB (1:1000) |
| TRABID (Ank) | LTK BioLaboratories | Homemade | Rabbit | WB (1:1000) |
| TRABID | Merck Millipore | ABS13 | Rabbit | IP (1:100) |
| V5 | Merck Millipore | AB3792 | Rabbit | WB (1:3000) |
| Phospho-ULK1 (Ser317) | Cell Signaling | 6887 | Rabbit | WB (1:500) |
| Phospho-S6 Ribosomal Protein (Ser235/236) | Cell Signaling | 4858 | Rabbit | WB (1:500) |
| S6 Ribosomal Protein | Cell Signaling | 2217 | Rabbit | WB (1:1000) |
| LC3B | Cell Signaling | 2275 | Rabbit | WB (1:1000) |
| ATG14 | Cell Signaling | 96752 | Rabbit | WB (1:1000) |
| UVRAG | Cell Signaling | 13115 | Rabbit | WB (1:1000) |
| Rubicon | Cell Signaling | 8465 | Rabbit | WB (1:500) |
| S5A | Cell Signaling | 12441 | Rabbit | WB (1:1000) |
| PI3 Kinase Class III | Cell Signaling | 4263 | Rabbit | WB (1:1000) |
| K48-linkage Specific Polyubiquitin | Cell Signaling | 8081 | Rabbit | WB (1:1000) |

TABLE 1-continued

Antibody details

| Antibody | Company | Cat. Number | Source | Note |
|---|---|---|---|---|
| PERK | Cell Signaling | 5683 | Rabbit | WB (1:1000) |
| LC3 | Abcam | ab48394 | Rabbit | IF (1:100) |
| S5A | Abcam | ab137109 | Rabbit | IP (1:100) |
| UBE3C | Abcam | ab177511 | Rabbit | IP (1:100) |
| Ubiquitin | Abcam | ab7254 | Mouse | WB (1:1000) |
| Calnexin | Abcam | ab22595 | Rabbit | IF (1:100) |
| LC3 | MBL | PM036 | Rabbit | IF-Paraffin (1:100) |
| ATG16L | MBL | PM040 | Rabbit | IF (1:100) |
| UBE3C | GeneTex | GTX117102 | Rabbit | WB (1:1000) |
| DDDK Tag | GeneTex | GTX115043 | Rabbit | WB (1:5000) |
| GAPDH | GeneTex | GTX100118 | Rabbit | WB (1:5000) |
| beta Actin | GeneTex | GTX110564 | Rabbit | WB (1:1000) |
| alpha Tubulin | GeneTex | GTX112141 | Rabbit | WB (1:1000) |
| IRE1 alpha | GeneTex | GTX30005 | Rabbit | WB (1:1000) |
| Phospho-IRE1 alpha (Ser724) | GeneTex | GTX132808 | Rabbit | WB (1:500) |
| RTN3 | GeneTex | GTX131091 | Rabbit | WB (1:1000) |
| PDI | GeneTex | GTX22792 | Mouse | WB (1:1000) |
| Beclin1 | Novus | NB110-87318 | Rabbit | WB (1:1000) |
| AMBRA1 | Novus | 26190002 | Rabbit | WB (1:1000) |
| PI3KR4 | Novus | NBP1-30463 | Rabbit | WB (1:1000) |
| Phospho-ATG13 (Ser318) | Rockland | 600-401-C49 | Rabbit | WB (1:500) |
| ATG13 | Sigma-Aldrich | SAB4200100 | Rabbit | WB (1:1000) |
| HA | Sigma-Aldrich | H3663 | Mouse | WB (1:1000) |
| VPS34 | Invitrogen | 38-2100 | Rabbit | WB (1:500) |
| VPS34 | Echelon Biosciences | Z-R015 | Rabbit | IP (1:100) |
| Ubiquitin (FK2) | Enzo Life Sciences | BML-PW8810-0500 | Mouse | IF (1:100) |
| 6 × His | Takara Bio | 631212 | Mouse | WB (1:5000) |
| ULK1 | Santa Cruz | sc-33182 | Rabbit | WB (1:1000) |
| Phospho-PERK (Thr981) | Santa Cruz | sc-32577 | Rabbit | WB (1:500) |
| GFP | Santa Cruz | sc-9996 | Mouse | WB (1:500) |
| anti-Mouse IgG H&L | Abcam | ab46540 | Rabbit | IP (control IgG) |
| anti-Rabbit IgG HRP | GeneTex | GTX221666-01 | Goat | WB (1:5000) |
| anti-Rabbit IgG HRP | GE Healthcare | NA934 | Donkey | WB (1:5000) |
| anti-Mouse IgG HRP | GE Healthcare | NA931 | Sheep | WB (1:5000) |
| anti-Mouse IgG, Alexa Fluor 568 | Thermo Fisher Scientific | A-11004 | Goat | IF (1:100) |
| anti-Rabbit IgG, Alexa Fluor 568 | Thermo Fisher Scientific | A-11011 | Goat | IF (1:100) |
| anti-Mouse IgG, Alexa Fluor 488 | Thermo Fisher Scientific | A-11001 | Goat | IF (1:100) |
| anti-Rabbit IgG, Alexa Fluor 488 | Thermo Fisher Scientific | A-11008 | Goat | IF (1:100) |

WB: Western blot
IF: Immunofluorescence
IP: Immunoprecipitation

Bafilomycin A1, cycloheximide, 17-(allylamino)-17-demethoxygeldanamycin (17-AAG) and 17-desmethoxy-17-N,N-dimethylaminoethylamino-geldanamycin (17-DMAG) were purchased from Sigma-Aldrich, whereas tunicamycin and thapsigargin were obtained from Cayman Chemical. MG132 was purchased from Calbiochem, and rapalog was obtained from Clontech. Puromycin was obtained from Gibco.

(3) Cell Culture and Transfection

HeLa and 293T cells were obtained from American Type Culture Collection (ATCC). HeLa-GFP-LC3 cells were described previously[1], whereas HeLa-RFP-GFP-LC3 cells were established by transfection of HeLa cells with RFP-GFP-LC3 construct followed by fluorescence-activated cell sorting of a low-expression population.

HeLa and its derived cells were cultured in minimum essential medium (MEM) supplemented with 10% fetal bovine serum (FBS), 1% penicillin/streptomycin (P/S) and 1 mM sodium pyruvate. 293T and 293FT cells were maintained in Dulbecco's modified Eagle's medium (DMEM) containing 10% FBS and 1% P/S. For nutrient starvation, cells were incubated with EBSS (Earle's Balanced Salt Solution; Sigma-Aldrich). U2OS-derived ubiquitin replacement cells were grown in DMEM containing 10% tetracycline/doxycycline-free FBS (Gibco).

Simultaneous knockdown of endogenous ubiquitin and expression of exogenous ubiquitin were performed with the addition of 1 μg/mL doxycycline for 48 h. Transient transfection of 293FT, 293T and its derived cells was performed using the calcium phosphate method, whereas transfection of HeLa cells and HeLa-derived cells were performed with Lipofectamine reagent (Invitrogen).

(4) Lentivirus Production and Infection

293FT cells were transiently transfected with a packaging mixture containing pCMV 48.91 (National RNAi Core Facility, Taiwan) and pMD.G (National RNAi Core Facility, Taiwan), together with a shRNA construct or a pLAS5w.Pneo-based cDNA construct. The medium was changed at 16 h post-transfection and harvested at 20 h to 32 h later. The medium was filtered through a 0.45 μm syringe filter and supplemented with 8 μg/mL polybrene for infection. The infected cells were selected by 2 μg/mL puromycin or 800 μg/mL neomycin.

(5) RNA Interference

Lentivirus-based shRNA constructs were obtained from RNA Technology Platforms and Gene Manipulation Core Facility (Taipei, Taiwan). Pooled UBE3C siRNAs were purchased from Horizon Discovery (Cat #L-007183-00-0005). The target sequences of various shRNAs are listed in the following Table 2.

TABLE 2

Sequences and sources of shRNAs and siRNAs

| shRNA | Target Sequences | Source (Identifier) | SEQ ID NO. |
|---|---|---|---|
| Luciferase shRNA | 5'-CTTCGAAATGTCCGTTCGGTT-3' | National RNAi Core Facility, Academia Sinica, Taiwan | 7 |
| TRABID shRNA #6 | 5'-CCATAGAAGCATACAAGTCAT-3' | National RNAi Core Facility, Academia Sinica, Taiwan | 8 |
| TRABID shRNA #9 | 5'-CAAGGGTGAAATCTTCGTATA-3' | National RNAi Core Facility, Academia Sinica, Taiwan | 9 |
| UBE3C shRNA #2 | 5'-GTCCTATTTCTATCTCCACTT-3' | National RNAi Core Facility, Academia Sinica, Taiwan | 10 |
| UBE3C shRNA #4 | 5'-GCAGATAAGCAAGAAGTTCAA-3' | National RNAi Core Facility, Academia Sinica, Taiwan | 11 |
| UBE3C sgRNA #1 | 5'-CGGCGGCGCTGCCCGCACAT-3' | National RNAi Core Facility, Academia Sinica, Taiwan | 12 |
| UBE3C sgRNA #2 | 5'-CTGGACTCGGGGCCGAGACT-3' | National RNAi Core Facility, Academia Sinica, Taiwan | 13 |
| Pooled UBE3C siRNAs | Not available | Horizon Discovery (Cat #L-007183-00-0005) | — |

(6) Generation of CRISPR Knockout (KO) Cell Line

UBE3C KO cells were established by RNA Technology Platforms and Gene Manipulation Core Facility (Taipei, Taiwan). Briefly, two double-stranded oligonucleotides corresponding to the targeting sequences 5'-CGGCGGCGC TGCCCGCACAT-3' (SEQ ID NO:12) and 5'-CTGGACT CGGGGCCGAGACT-3' (SEQ ID NO:13) located at the exon I of UBE3C gene were cloned to pLAS-CRISPR.Puro (National RNAi Core Facility, Taiwan), which allows the two sgRNAs to be expressed under two independent human U6 promoters. 293T cells were transfected with the resulting plasmid, followed by puromycin selection and single cell colony isolation. The knockout of UBE3C was confirmed by Western blot.

(7) Western Blot

Cells were lysed with radioimmunoprecipitation assay (RIPA) lysis buffer (150 mM NaCl, 20 mM Tris-HCl [pH 7.5], 1% NP40, 0.1% SDS, 1% sodium deoxycholate, 1 μg/mL aprotinin, 10 μg/mL leupeptin, and 1 mM phenylmethylsulfonyl fluoride (PMSF). Lysates containing equal amount of proteins were resolved by SDS-PAGE, and proteins were transferred to polyvinylidene difluoride (PVDF) membranes (Millipore). The membranes were incubated with the blocking buffer containing 1% BSA or 1% to 5% non-fat dry milk in TBST (Tris-buffered saline with 0.1% Tween-20) at room temperature for 30 to 60 min and then incubated with primary antibodies diluted in the blocking buffer at 4° C. overnight.

Next, the membranes were washed three times for 10 min each time with TBST and then incubated with horseradish peroxidase (HRP)-conjugated secondary antibodies diluted in the blocking buffer at room temperature for 1 h. After three times of 10-min wash with TBST, the HRP signal on membranes was detected by Western Lightning Plus-ECL (PerkinElmer Inc.), or Luminata Crecendo (Millipore).

(8) Immunoprecipitation

Cells were lysed with RIPA lysis buffer supplemented with phosphatase inhibitors (1 mM $Na_3VO_4$, 2 mM NaF and 200 μM sodium pyrophosphate). Cell lysates containing equal amount of proteins were incubated with anti-Flag agarose beads (M2; Sigma-Aldrich), anti-V5 agarose beads (Sigma-Aldrich) or GFP-Trap agarose beads (Chromotek) at 4° C. for 2 h.

Alternatively, cells were lysed with NP40 lysis buffer (150 mM NaCl, 50 mM Tris-HCl [pH 7.5], 1% NP40, 1% sodium deoxycholate, 1 μg/mL aprotinin, 10 μg/mL leupeptin, and 1 mM PMSF) supplemented with phosphatase inhibitors.

Cell lysates were pre-cleared with protein A Sepharose (GE Healthcare) at 4° C. for 1 h and incubated with various antibodies at 4° C. overnight, followed by 2 h of incubation with protein A Sepharose at 4° C. After washing the beads with a lysis buffer for three times, proteins bound on beads were analyzed by Western blot.

(9) Immunofluorescence

Cells seeded on coverslips were washed for three times with phosphate buffered saline (PBS) and fixed with 4% formaldehyde at room temperature for 20 min. After three times of wash with PBS, cells were permeabilized with ice-cold methanol for 10 min and then washed three times with PBS. Cells were blocked in PBS containing 1% BSA and 10% goat serum at room temperature for 1 h and incubated with primary antibody diluted in the blocking buffer at 4° C. overnight. Next, cells were washed three times with PBS, rinsed once with the blocking buffer, and then incubated with a fluorescent dye-conjugated secondary antibody (Life Technologies) together with 4',6-diamidino-2-phenylindole (DAPI) (1 µg/mL) (Sigma-Aldrich) at room temperature for 1 h. Cells were washed three times for 10 min each time with PBS and mounted with a mounting medium (Dako).

(10) Confocal Microscopy and Image Analysis

Cells receiving immunofluorescence staining or cells expressing fluorescent proteins were fixed with 4% formaldehyde at room temperature for 20 min and examined by a confocal microscope (LSM510; Carl Zeiss MicroImaging Inc.) equipped with a 63×/1.40 oil objective lens (Plan-Apochromat, Zeiss). In some cases, cells were examined by a confocal microscope (Olympus FV3000) equipped with a 60×/1.40 oil objective lens (Olympus Objective Lens, PlanApo N). To quantify colocalization of puncta, images were thresholded for particle identification using the Analyze Particles function in Image J. The raw intensities of regions containing both puncta signals were calculated through the Measure function of Image J. To quantify the area with a positive signal, images were thresholded, defined and analyzed by Image J.

(11) shRNA Screening and High-Throughput Image Analysis

HeLa cells stably expressing Dendra2-LC3 were seeded at a density of 1500 cells/well on 96-well plates (Corning 3603). After cultured for 24 h at 37° C., cells were incubated with the medium containing 8 µg/mL polybrene and lentivirus carrying each of the 403 DUB shRNAs corresponding to 91 DUB s (obtained from RNA Technology Platforms and Gene Manipulation Core Facility) with a multiplicity of infection of 2. The infection medium was replaced with DMEM containing 10% FBS, 1% P/S, and 3 µg/mL puromycin on the next day. At 72 h post-antibiotic selection, stable cell lines were cultured in starvation medium (EBSS) for 3 h. Cells were fixed with 4% paraformaldehyde for 15 min and stained with 1 µg/mL DAPI for 10 min at room temperature. LC3 signal was examined using Cellomics ArrayScan HT fluorescence microscope (Thermo Scientific) with a 20× objective lens. Images were acquired by a Cellomics Spot Detector Bioapplication program and analyzed by Cellomics vHCS:View software.

(12) In Vitro Binding

For analyzing the in vitro interaction of VPS34 with UBE3C, recombinant HA-UBE3C was purified from baculovirus with anti-HA agarose (Sigma-Aldrich) and eluted with an HA peptide. Flag-VPS34 purified from baculovirus was immobilized on anti-Flag M2 beads and incubated with purified HA-UBE3C in the binding buffer (50 mM Tris [pH 7.5], 150 mM NaCl and 1% NP-40) for 30 min. For testing the in vitro binding between TRABID and VPS34, His-VPS34 was purified from bacteria using Ni Sepharose and eluted by imidazole. V5-TRABID purified from 293T cells was immobilized on V5 beads (Sigma-Aldrich) and incubated with purified His-VPS34 in the binding buffer for 30 min. In both cases, the beads were washed with the binding buffer, and the bound proteins were analyzed by Western blot.

(13) In Vivo Ubiquitination and Deubiquitination Assays

Cells transfected with expression construct for His-ubiquitin or its mutant together with other expression constructs were treated with MG132 for 16 h and lysed under denaturing conditions by buffer A (6 M guanidine-hydrochloride, 0.1 M $Na_2HPO_4/NaH_2PO_4$ [pH 8.0], and 10 mM imidazole). Lysates were incubated with Ni-NTA agarose for 2 h at 4° C. The beads were washed three times with buffer A/TI [1 vol buffer A: 3 vol buffer TI (25 mM Tris-HCl, pH 6.8 and 20 mM imidazole)] and five times with buffer TI, followed by Western blot analysis.

Alternatively, cells transfected with Flag-VPS34 together with other constructs were lysed with RIPA lysis buffer. Lysates were subjected to immunoprecipitation with anti-Flag M2 beads, followed by Western blot analysis. In all experiments, the equal expression of His-ubiquitin or its variants was checked by Western blot.

(14) In Vitro Ubiquitination and Deubiquitination Assays

In vitro ubiquitination assay was performed in a 20 µL reaction mixture containing 25 mM HEPES (pH 7.5), 200 mM NaCl, 5 mM $MgCl_2$, 2.5 mM adenosine triphosphate (ATP), 50 µM ubiquitin, 200 nM UBE1 (E1), 500 nM UbcH5a (E2), 2 µM UBE3C (E3) (full length, purified from baculovirus) or SUMO-UBE3C$^{HECT}$ (residues 693 to 1083, purified from E. coli), together with or without 500 ng Flag-VPS34 at 37° C. for 40 to 90 min. For in vitro deubiquitination assay, 10 µL ubiquitinated Flag-VPS34 taken from in vitro ubiquitination reaction mixture was incubated with 2 µM TRABID (Boston Biochem; E-560) at 37° C. for 4 h in 30 µL reaction mixture containing 50 mM Tris (pH 7.6), 50 mM NaCl, and 10 mM dithiothreitol (DTT).

(15) Lb$^{pro}$*Purification and Treatment

His-tagged Lb$^{pro}$ (29 to 184 a.a., UniProt ID: P05161) was synthesized and subcloned to pRSF-duet expression vector by GenScript (Piscataway, NJ). Lb$^{pro}$* (L102W) was generated by, site-directed mutagenesis to effectively cleave ubiquitin[3]. Lb$^{pro}$* plasmid was transformed into pLys bacteria and the transformants were cultured in LB medium at 37° C. When the optical density (600 nm) was reached to 0.8, 0.6 mM isopropyl β-d-1-thiogalactopyranoside (IPTG) was added to induce Lb$^{pro}$* expression Lb$^{pro}$* was purified by nickel affinity chromatography followed by size exclusion chromatography using an SD200 16/60 increase column on an Akta. FPLC (GE healthcare, Pittsburgh, PA). Fractions containing Lb$^{pro}$* were collected, concentrated and flash-frozen by liquid nitrogen. For Lb$^{pro}$* treatment, 10 mM EDTA was added into the in vitro ubiquitination reaction mixture and incubated at 37° C. for 10 min. The mixture was treated with 50 µM Lb$^{pro}$* in a buffer containing 50 r M Tris (pH 8.0) and 10 nM DTT and incubated at 37° C. overnight. For intact Mass Spectrometry analysis, the mixture sequentially passed through 50 kDa and 3 kDa Amicon Ultra-0.5 Centrifugal Filters to remove the high molecular weight substances.

(16) Intact Mass Spectrometry for Molecular Weight Determination

The protein sample was diluted with 50% acetonitrile and 1% formic acid. An aliquot corresponding to one pmol of the pure protein was injected via the LockSpray Exact Mass Ionization Source (Waters, Milford, MA) with a syringe pump (Harvard Apparatus, MA) and held a flow rate of 3 µL/min throughout the analysis. The mass of intact proteins was determined using Waters Synapt G2 HDMS mass spectrometer (Waters, Milford, MA). The acquired spectra were deconvoluted to a single-charge state using MaxEnt1 algorithm of the MassLynx 4.1 software (Waters, Milford, MA).

(17) LC-MS/MS and Bel-Free Quantification

The Lb$^{pro}$*-treated reaction was separated by SDS-PAGE and stained with SYPRO Ruby Protein Gel Stain (Invitrogen). The band corresponding to the molecular weight of monoubiquitin was excised for in-gel digestion with Asp-N at 37° C. overnight. NanoLC-nanoESI-MS/MS analysis was performed on a nanoAcquity system (Waters, Milford, MA) connected to the LTQ Orbitrap Velos hybrid mass spectrometer (Thermo Electron, Bremen, Germany) equipped with a Nanospray Flex interface. Peptide mixtures were loaded onto a 75 µm ID, 25 cm length C18 BEH column (Waters, Milford, MA) packed with 1.7 µm particles with a pore width of 130 Å, and were separated using a segmented gradient in 90 min from 5% to 35% solvent B (acetonitrile with 0.1% formic acid) at a flow rate of 300 nL/min and a column temperature of 35° C. Solvent A was 0.1% formic acid in water.

The mass spectrometer was operated in the data-dependent mode. Briefly, survey of full scan MS spectra was acquired in the orbitrap (m/z 350-1600) with the resolution set to 60K at m/z 400 and automatic gain control (AGC) target at $10^6$. The 10 most intense ions were sequentially isolated for HCD MS/MS fragmentation and detection in the orbitrap with previously selected ions dynamically excluded for 60 s. For MS/MS, we used a resolution of 7500, an isolation window of 2 m/z, and a target value of 50,000 ions, with maximum accumulation times of 250 ms. Fragmentation was performed with normalized collision energy of 35% and activation time of 0.1 ms. Ions with singly and unrecognized charge state were excluded.

All data generated were searched against the Swiss-Prot Human database, and (561,911 entries total) database using the Mascot search engine (v.2.7.0; Matrix Science, Boston, MA, USA) through Proteome Discoverer (v. 2.4.1.15; Thermo Scientific, Waltham, MA, USA). Search criteria used were trypsin digestion, variable modifications set as carbamidomethyl (C), oxidation (M), ubiquitination (K) allowing up to 2 missed cleavages, mass accuracy of 10 ppm for the parent ion and 0.02 Da for the fragment ions. The false discovery rate (FDR) was set to 1% for peptide identifications. Peptide sequence assignments contained in Mascot search results were validated by manual confirmation from raw MS/MS data. For label-free quantification, intensities of precursor ions were extracted using Minora Feature Detector node in Proteome Discoverer with a 2 ppm mass precision and 2 min retention time shift (aligning the LC/MS peaks for mapping to the isotope pattern and retention time).

(8) Chemical-Induced Dimerization

Cells were transiently transfected with Flag-FKBP12-UBE3C together with V5-VPS34 or V5-FRB-VPS34. Dimerization between the FRB- and FKBP12-based fusion proteins was induced by adding 500 nM rapalog (Clontech) to the culture medium.

(19) Protein Aggregate Clearance Assay

To evaluate the clearance of ubiquitin aggregates, puromycin-treated cells were washed once with DMEM, cultured in puromycin-free medium for 4 h and examined by confocal microscopy. Alternatively, the clearance of protein aggregates was analyzed using PROTEOSTAT Aggresome Detection Kit (Enzo Life Sciences). Briefly, cells were fixed, permeabilized and incubated with PROTEOSTAT dye at room temperature for 30 min. Fluorescent signal was analyzed by a flow cytometer (Beckman CytoFLEX) using the 488 nm laser.

(20) Apoptosis Assay

Cells seeded at a density of $8 \times 10^6$ cells/well in a 6-well plate were treated with puromycin or tunicamycin together with rapalog for 3 h or 6 h, respectively. Cells were harvested, and DNA fragmentation was measured by Cell Death ELISA Kit (Roche) according to manufacturer's instructions.

(21) Mouse NAFLD Model

Eight-week-old male C57BL/6J mice purchased from the LASCO CO, Taiwan were fed with a freely available sterilized high-fat diet (DYET #100244, Dyets, Inc.) having components containing 41.4% of the total calories from fat, or with a normal chow diet. For investigating the role of TRABID-dependent autophagy regulation in liver, mice were retro-orbitally injected with recombinant adeno-associated virus (rAA), i.e., control rAAV8 or rAAV8-TRABID ($1 \times 10^{11}$ vg per mouse, generated by AAV Core Facility in Academia Sinica) and then sacrificed at 4 weeks after injection. All animal protocols were approved by Institutional Animal Care and Use Committee, Academia Sinica.

(22) Histology Analysis

Mouse livers were collected, fixed with 10% formalin buffered with phosphate at 4° C. overnight, washed and then incubated with 70% ethanol for another overnight. After processing, tissues were embedded in paraffin, sectioned and stained with H&E with a standard protocol.

(23) Immunofluorescence Staining of Paraffin-Embedded Tissues

Paraffin-embedded tissue sections mounted on slides were deparaffinized at 65° C. for 30 min, incubated in three changes of xylene for 5 min each and rehydrated through graded concentrations of ethanol (100%, 100%, 95%, 85% and 75% for 1 min each). After washed twice with ddH$_2$O for 5 min each, sections were heated in citrate buffer (Scytek) using a BioSB Tinto Retrieve Pressure Cooker and then cooled for 15 min. Next, sections were permeabilized with 0.2% Triton X-100 in PBS for 10 min, washed three times with PBS for 3 min each, blocked with PBS containing 10% goat serum and 1% BSA for 30 min, and incubated with primary antibodies at 4° C. overnight, After washed three times with PBS for 5 min, slides were incubated with HRP-conjugated secondary antibody (Invitrogen) at room temperature for 30 min. The sections were mounted by a mounting medium with DAPI (Santa Cruz).

(24) Oil Red O Staining

Mouse liver tissues were fixed with ice-cold 4% paraformaldehyde in PBS (Santa Cruz) at 4° C. for overnight. Livers were then incubated with 30% sucrose solution in PBS at 4° C. overnight. After processed and embedded by optimal cutting temperature (OCT), liver tissues were stained with Oil Red O solution and washed with 50% isopropanol and deionized water. Liver sections were counterstained with hematoxylin. The sections were photographed by Pannoramic 250 FLASH II Slide Scanner and analyzed by 3DHISTECH's Slide Converter. Quantification of the Oil Red O positive area was performed with the Histoquant module in 3DHISTECH Pannoramic Viewer. One area was selected from the slide for each mouse liver, and the percentage of area showing a positive signal was calculated.

(25) Serum Biochemical Analysis

Blood samples were obtained from facial vein or cardiac puncture before sacrifice. Following serum collection by centrifugation, AST and ALT levels were measured by DRI-CHEM 3500s (FUJIFILM).

(26) Hepatic Triglyceride Level Analysis

Triglyceride in the liver was extracted by homogenizing the tissue with a 1 mL solution of 1:2 methanol/chloroform (v/v), followed by sonication at 37° C. for 30 min and shaking at 4° C. overnight. After centrifugation to pellet down the debris, 0.25 mL of chloroform and 0.25 mL of water were added to the liquid material and vortexed for 30 min. The lower organic phase was transferred to a new tube, and the solvent was evaporated using a speed vacuum apparatus. The pellet was resuspended with TR0100 reagent (Serum Triglyceride Determination Kit, Sigma), and then incubated for 10 min at room temperature, followed by absorbance measurement at 540 nm.

(27) Statistical Analysis

The unpaired two-tail Student's t-test was used to compare between two groups, and the one-way or two-way ANOVA with Turkey's post hoc test was used for multi-group comparison. All statistical analyses were conducted at a significance level of $p<0.05$.

Example 1: TRABID Promotes Autophagosome Formation

To elucidate the crosstalk between ubiquitin-proteasome system (UPS) and autophagy, an unbiased loss-of-function screen was performed to individually knockdown each of the 91 deubiquitinases (DUB s) for testing their influence on autophagy. To this end, HeLa cells stably expressing Dendra-LC3 were transduced with lentivirus carrying the shRNAs, starved, and assayed for the number of Dendra-LC3 puncta using a high-content fluorescent analysis.

Figures 1B, 1C:
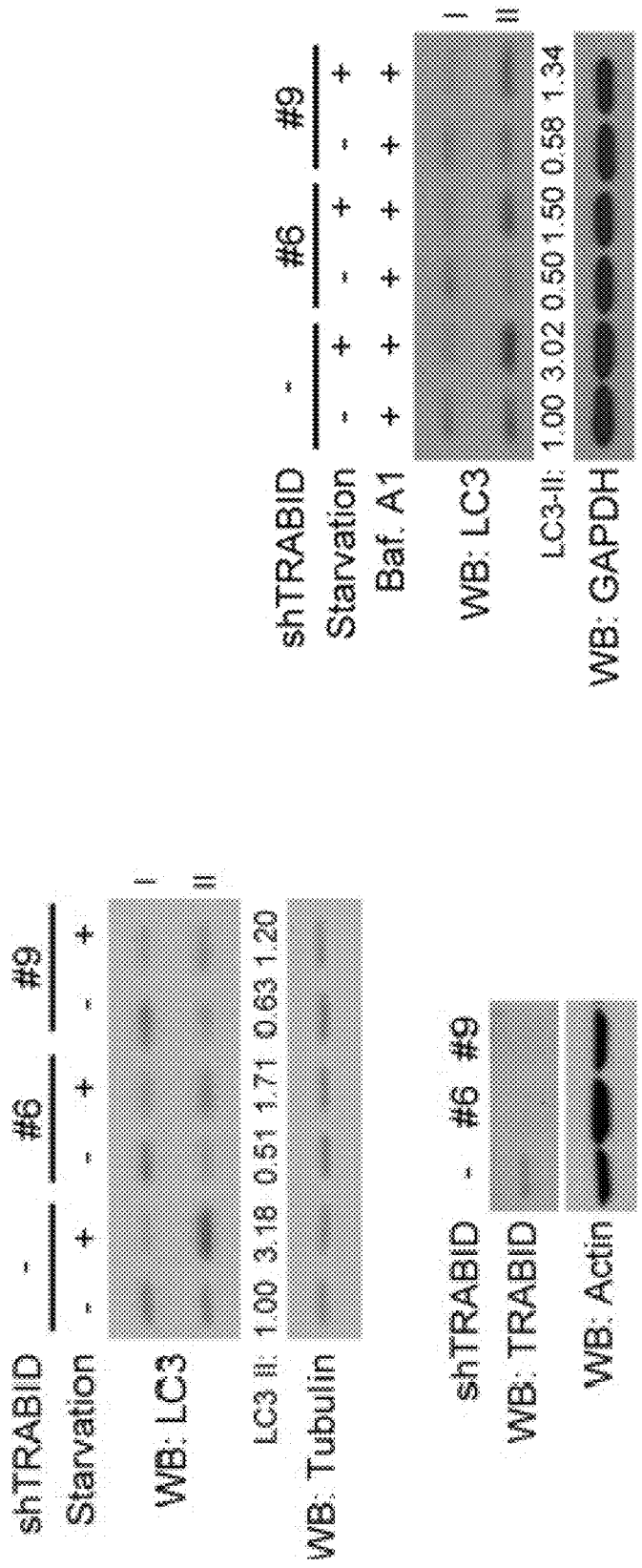
Figure 1D:
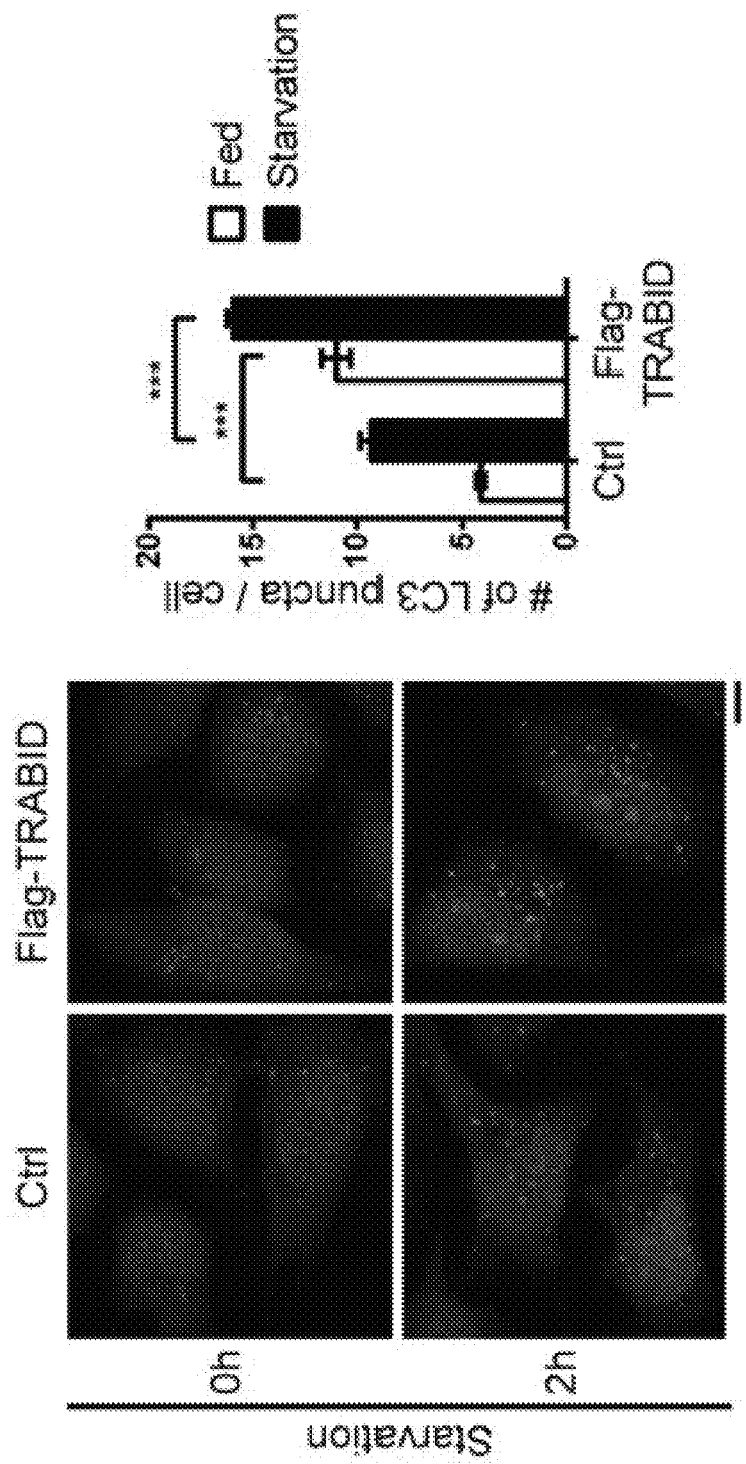
Figure 1E:
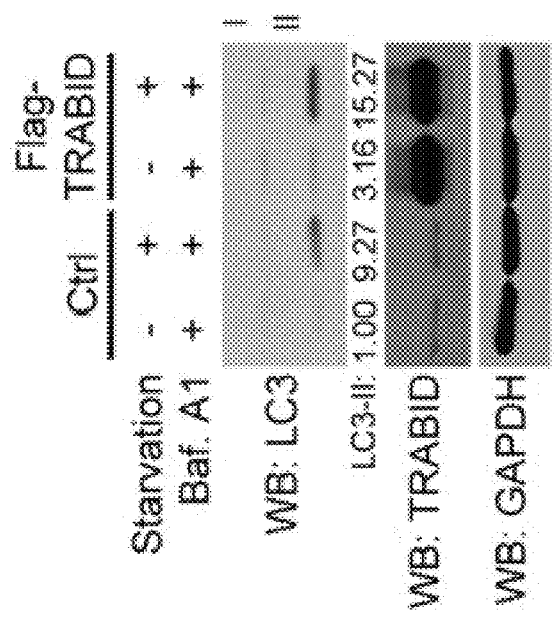

It was found that TRABID knockdown reduced autophagosome numbers and LC3 lipidation in fed and starved cells (FIGS. 1A and 1B). Furthermore, in cells treated with bafilomycin A1 to block autophagic turnover, TRABID knockdown still reduced LC3 lipidation (FIG. 1C), indicating a promoting role of TRABID in autophagosome formation. Also, TRABID overexpression increased autophagosome number in both fed and starved cells (FIG. 1D). Accordingly, LC3 lipidation was also enhanced by TRABID overexpression in fed and starved cells treated with bafilomycin A1 (FIG. 1E). These findings collectively identified TRABID as a positive regulator of autophagosome biogenesis.

Example 2: TRABID Reduces VPS34 K29/K48 Ubiquitination to Stabilize VPS34

Figures 1F, 1G:
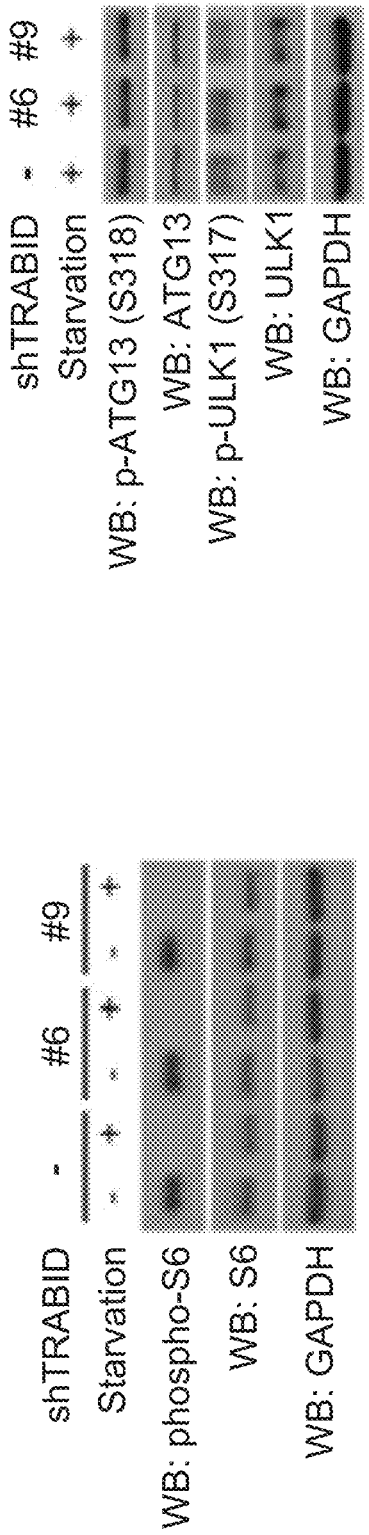
Figure 1H:
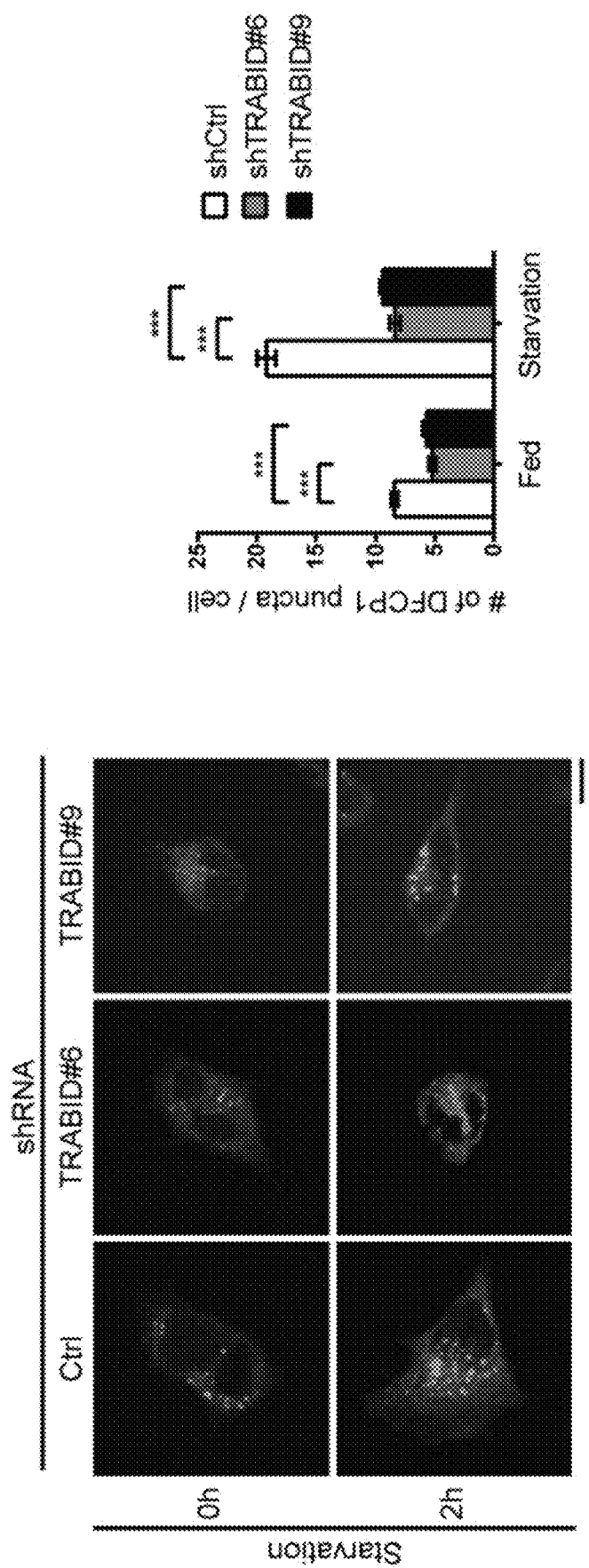
Figure 1I:
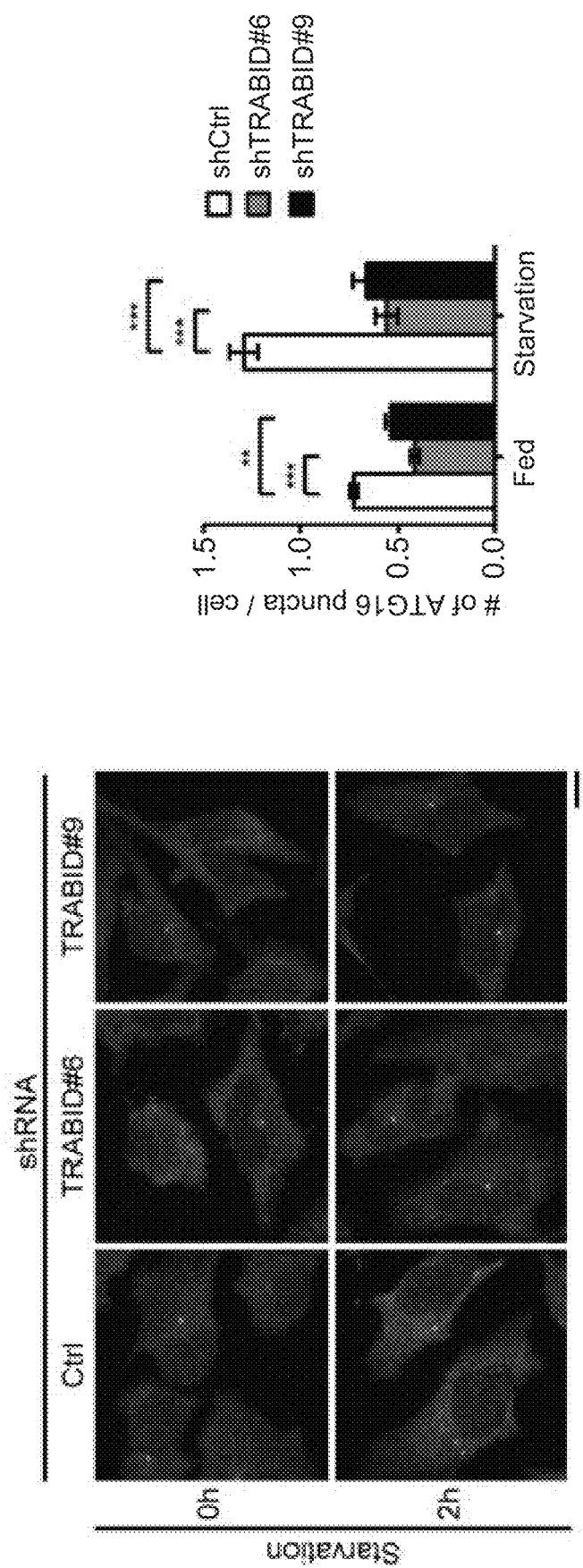
Figure 1J:
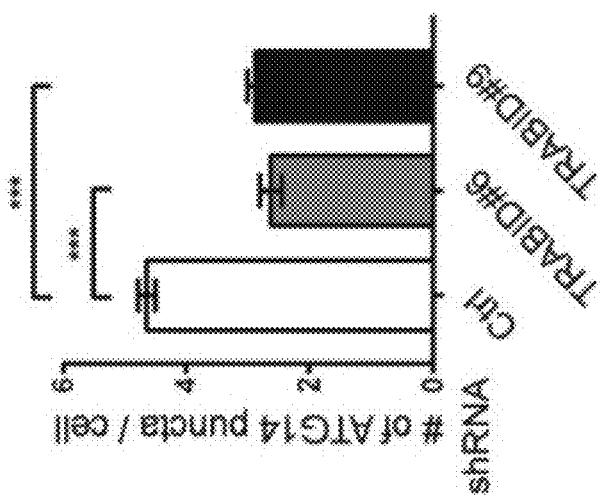
Figure 1J:
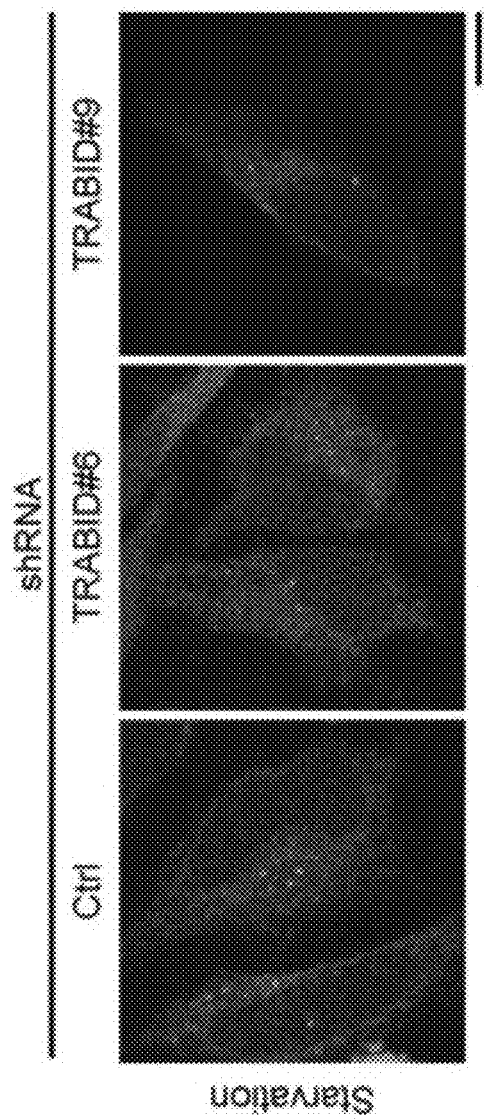

TRABID knockdown did not affect mTOR, AMPK and ULK1 activities, as monitored by phosphorylation of ribosomal S6 protein, phosphorylation of ULK1 S317 residue and phosphorylation of ATG13 S318 residue, respectively (FIGS. 1F and 1G). However, TRABID knockdown diminished DFCP1 puncta, ATG16 puncta, and ATG14 puncta (FIGS. 1H to 1J). These findings suggest an impact of TRABID on the class III PI3-kinase.

Figure 2B:
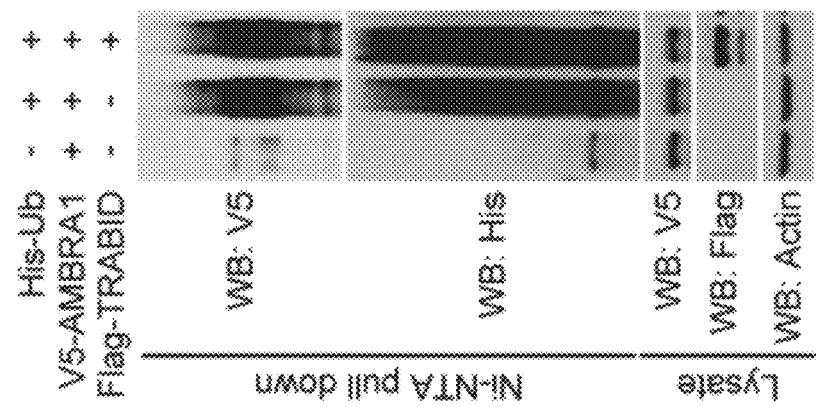
Figure 2A:
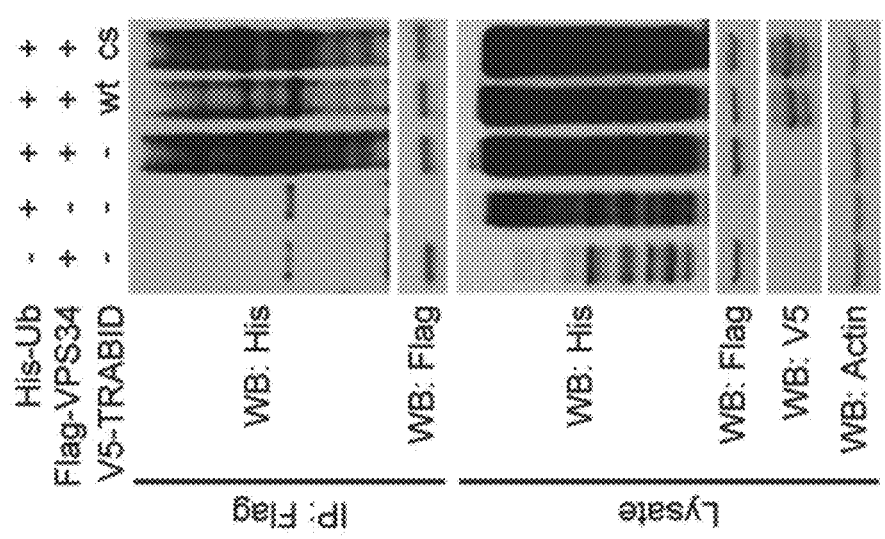
FIGS. 2A to 2T are graphs illustrating that TRABID diminishes the K29/K48 ubiquitination on VPS34 and promotes autophagosome maturation, but cannot affect the ubiquitination of AMBRA1, Beclin1, ATG14 and UVRAG.

As shown in FIGS. 2A to 2E, among the subunits of VPS34 complex, TRABID overexpression reduced the ubiquitination level of VPS34, but not AMBRA1, Beclin1, ATG14 and UVRAG. However, TRABID catalytically dead mutant (cs) failed to affect VPS34 ubiquitination (FIG. 2A). It was then determined which kind of ubiquitin chain that was removed by TRABID.

Figure 2F:
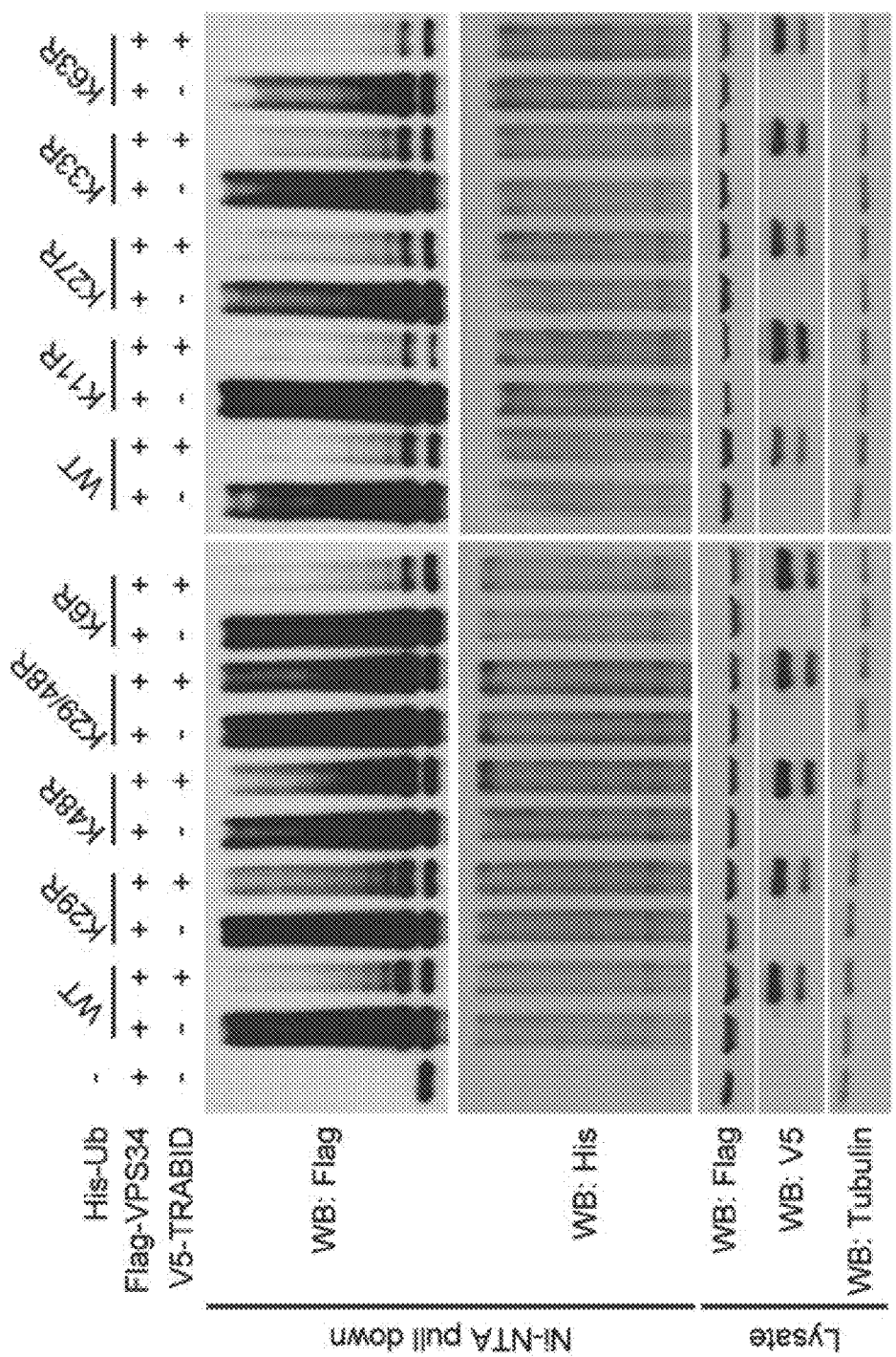
FIGS. 2F and 2G show the analysis results of the ubiquitin chain types on VPS34 that are affected by TRABID. The ubiquitinated proteins are pulled down by Ni-NTA agarose under denaturing conditions from 293T cells transfected with indicated constructs and analyzed by Western blot with indicated antibodies. The amounts of different ubiquitin constructs used for transfection are adjusted to allow an equal level of VPS34 ubiquitination in cells without TRABID transfection.
Figure 2H:
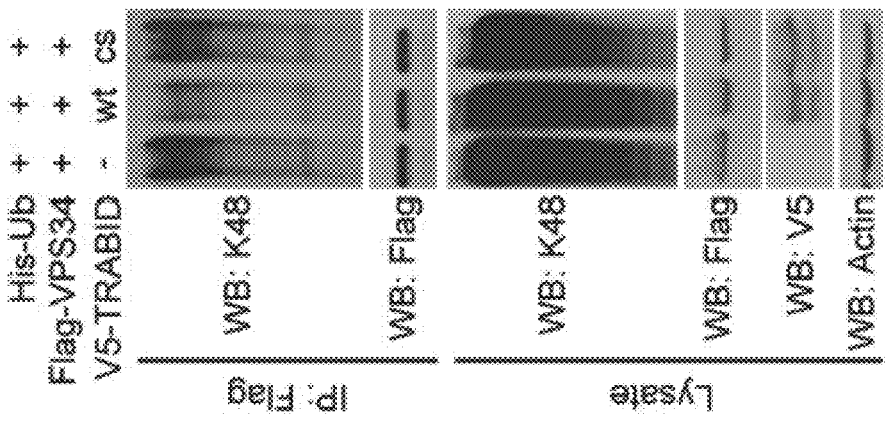
Figure 2G:
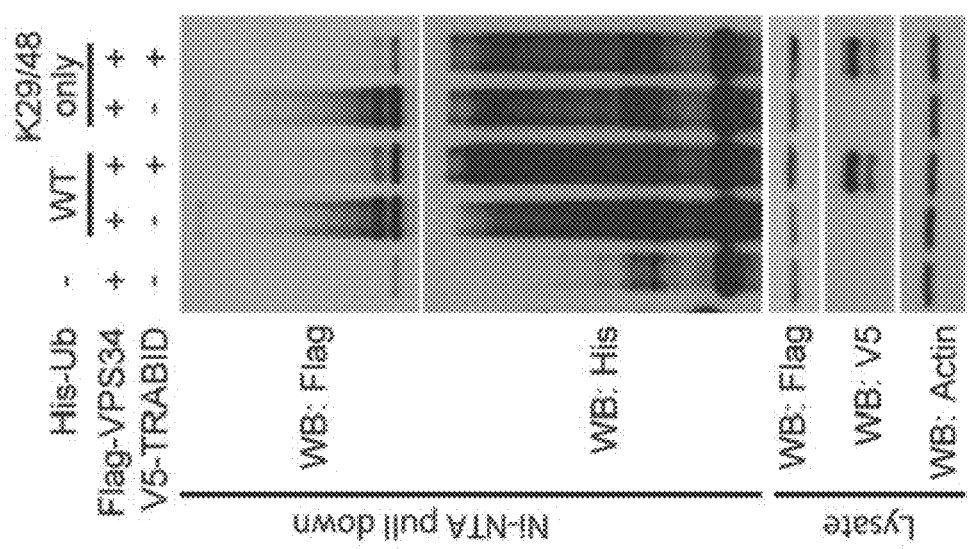

By using each ubiquitin KR mutant, it was unexpectedly found that both K29R and K48R mutants attenuated TRABID-induced VPS34 deubiquitination, whereas K29R/K48R double mutant completely abrogated this deubiquitination (FIG. 2F). Also, the K29/K48-only ubiquitin could confer TRABID-induced VPS34 deubiquitination even more efficiently than wild type ubiquitin (FIG. 2G). The ability of TRABID, but not its cs mutant, to reduce the K48 ubiquitin chain on VPS34 was further validated using a K48 chain-specific antibody (FIG. 2H). These data provided evidence for the ability of TRABID to remove K29- and K48-linked ubiquitin chains from VPS34.

Figures 2I, 2J:
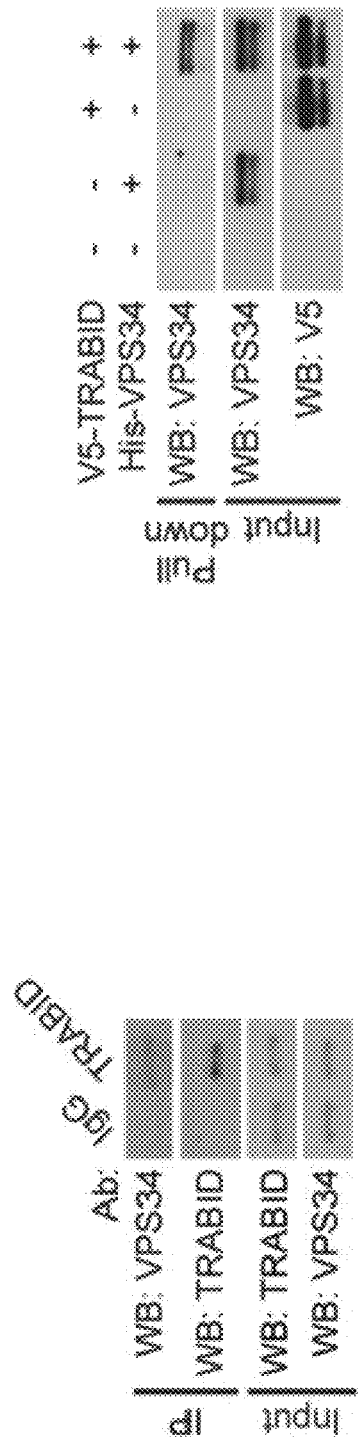
FIG. 2I shows the results of immunoprecipitation analysis of the interaction between endogenous TRABID and endogenous VPS34 in 293T cells.
FIG. 2J shows in vitro interaction of purified TRABID bound on V5-beads with purified His-VPS34.
Figures 2K, 2L:
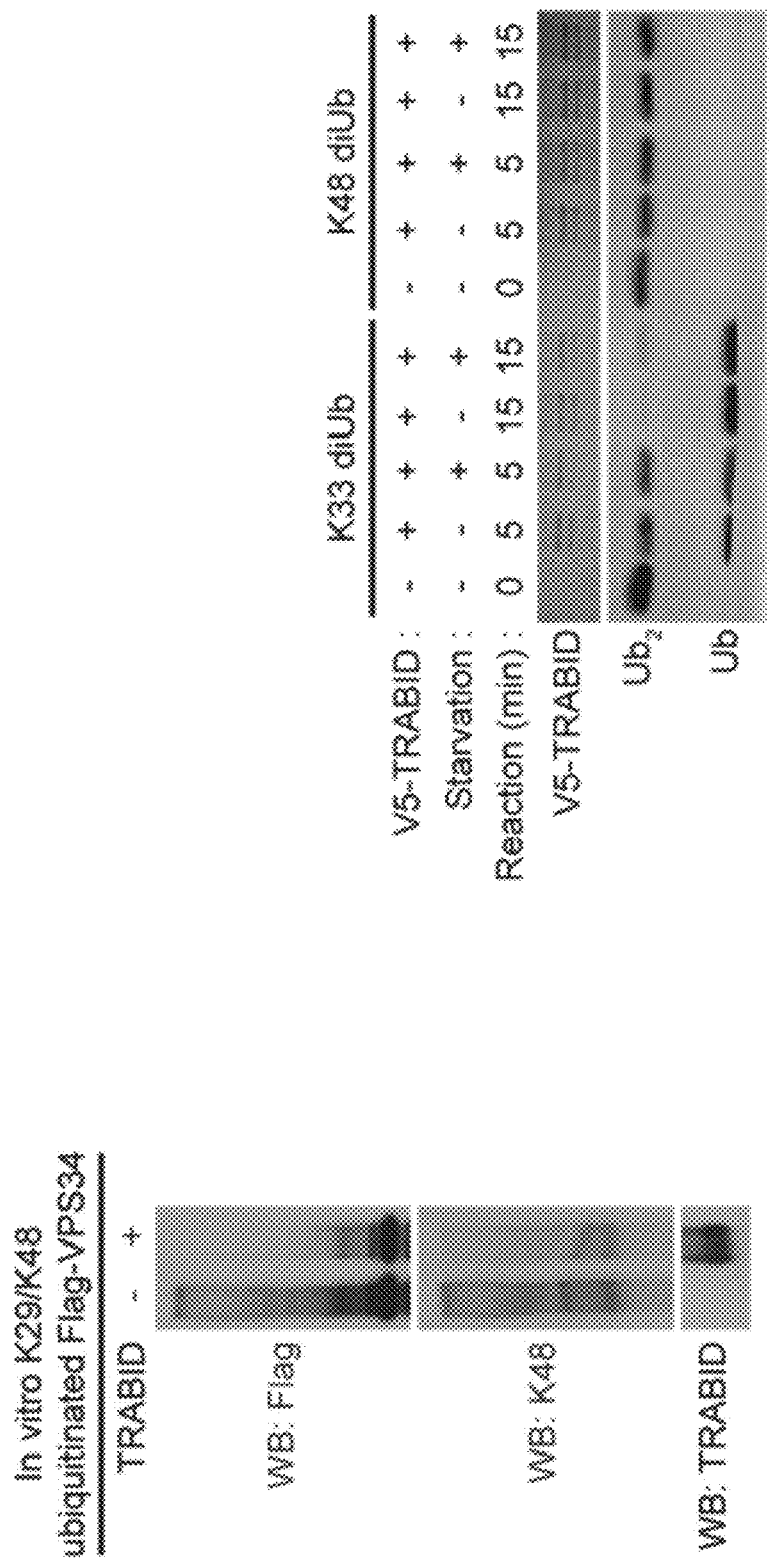
FIG. 2K shows the result of the in vitro deubiquitination assay, wherein Flag-VPS34 is previously ubiquitinated in vitro by UBE3C and then incubated with or without purified TRABID. The reaction mixture was analyzed by Western blot.
FIG. 2L shows the in vitro disassembly of K33-linked and K48-linked diubiquitin chain by TRABID purified from fed or starved cells. The reaction is proceeded for indicated time period and then analyzed by SDS-PAGE and Coomassie blue staining.

Consistent with the deubiquitination effect of TRABID on VPS34, endogenous TRABID interacted with endogenous VPS34 (FIG. 2I). Furthermore, baculovirally purified recombinant TRABID and VPS34 interacted in vitro (FIG. 2J). Using VPS34 that was ubiquitinated in vitro by an E3 ligase known to generate K29/K48 heterotypic ubiquitin chain, it was found that purified TRABID was capable of reducing the total and K48 ubiquitin linkages from this VPS34 in vitro (FIG. 2K). However, TRABID purified from fed or starved cells could not hydrolyze the K48-linked diubiquitin (FIG. 2L).

These findings supported the formation of K29/K48 heterotypic chain on VPS34, so that the cleavage of proximal K29 linkages would lead to the removal of distal K48 linkages from the substrate. Together, these studies identified VPS34 as a substrate of TRABID. TRABID antagonized VPS34 K29/K48 heterotypic ubiquitination even without directly hydrolyzing the K48 ubiquitin chain.

Figure 2M:
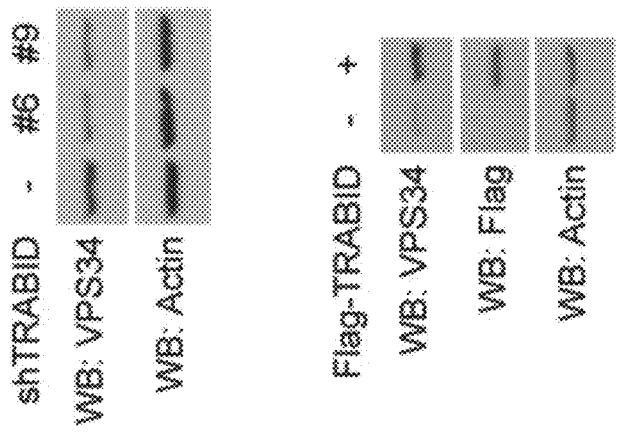
FIG. 2M shows the results of Western blot analysis of VPS34 expression in HeLa cells stably expressing TRABID shRNA or TRABID construct.
Figures 2N, 2O:
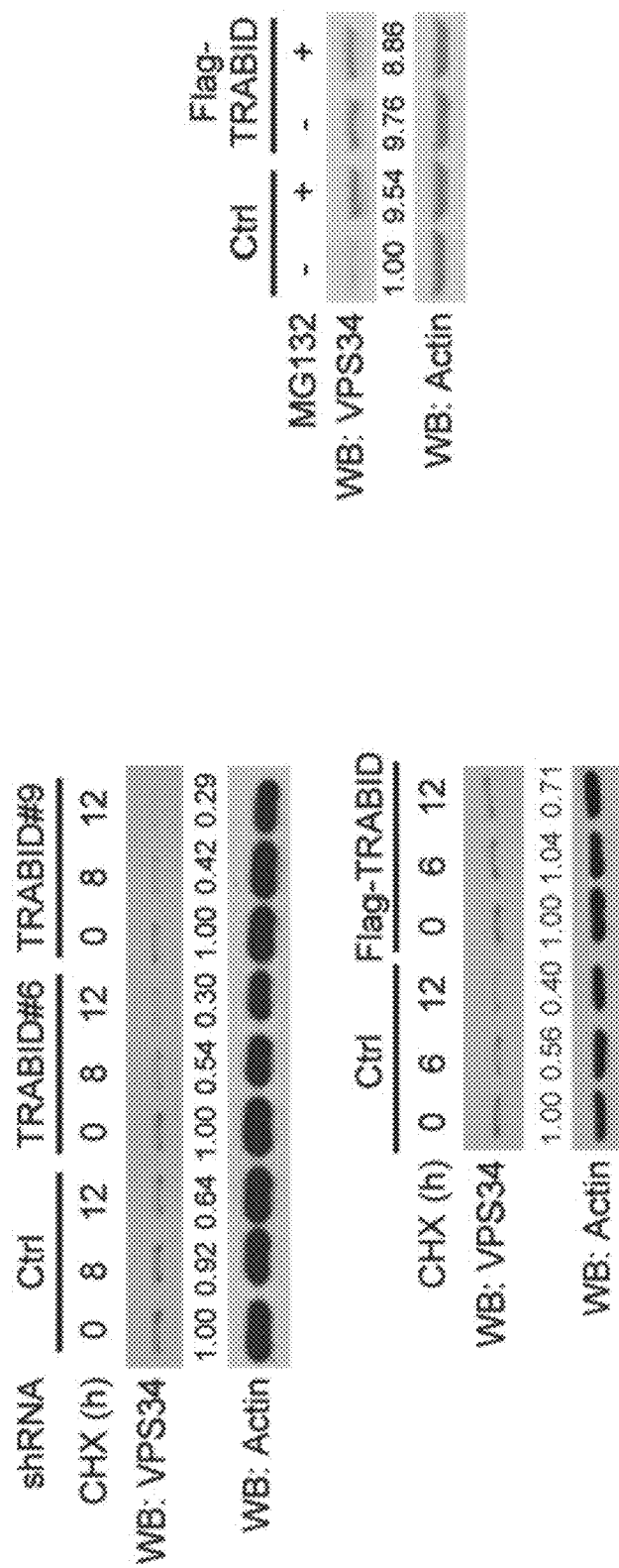
FIGS. 2N and 2O show the results of Western blot analysis of VPS34 in indicated HeLa-derived cells treated with cycloheximide (CHX) for indicated time points or with MG132 for 16 h.

As to the functional consequence of TRABID-mediated VPS34 deubiquitination, FIGS. 2M and 2N showed that TRABID knockdown decreased VPS34 protein abundance and half-life, whereas TRABID overexpression enhanced VPS34 expression and stability. Furthermore, the proteasome inhibitor MG132 increased VPS34 expression in control cells but not TRABID overexpressing cells (FIG. 2O). Collectively, these findings identified a role of TRABID in VPS34 K29/K48 deubiquitination and stabilization.

Figures 2P, 2Q:
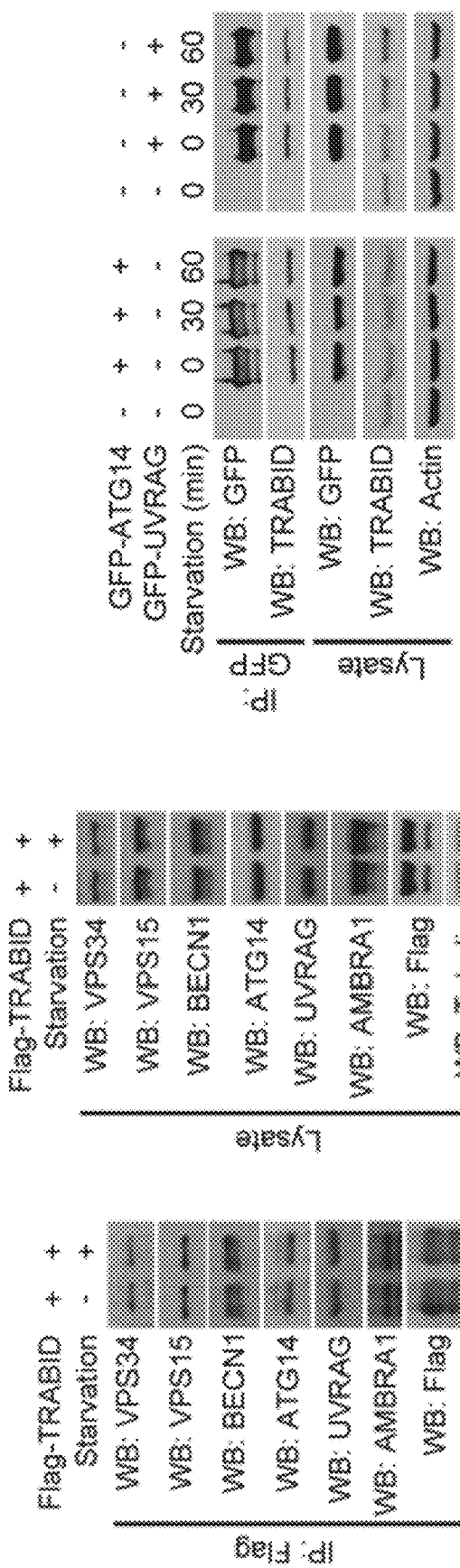
FIG. 2P shows the results of immunoprecipitation analysis of the interaction between Flag-TRABID and various subunits of the VPS34 complexes I and II in 293T cells transfected with Flag-TRABID and cultured in fed or starvation conditions for 2 h.
FIG. 2Q shows the results of immunoprecipitation analysis of the interaction between TRABID and ATG14 or UVRAG in 293T cells transfected with indicated constructs and cultured in a full medium or starved for indicated time points.
Figure 2R:
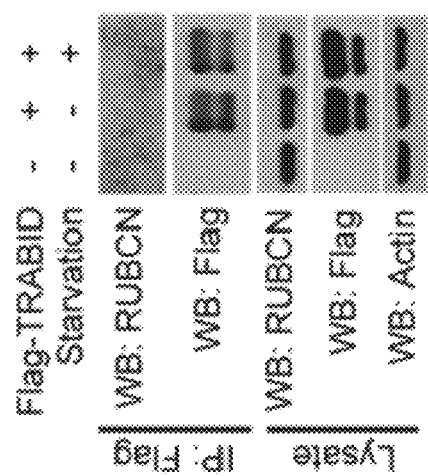
FIG. 2R shows the results of immunoprecipitation analysis of the interaction between Flag-TRABID and Rubicon in 293T cells transfected with Flag-TRABID and cultured in fed or starvation for 2 h.

Example 3: TRABID Associates with VPS34 Complex I and Complex II and Promotes Autophagosome Maturation VPS34 is present in different complexes, wherein the complex I and complex II contain specific subunit ATG14 and UVRAG and are responsible for autophagosome formation and maturation, respectively. Immunoprecipitation analysis revealed the association of TRABID with both ATG14 and UVRAG, along with the common subunits of VPS34 complex, in fed and starved cells (FIG. 2P). Furthermore, GFP-ATG14 and GFP-UVRAG interacted with endogenous TRABID in transfected cells, and these associations were not affected by starvation (FIG. 2Q). However, no association of TRABID with Rubicon, which forms a VPS34 complex with autophagy-inhibitory function, could be detected (FIG. 2R).

Figure 2S:
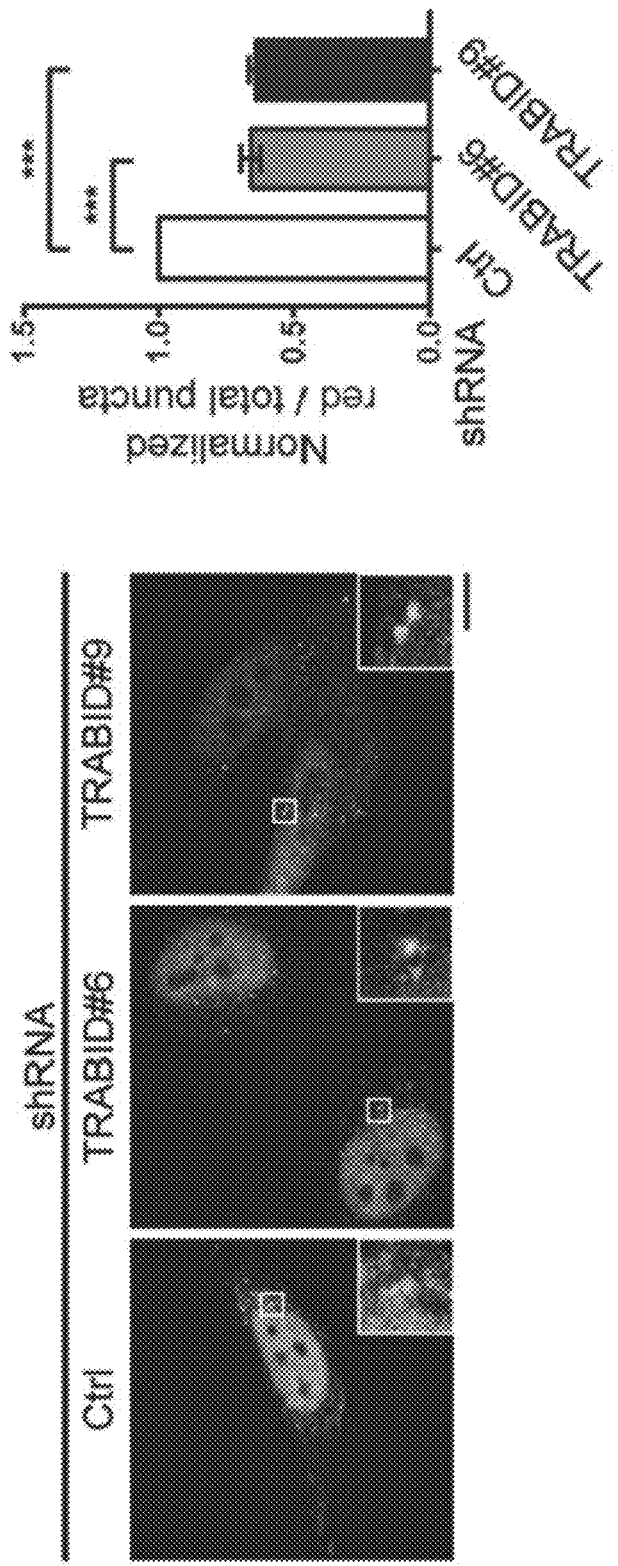
Figure 2T:
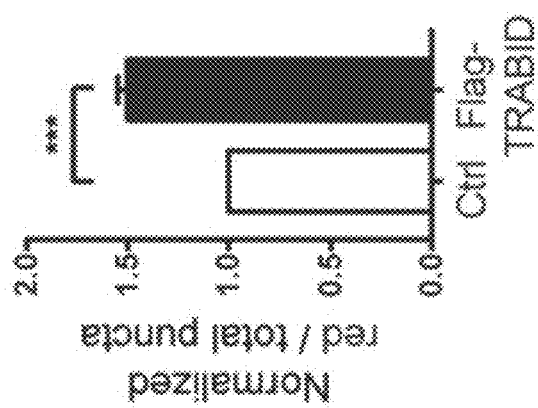
Figure 2T:
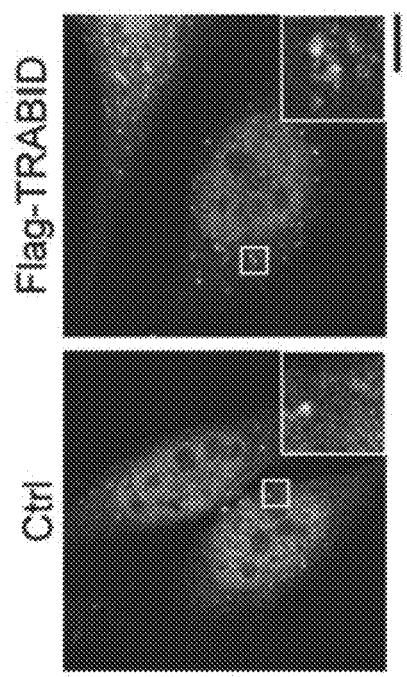

These findings indicated that TRABID was recruited to VPS34 complexes I and II. The former was expected by TRABID's function to potentiate autophagosome biogenesis, whereas the latter suggested its role in autophagosome maturation. As shown in FIGS. 2S and 2T, TRABID knockdown decreased autophagosome maturation into autolysosome, whereas TRABID overexpression enhanced it. Thus, in addition to autophagosome formation, TRABID promotes autophagosome maturation.

Example 4: UBE3C Assembles an K29/K48 Branched Ubiquitin Chain on VPS34

Figures 3A, 3B:
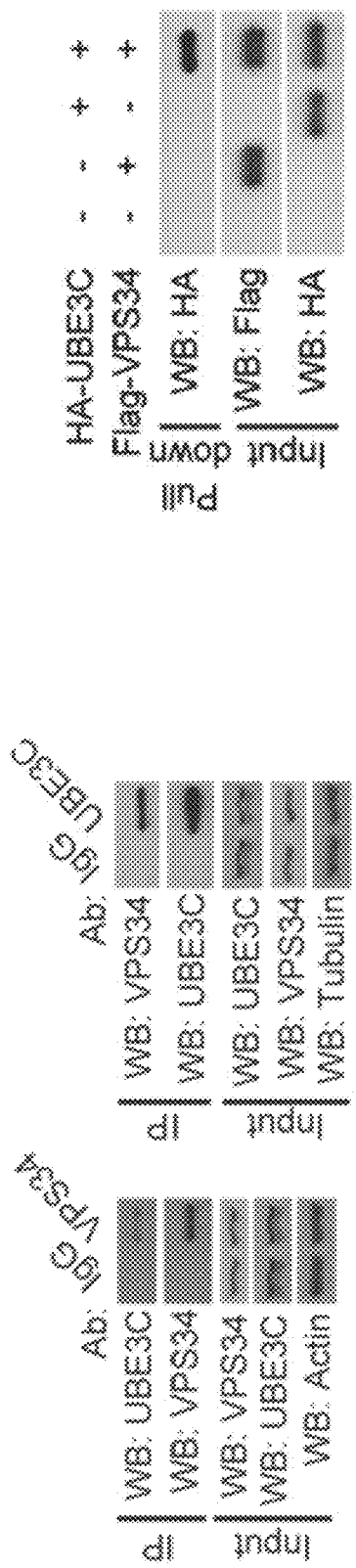
Figures 3C, 3D:
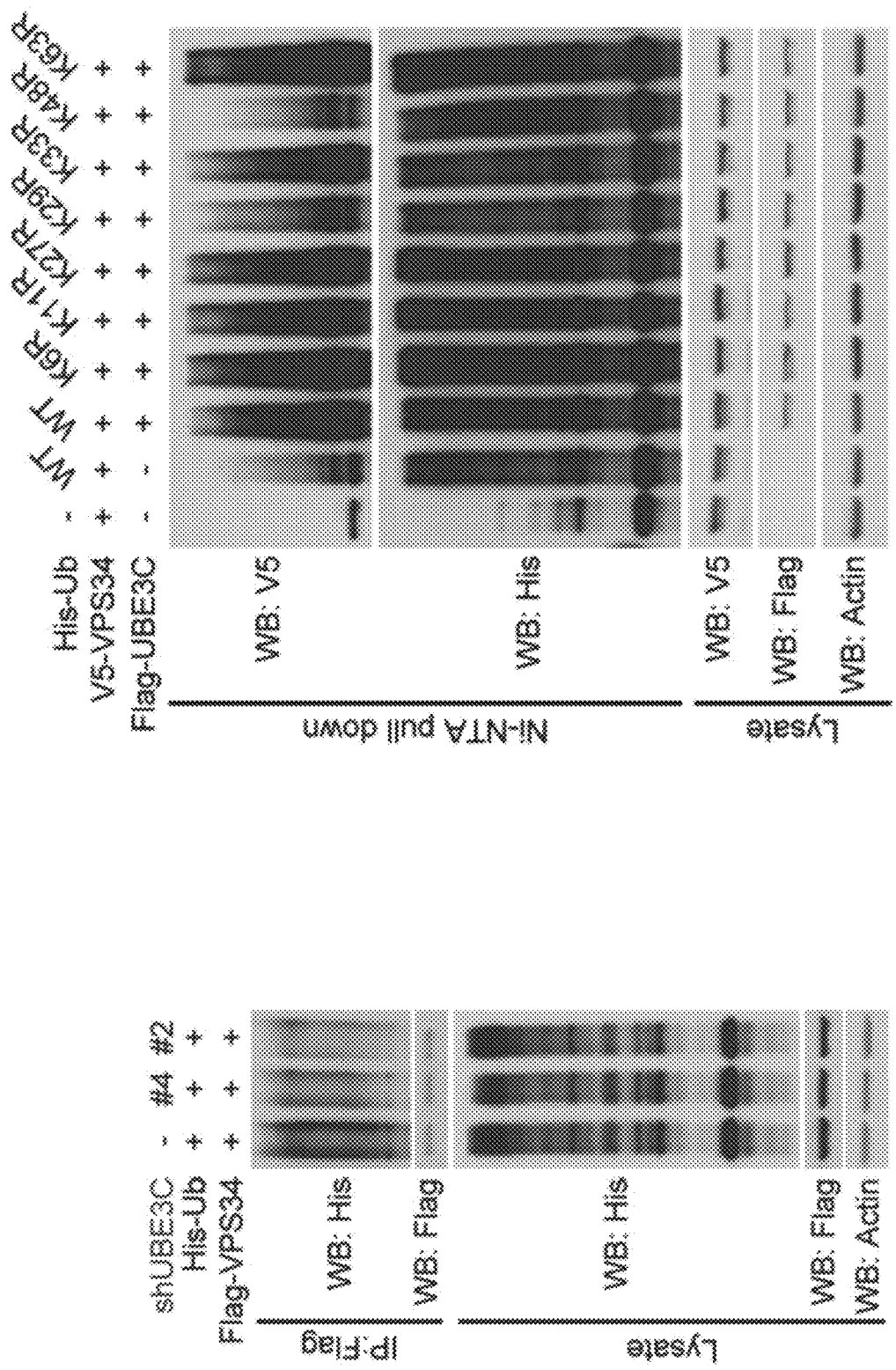
Figure 3F:
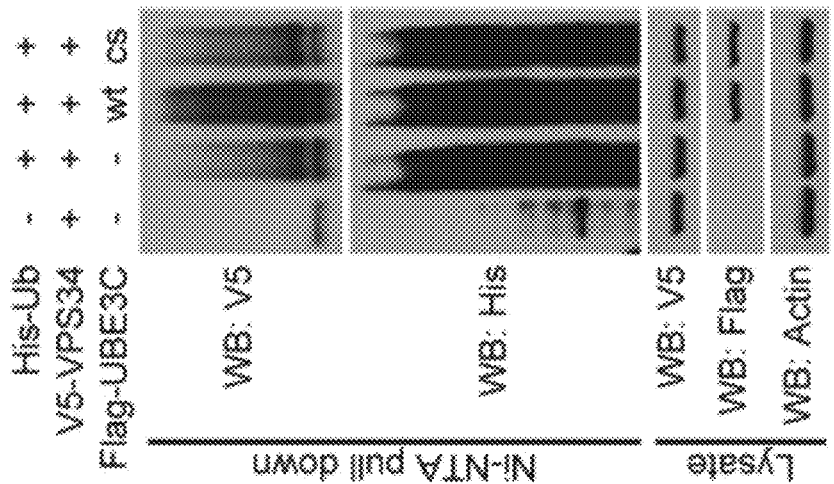
Figure 3E:
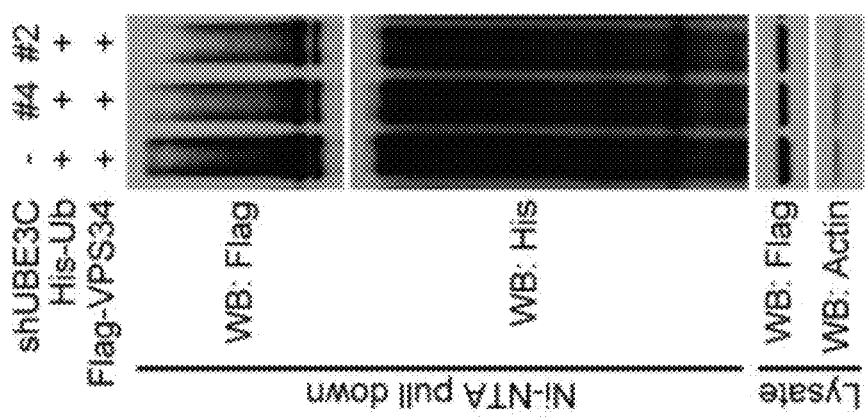
Figure 3G:
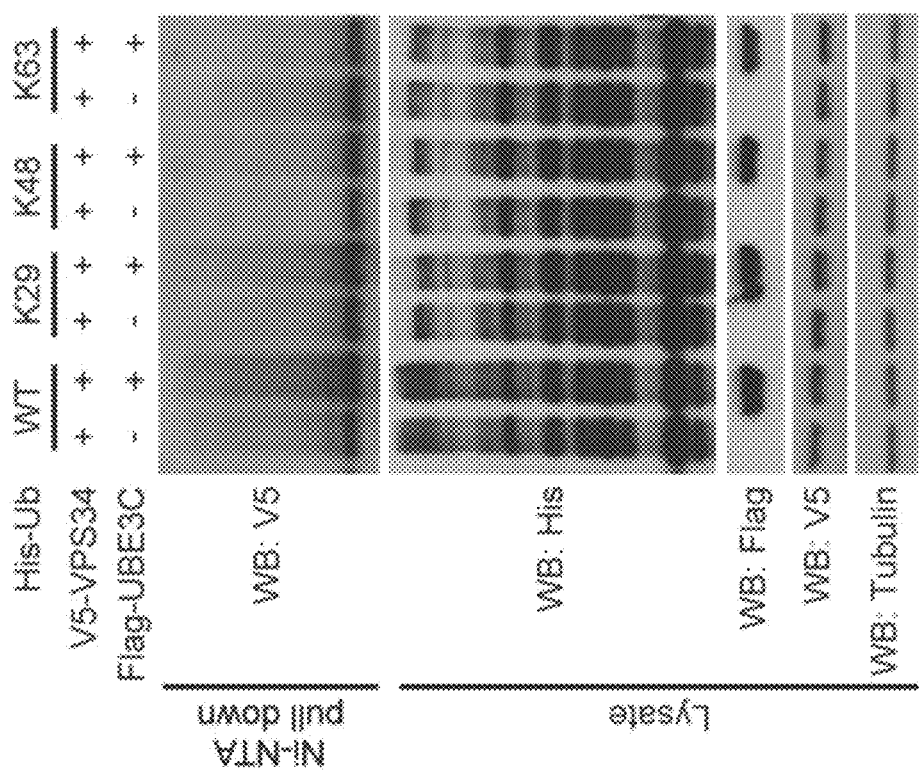

The ubiquitin ligase responsible for this ubiquitination event was further identified by UBE3C, which was reported to assemble a K29/K48 branched free ubiquitin chain in vitro[4]. As shown in FIGS. 3A and 3B, the endogenous interaction of UBE3C with VPS34 was demonstrated by reciprocal immunoprecipitation, and a direct interaction between UBE3C and VPS34 was detected by in vitro pull-down analysis. Furthermore, UBE3C depletion diminished VPS34 ubiquitination, whereas overexpression of UBE3C, but not its catalytically dead mutant, enhanced VPS34 ubiquitination (FIGS. 3C to 3F). The UBE3C-mediated VPS34 ubiquitination was partially inhibited by mutating the ubiquitin K29 or K48 residue (FIG. 3D). Furthermore, both K29-only and K48-only ubiquitin could partially support UBE3C-induced VPS34 ubiquitination, whereas K63-only ubiquitin could not (FIG. 3G).

These findings supported a role of UBE3C in mediating VPS34 K29/K48 heterotypic ubiquitination in vivo. To demonstrate that the heterotypic chain contains branched linkages, UBE3C-induced VPS34 ubiquitination level in cells expressing WT, K29/K48R (double mutant), or co-expressing K29R and K48R ubiquitin was evaluated. FIG. 3H showed that UBE3C-mediated VPS34 ubiquitination was greatly compromised by co-expressing K29R with K48R ubiquitin. Thus, these data supported a role of UBE3C in mediating VPS34 K29/K48 branched ubiquitination.

Next, FIG. 3I showed that by in vitro ubiquitination assay, baculovirally purified UBE3C could assemble polyubiquitin chain on VPS34 purified from 293T cells, supporting VPS34 as a direct substrate of UBE3C. To evaluate the formation of branched ubiquitin chain on UBE3C-catalyzed VPS34 and its abundance, the recently established Ub-clipping method was utilized[3]. This method disassembles polyubiquitin chain into GG-modified monoubiquitin by an engineered Lb$^{pro}$* protease, which cleaves ubiquitin after the Arg74 residue. Thus, the ubiquitin moiety in the linear or branched point generates one or two (or multiple) GG-modified ubiquitin species, respectively, which can be detected by intact mass spectrometry (MS).

Figure 3J:
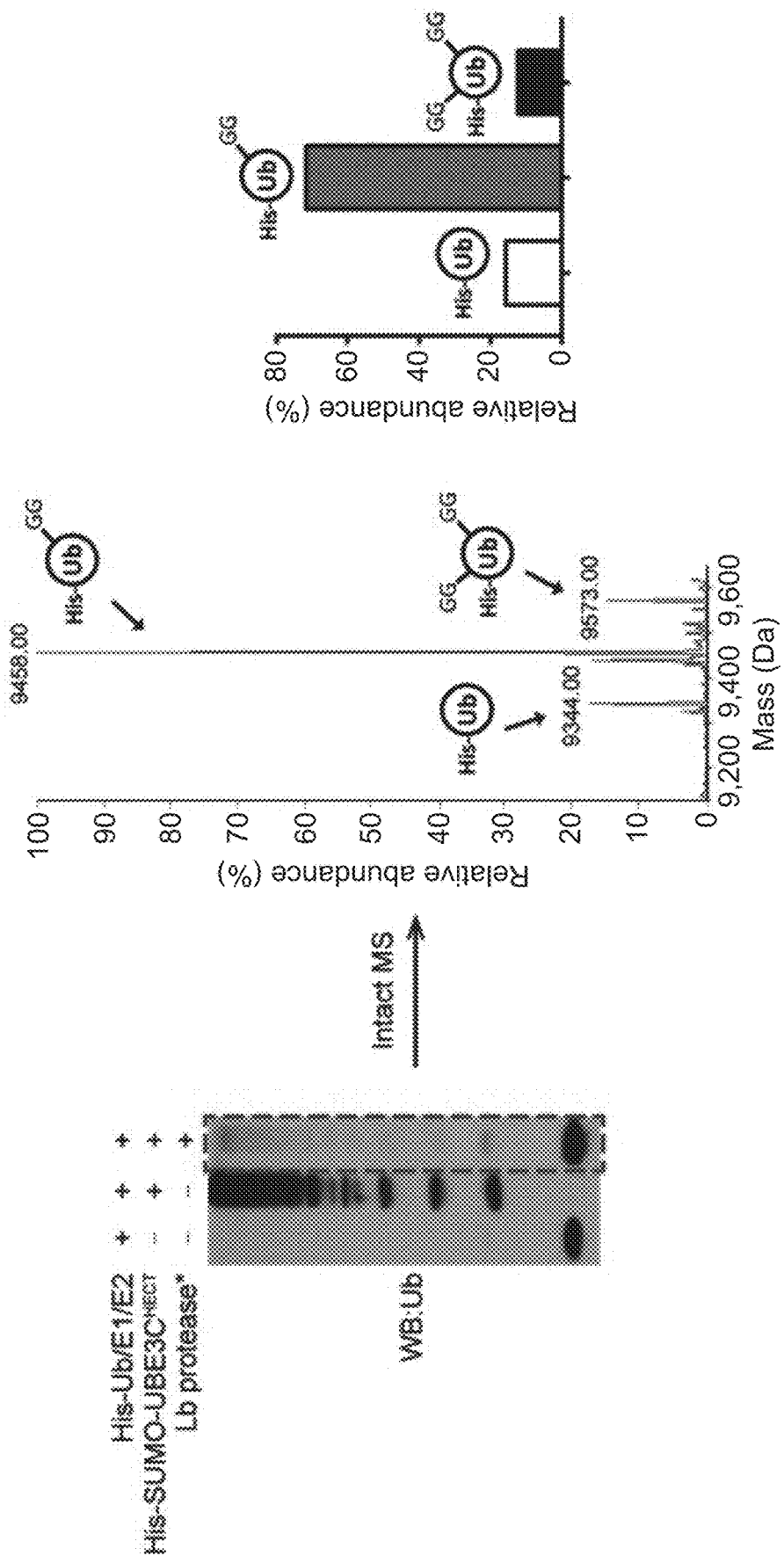
FIG. 3J shows that the UBE3C assembles branched free ubiquitin chains in vitro, wherein left panel shows Ub-clipping assay of the free ubiquitin chain assembled in vitro by UBE3C$^{HECT}$ (the catalytic domain of UBE3C); middle panel shows intact MS analysis of reaction product as shown in lane 3 of left panel, in which spectrum is deconvoluted and peaks corresponding to unmodified, single- and double-GG modified ubiquitin are indicated; and right panel shows quantification of the relative abundance of each ubiquitin species.
Figure 3L:
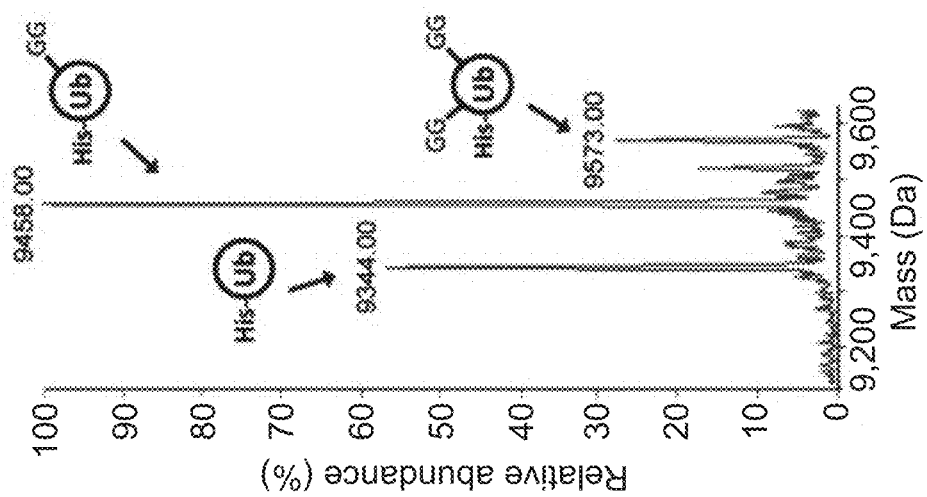
FIG. 3L shows assembly of branched ubiquitin chain on VPS34 by UBE3C, wherein left panel shows Ub-clipping assay of the ubiquitin chain assembled on VPS34, in which VPS34 bound on beads is ubiquitinated in vitro in the presence or absence of UBE3C, and the beads are then washed, treated with or without Lb$^{pro}$* and analyzed by Western blot, with asterisks denoting the immunoglobulin heavy and light chains; and right panel shows intact MS analysis of reaction product as shown in lane 4 of left panel, in which spectrum is deconvoluted and peaks corresponding to unmodified, single- and double-GG modified ubiquitin are indicated.
Figure 3L:
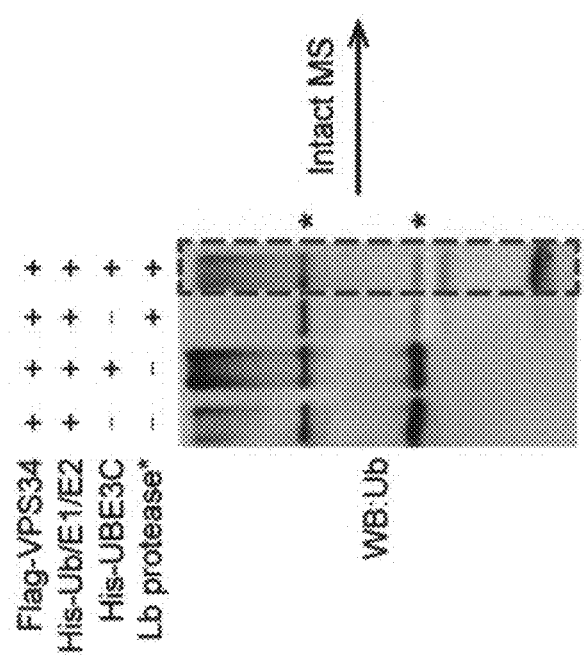
Figure 3K:
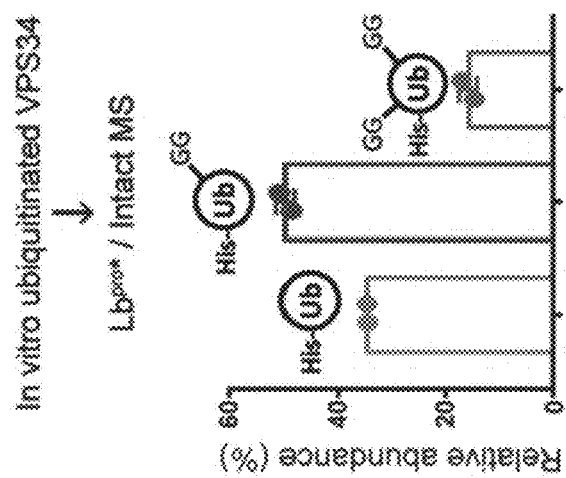
FIG. 3K shows quantification of indicated ubiquitin species identified by intact MS analysis on in vitro ubiquitinated and Lb$^{pro}$*-treated VPS34. Data are means from two independent experiments.
Figure 3M:
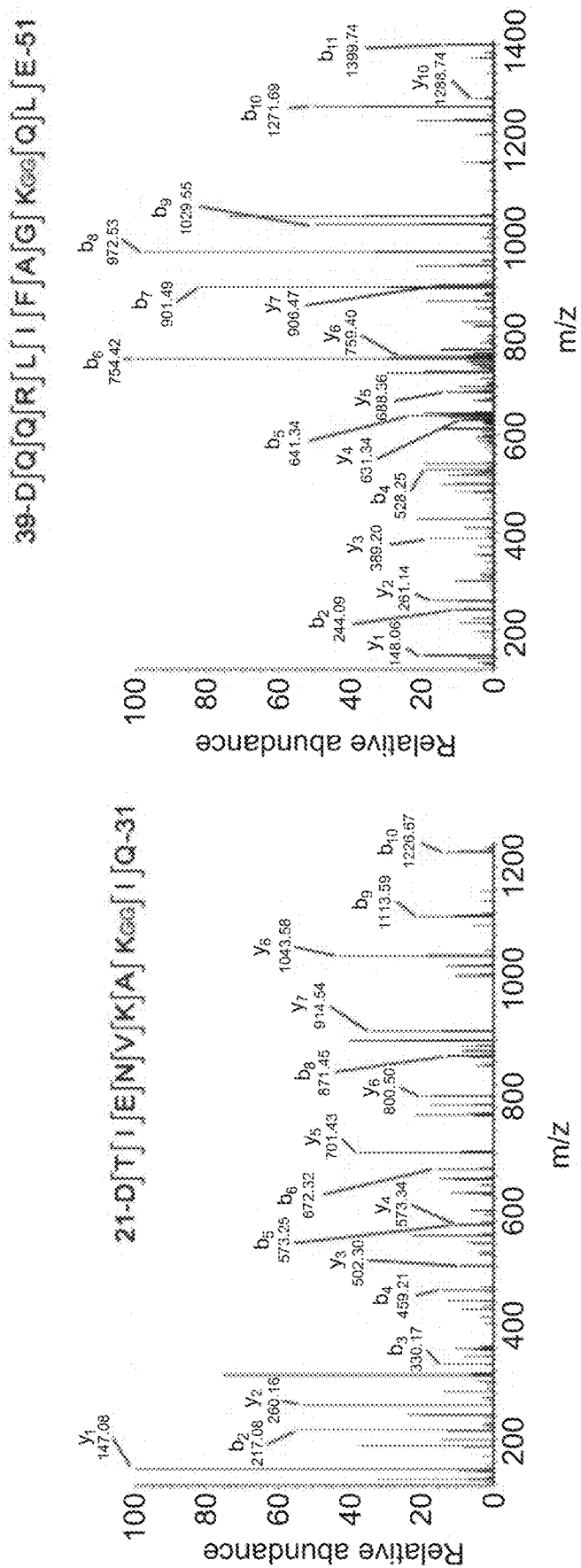
FIG. 3M shows representative tandem mass spectra showing the presence of GG-modification in the K29 (left) and K48 (right) residues of ubiquitin, wherein the clipped ubiquitin monomer derived from an experiment as shown in lane 3 and lane 4 of FIG. 3L are analyzed by LC-MS/MS.

To validate the methodology, the free polyubiquitin chain assembled by UBE3C in vitro was analyzed. After Lb$^{pro}$* treatment, intact MS identified the existence of double GG-modified ubiquitin species, and quantification by peak integration indicated that it represents 12.5% of total ubiquitin (FIG. 3J). Further, the ubiquitin chain on VPS34 that was assembled by UBE3C in vitro was analyzed. To this end, VPS34 bound on beads was in vitro ubiquitinated, washed, and cleaved by Lb$^{pro}$*. The cleavage product was analyzed by intact MS and LC-MS/MS for detecting branched ubiquitin chain and ubiquitin linkage types, respectively. FIGS. 3K and 3L demonstrate 15.7% of branched ubiquitin chain on UBE3C-modified VPS34. In addition, K29-GG and K48-GG were the only two types of GG-modified ubiquitin peptides detected from in vitro ubiquitinated VPS34, and their abundance was greatly enhanced by the presence of UBE3C in the ubiquitination reaction (Table 3 below and FIG. 3M). Together, these in vitro and in vivo studies provided evidence for the ability of UBE3C to assemble an K29/K48 branched ubiquitin chain on VPS34.

TABLE 3

| | Ubiquitination-Lb$^{pro}$*-LC/MS/MS: peak intensity | | | |
|---|---|---|---|---|
| | K29-GG | | K48-GG | |
| | UBE3C− | UBE3C+ | UBE3C− | UBE3C+ |
| Exp I | ND* | 1.26 ×10$^5$ | 1.86 ×10$^4$ | 6.59 ×10$^6$ |
| Exp II | ND* | 3.64 ×10$^5$ | 4.70 ×10$^4$ | 1.02 ×10$^7$ |

*Not detected

Figure 3N:
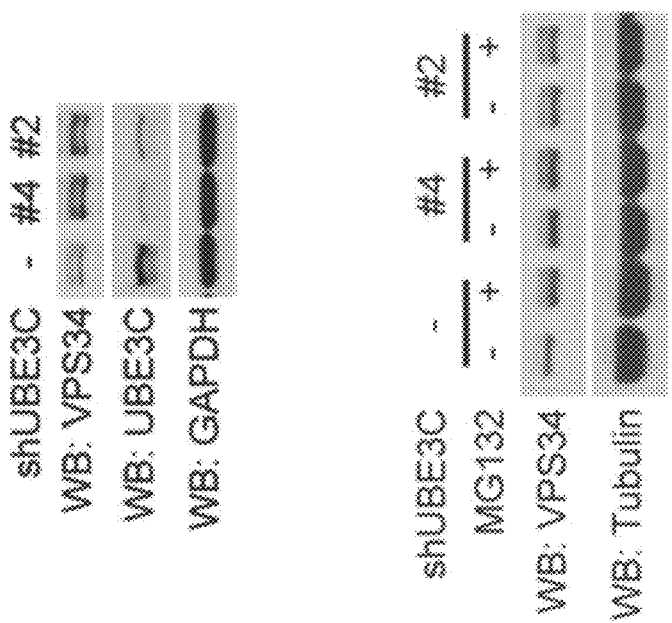
FIG. 3N shows the results of Western blot analysis of VPS34 levels in 293T cells stably expressing UBE3C shRNAs (upper panel) and treated with MG132 (lower panel).

Example 5: VPS34 K29/K48 Branched Ubiquitination Enhances its Proteasome Binding and Degradation The consequence of VPS34 branched ubiquitination by UBE3C was determined. As shown in FIGS. 3N and 3O, UBE3C knockdown in 293T cells and HeLa cells increased VPS34 protein abundance and inhibited its proteasomal degradation. UBE3C knockout by the CRISPR-Cas9 strategy also elevated VPS34 expression, implying that UBE3C promotes VPS34 degradation (FIG. 3P).

Studies with the K11/K48 branched ubiquitination indicated that such branched chain offers a stronger proteolytic signal than the K48 linear chain, which is resulted from an enhanced binding of branched ubiquitin chain to the proteasome[5,6]. To determine whether this is the case for K29/K48 branched ubiquitin chain, the ubiquitin replacement system was used.

Figures 3Q, 3R:
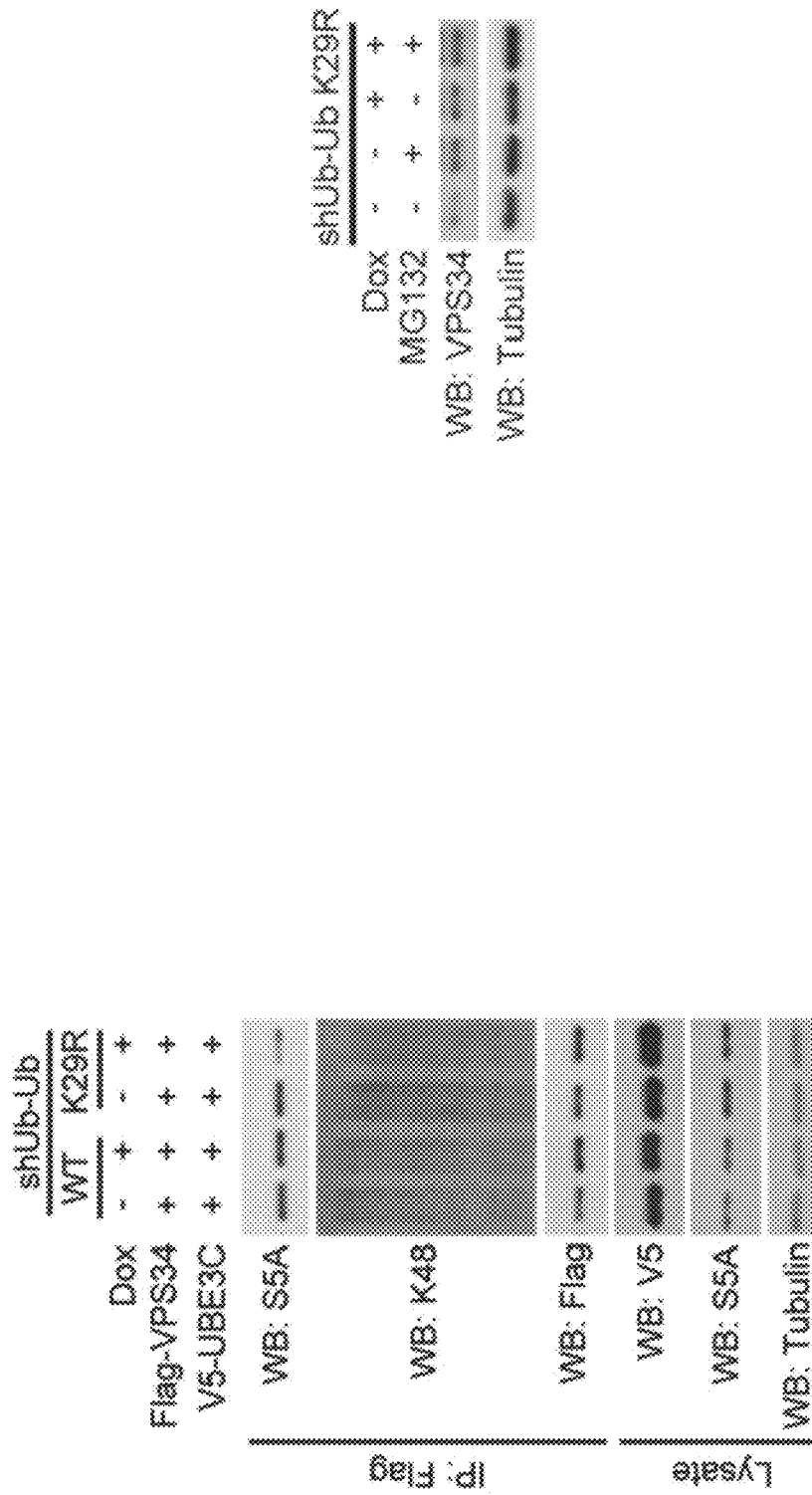
Figure 3S:
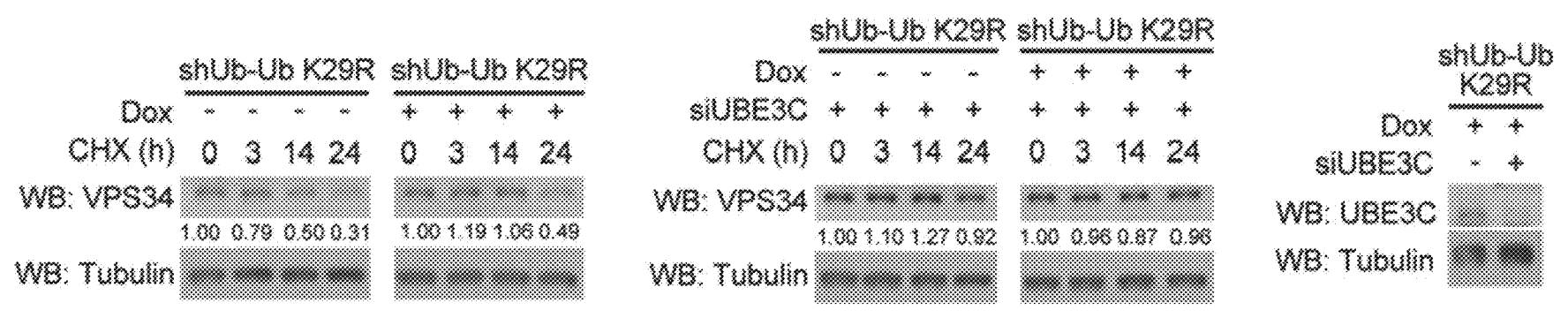

It is noted that doxycycline treatment of K29R cells results in the replacement of endogenous ubiquitin with K29R ubiquitin, thereby facilitating a switch of K29/K48 branched ubiquitination to K48 ubiquitination. It was also found that doxycycline treatment of K29R cells, but not wild type cells, led to a decreased binding of ubiquitinated VPS34 to the proteasome ubiquitin receptor SSA, also known as RPN10 (FIG. 3Q). Accordingly, doxycycline treatment of K29R cells increased VPS34 stability through a UBE3C-dependent manner and attenuated VPS34 proteasomal degradation (FIGS. 3R and 3S). Thus, formation of K29/K48 branched ubiquitin chain enhanced VPS34 proteasomal binding and proteasomal degradation.

Example 6: UBE3C and TRABID Coordinately Govern a Balanced Autophagy Activity

Figure 4A:
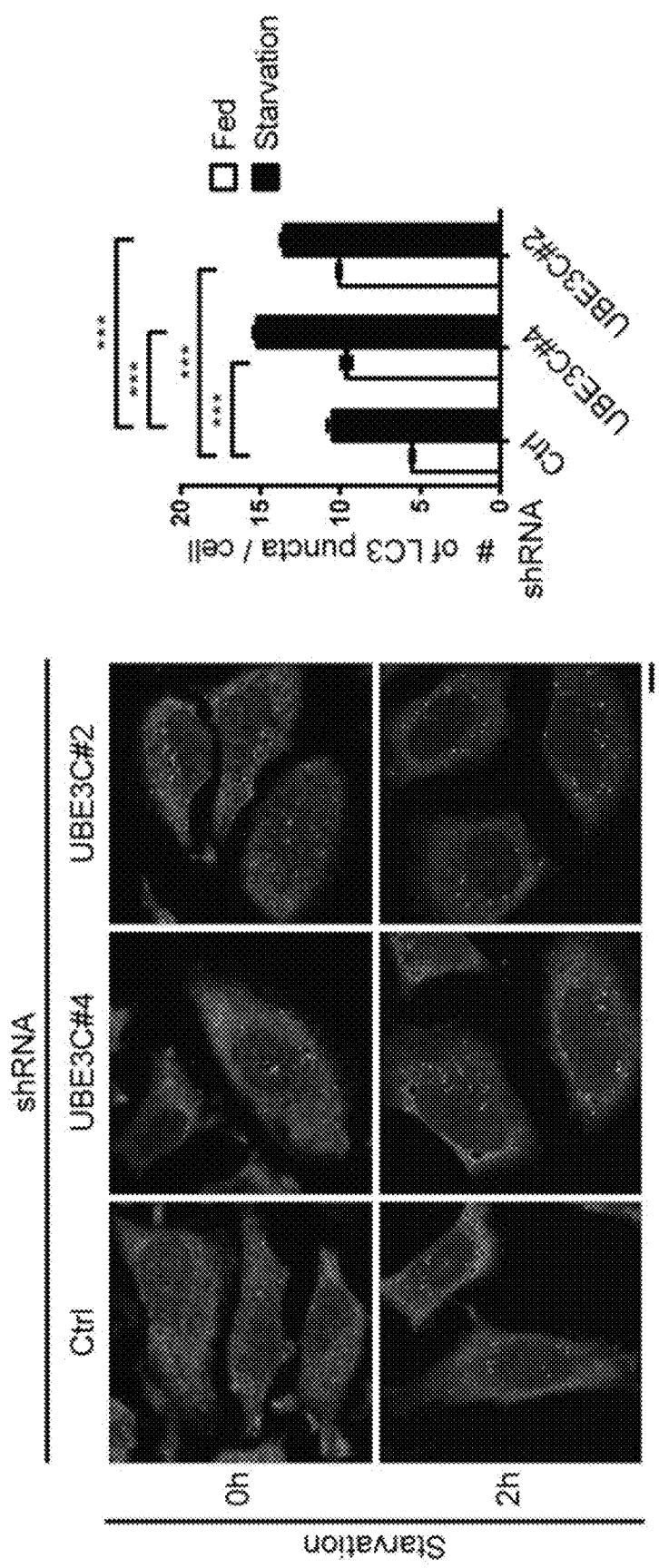
Figure 4B:
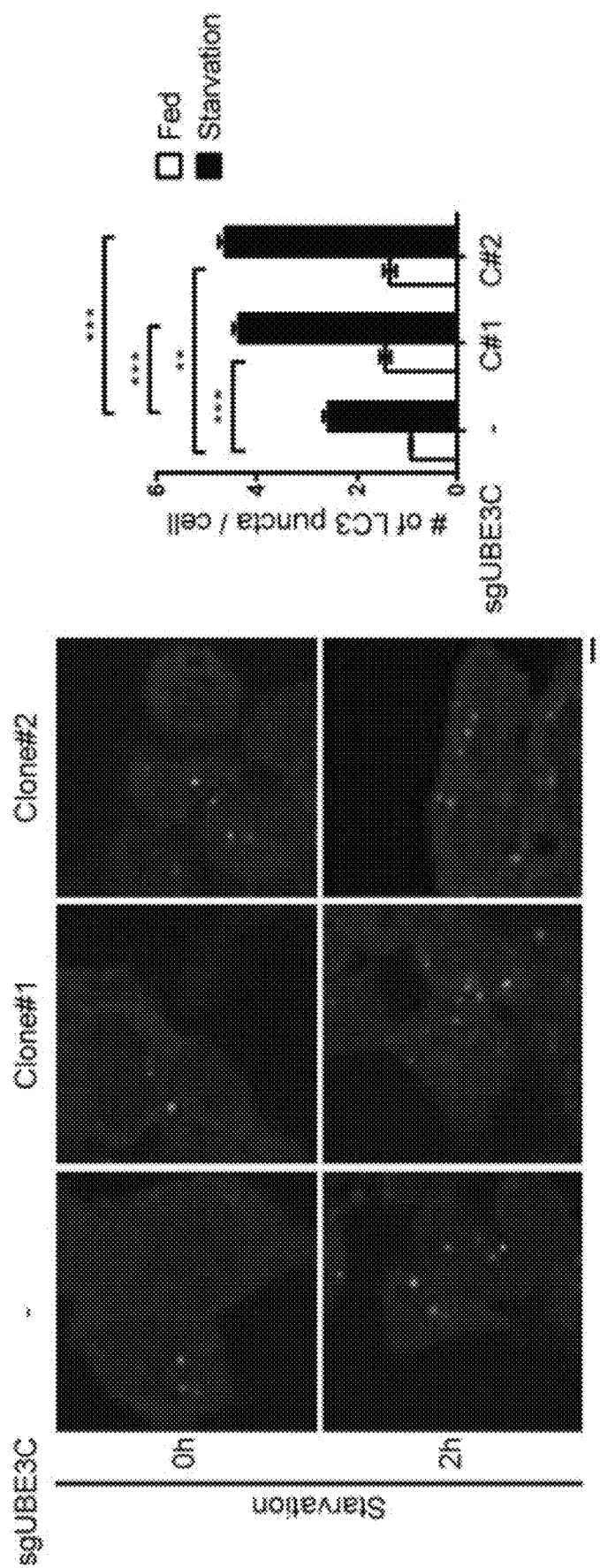
Figure 4C:
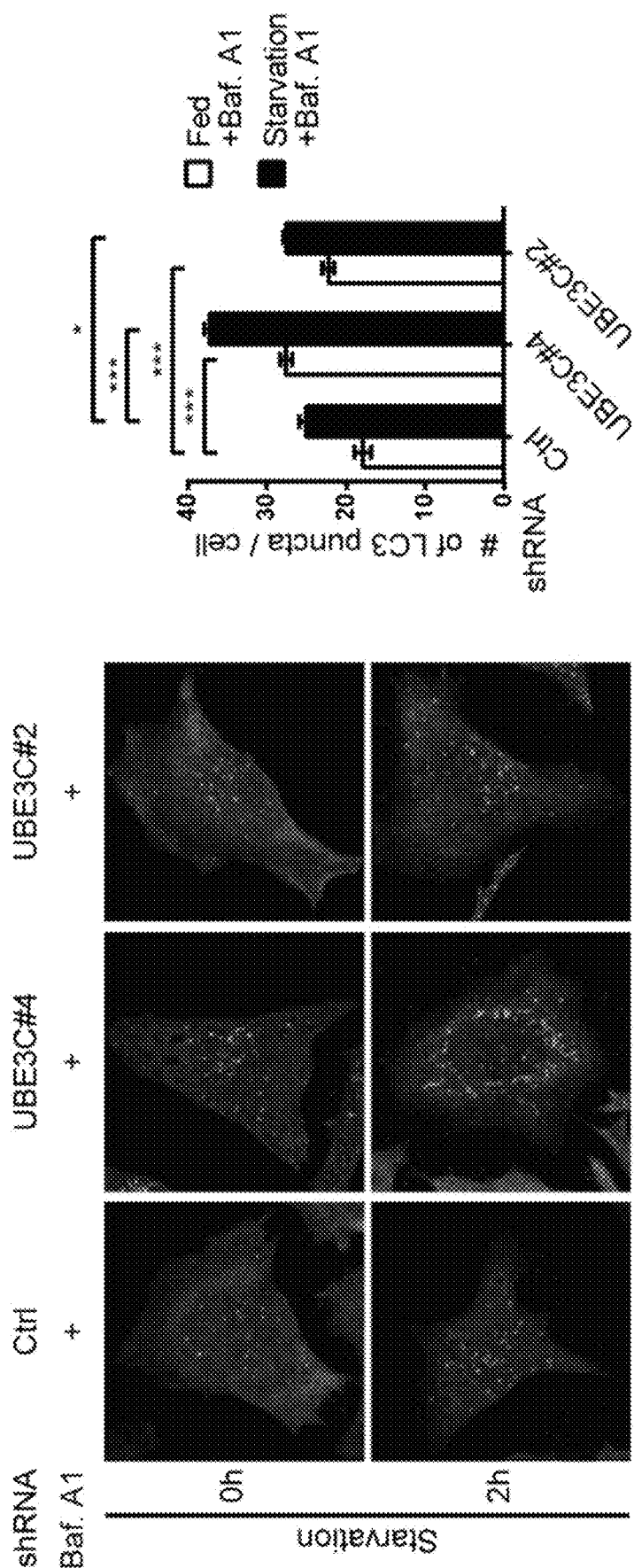
Figure 4D:
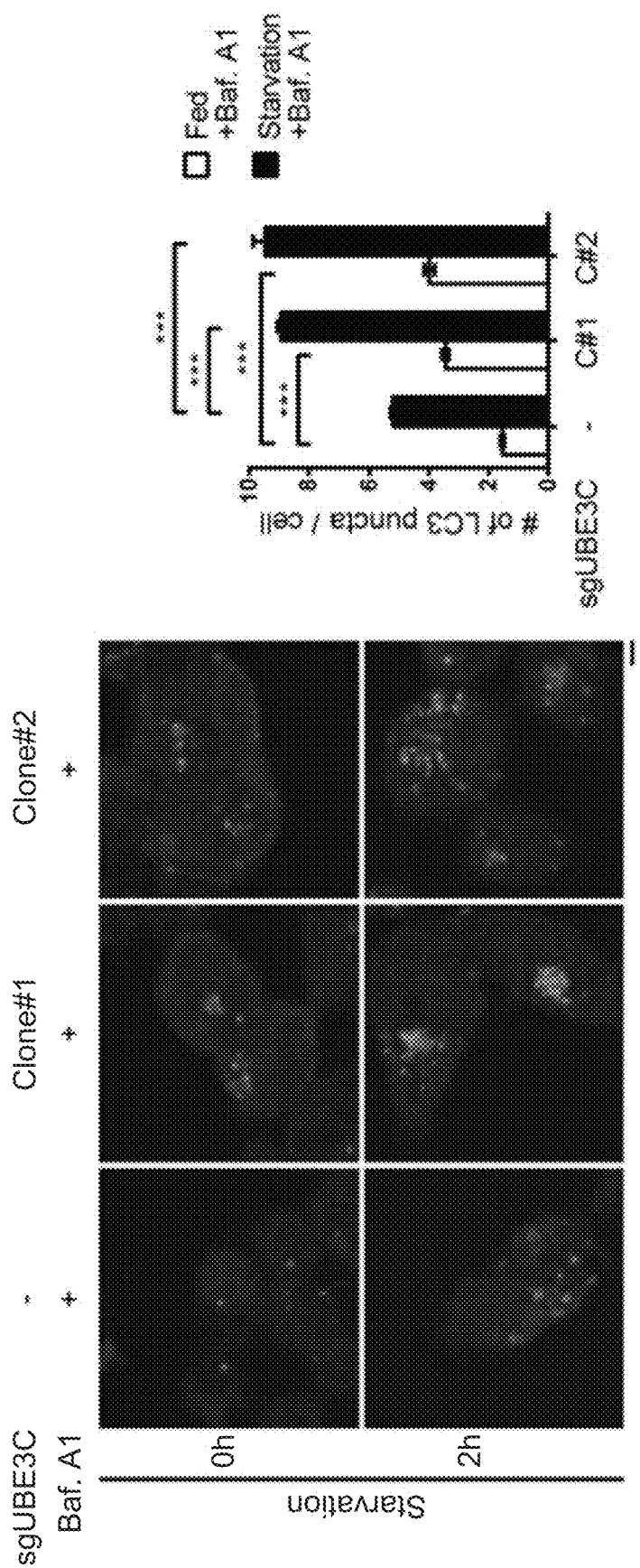
Figure 4E:
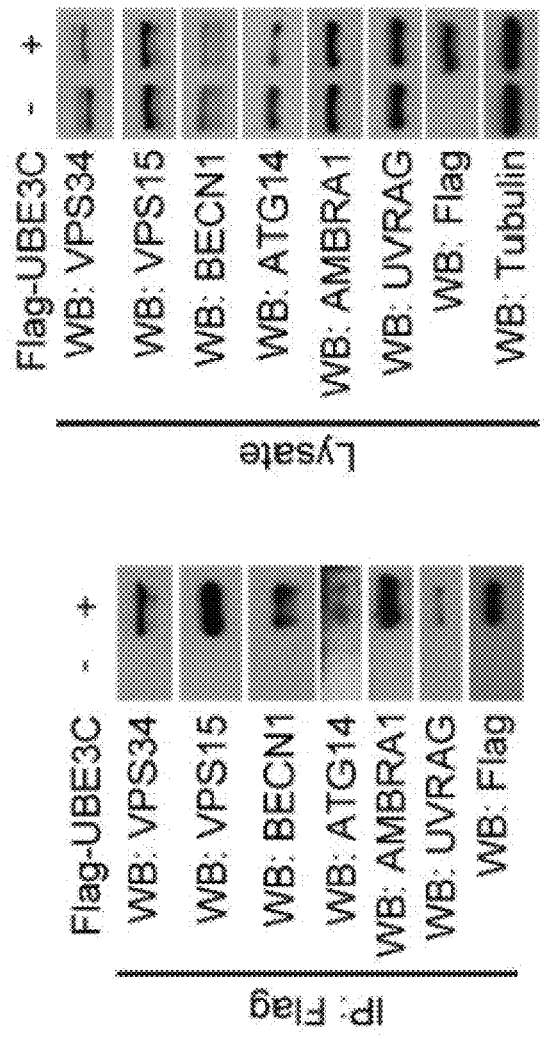
Figure 4F:
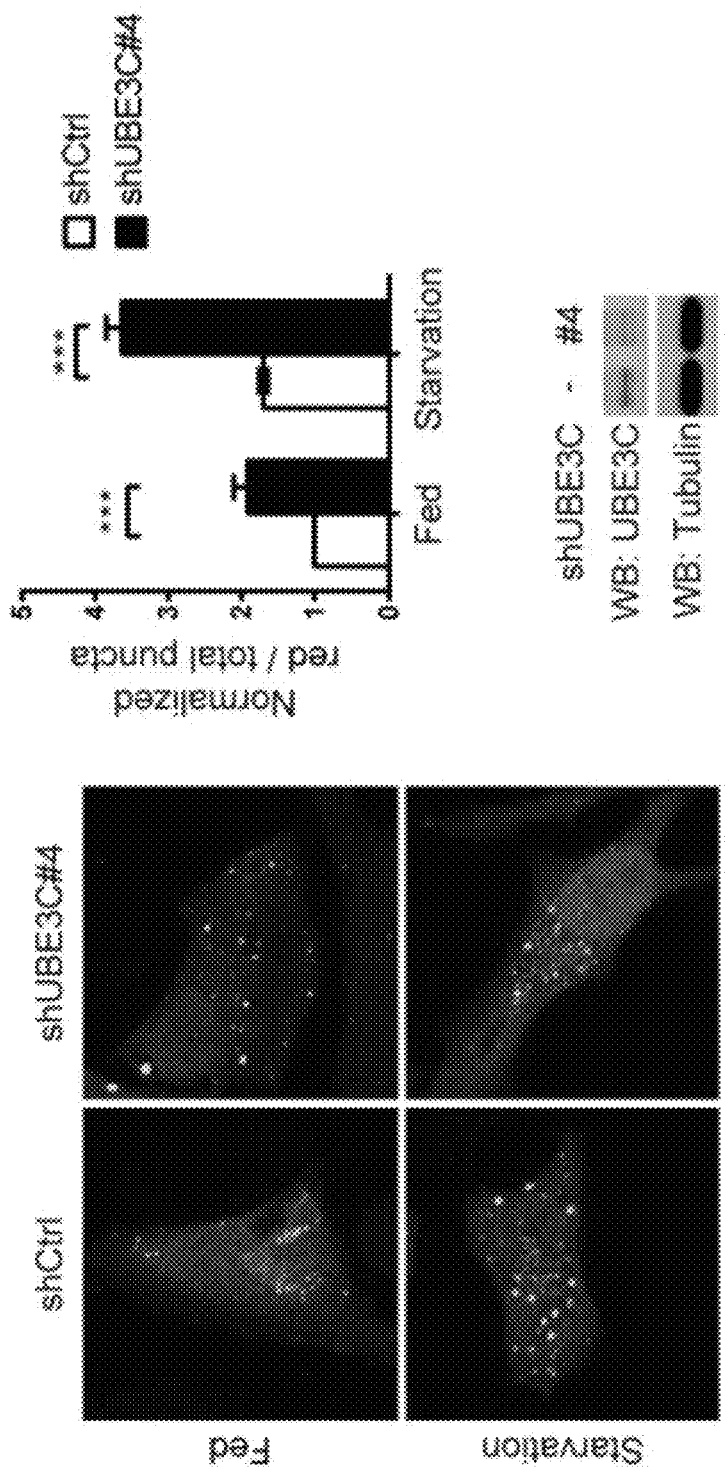

The ability of UBE3C to induce VPS34 branched ubiquitination and degradation suggests its autophagy inhibitory effect. It was observed that UBE3C knockdown or knockout (KO) increased LC3 puncta and LC3 lipidation in fed and starved cells (FIGS. 4A and 4B), and these effects were preserved in bafilomycin A1-treated conditions (FIGS. 4C and 4D). Similar to TRABID, UBE3C was able to associate with VPS34 complex I and complex II (FIG. 4E). Furthermore, UBE3C depletion enhanced autophagosome maturation in fed and starved conditions (FIG. 4F). Thus, UBE3C elicited inhibitory roles in autophagosome formation and maturation.

Figure 4G:
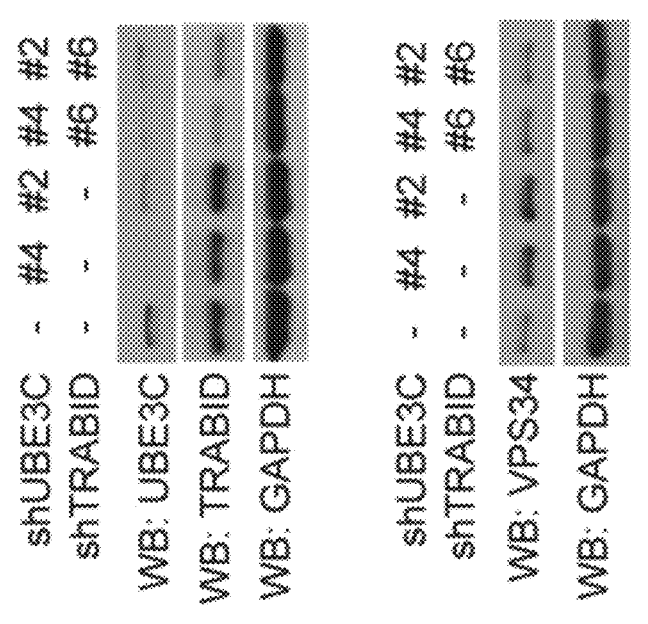
Figure 4H:
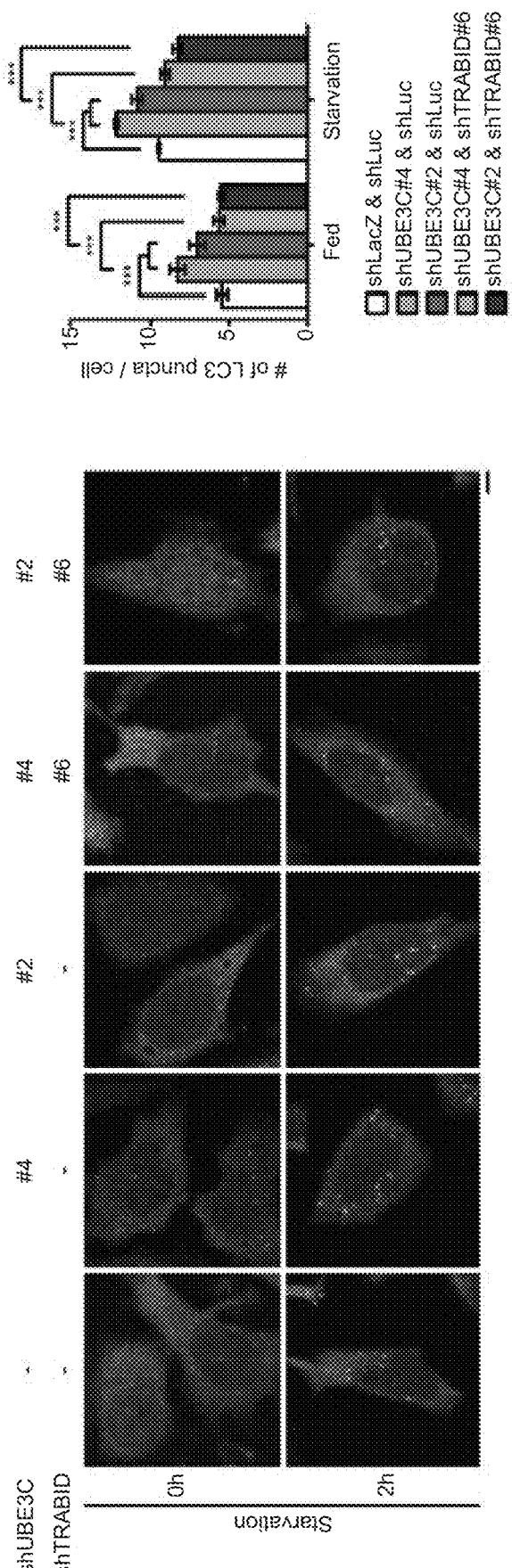

To demonstrate an antagonizing role of UBE3C and TRABID in VPS34 and autophagy regulation, UBE3C and TRABID double knockdown cells were established. FIGS. 4G and 4H demonstrated that UBE3C depletion-induced upregulation of VPS34 expression, LC3 puncta and LC3 lipidation in fed and starved cells were all reversed by TRABID knockdown, indicating that UBE3C and TRABID coordinately regulate VPS34 stability in basal and starvation conditions, which involves in maintaining a balanced autophagy activity.

Figure 5A:
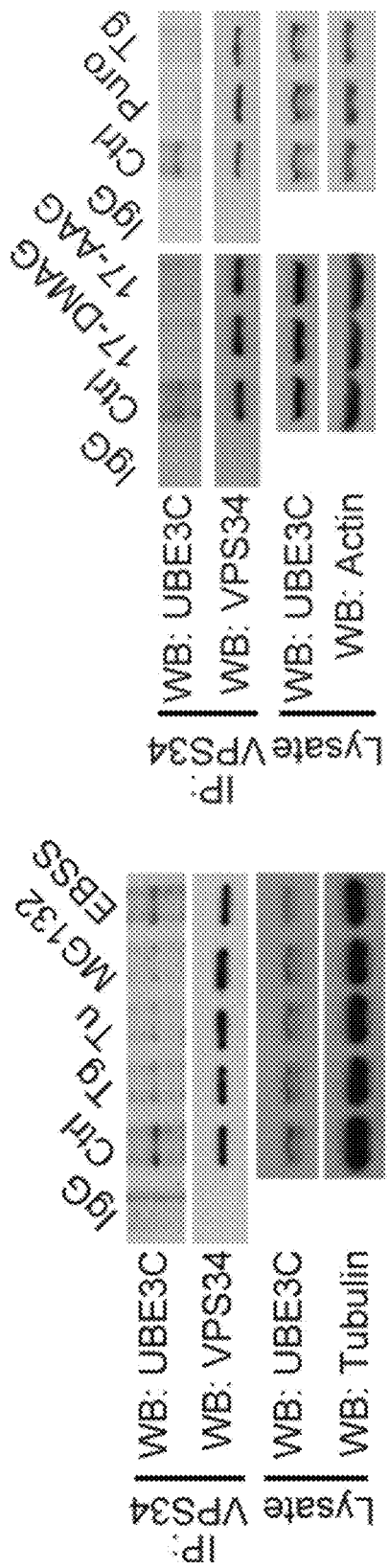
FIGS. 5A to 5N are graphs illustrating that endoplasmic reticulum (ER) and proteotoxic stresses attenuate the actions of UBE3C on VPS34 by altering UBE3C partners.
Figure 5B:
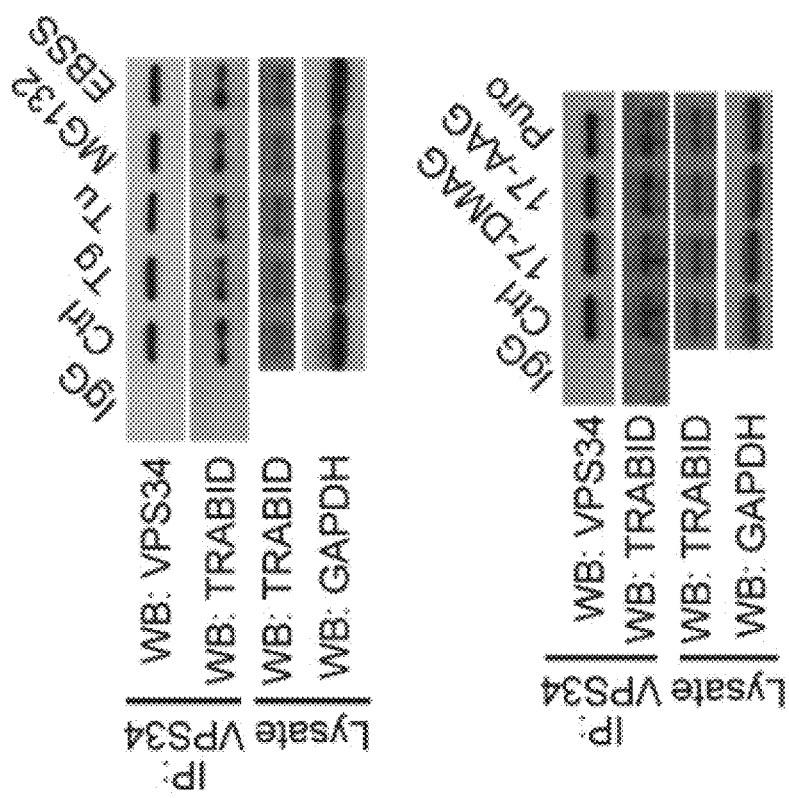
FIG. 5B shows the results of immunoprecipitation analysis of the interaction between endogenous TRABID and VPS34 in 293T cells treated with indicated agents for 1 h.
Figure 5D:
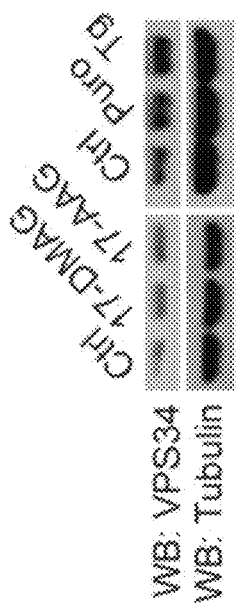
FIG. 5D shows the results of Western blot analysis of VPS34 levels in 293T cells treated with indicated agents for 1 h.
Figure 5C:
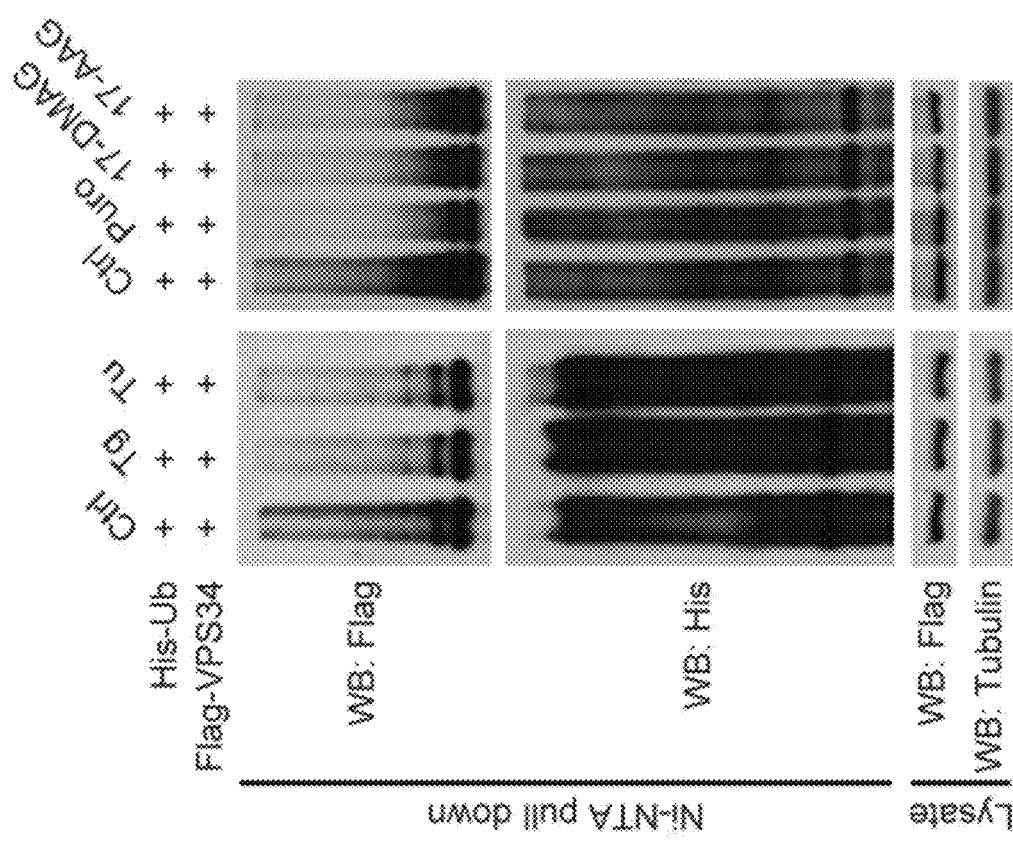
FIG. 5C shows the analysis results of VPS34 ubiquitination in 293T cells transfected with indicated constructs and treated with indicated agents for 1 h.
Figures 5E, 5F:
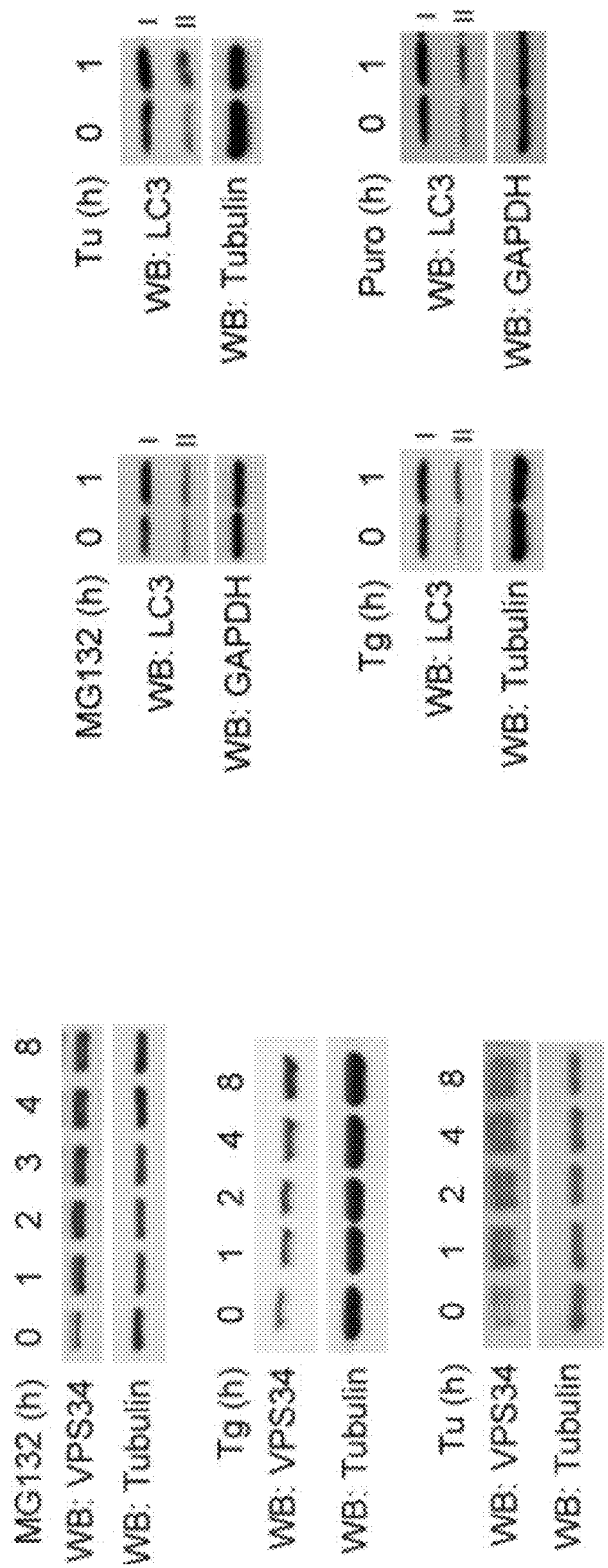
FIG. 5E shows the results of Western blot analysis of VPS34 levels in 293T cells treated with indicated agents for indicated time points.
FIG. 5F shows the results of Western blot analysis of LC3 in 293T cells treated with indicated agents for 1 h.

Example 7: Endoplasmic Reticulum (ER) and Proteotoxic Stresses Attenuate UBE3C's Action on VPS34 and Enhances its Proteasome Association As shown in FIG. 5A, as compared with basal and starved conditions, the interaction of VPS34 with UBE3C was diminished in response to various ER stressors or proteotoxic stressors, such as tunicamycin, thapsigargin, puromycin, MG132, 17-AAG or 17-DMAG, the latter two being the HSP90 inhibitors. The interaction of TRABID with VPS34 was not altered under these conditions (FIG. 5B). These ER and proteotoxic stressors also decreased VPS34 ubiquitination and increased VPS34 protein abundance (FIGS. 5C to 5E). Of note, these ER and proteotoxic stressors were capable of inducing autophagy, as evident by increased LC3 lipidation (FIG. 5F). These findings suggested that the balance between UBE3C and TRABID on VPS34 regulation was disturbed by various ER/proteotoxic stressors to favor TRABID-mediated VPS34 stabilization, thereby facilitating autophagy induction.

Figure 5G:
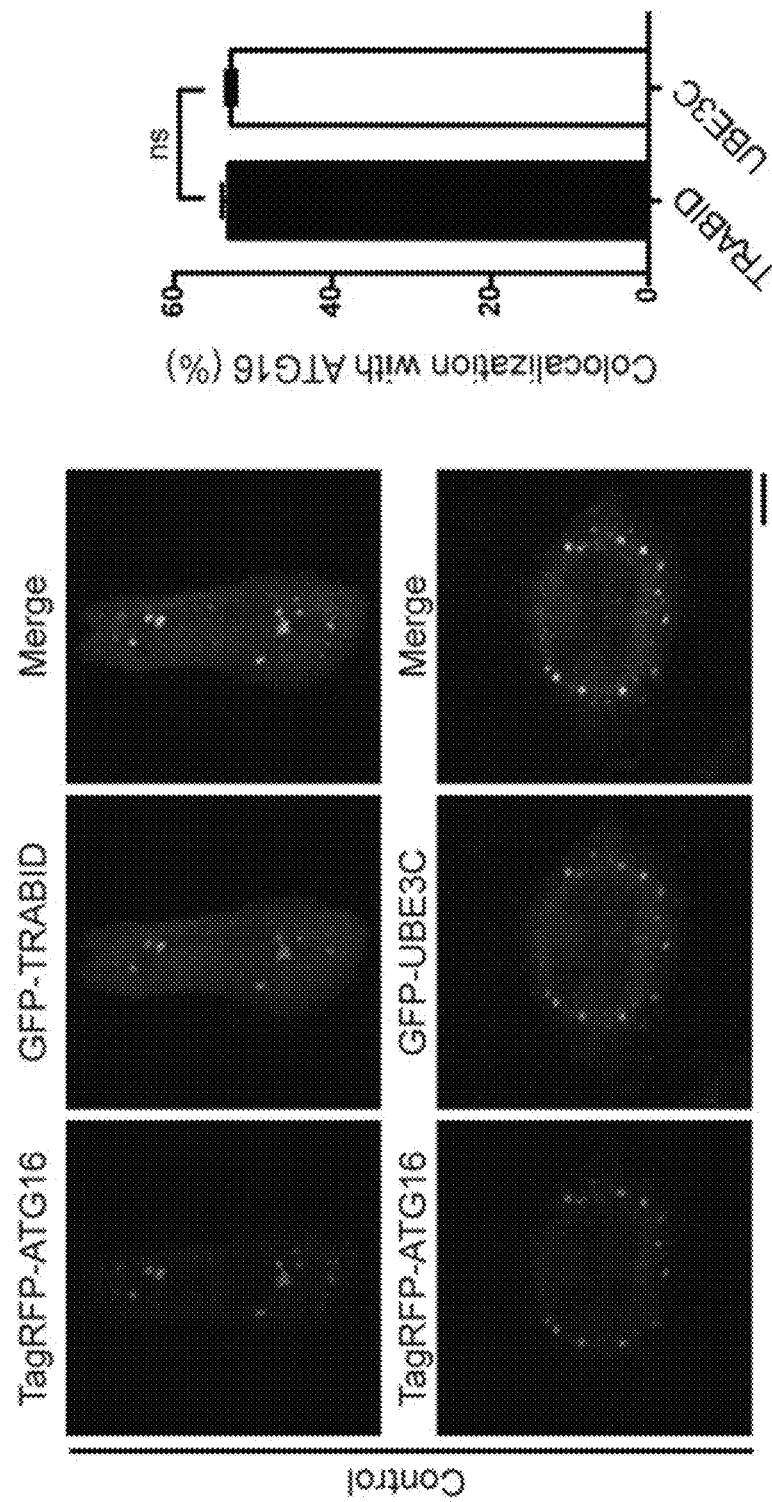
FIGS. 5G to 5J show the results of confocal analysis of the colocalization of TagRFP-ATG16 with GFP-TRABID, GFP-UBE3C and/or BFP-UBE3C in transfected HeLa cells cultured in starvation or in fed conditions or treated with tunicamycin or puromycin for 1 h. Bar: 10 μm. The percentage of GFP-TRABID or GFP-UBE3C puncta colocalizing with TagRFP-ATG16 puncta is analyzed and plotted.
Figure 5H:
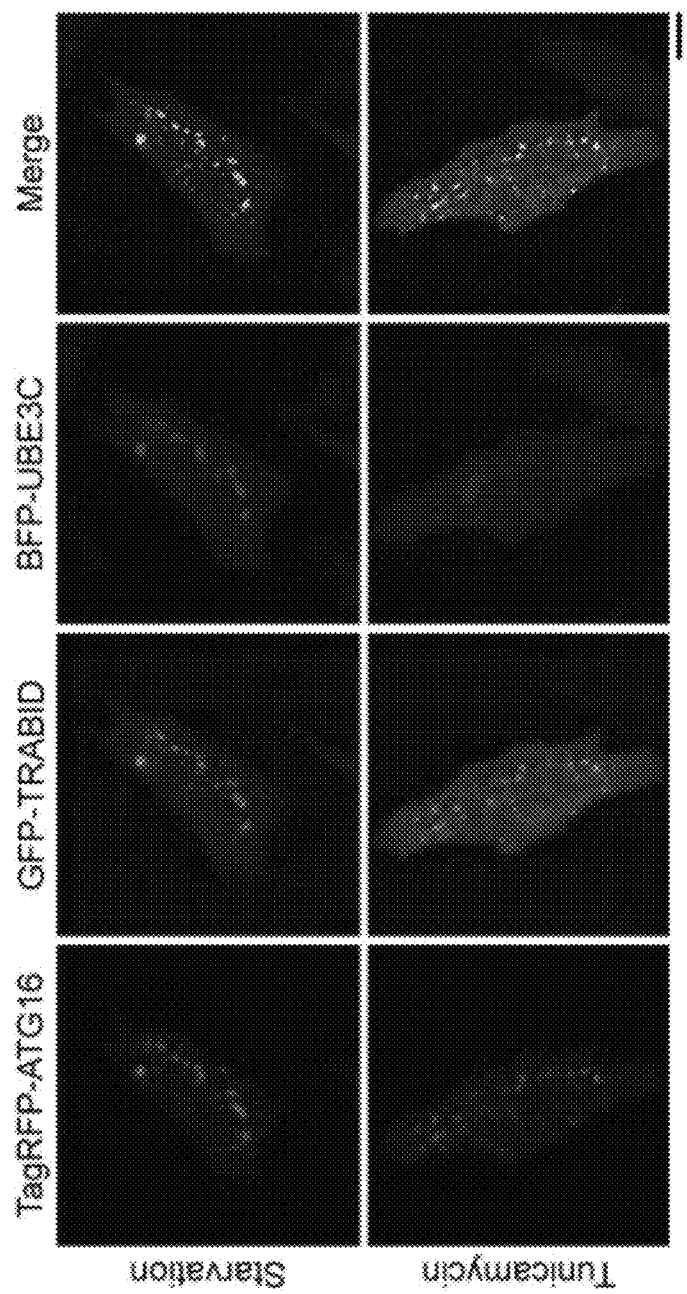
Figure 5I:
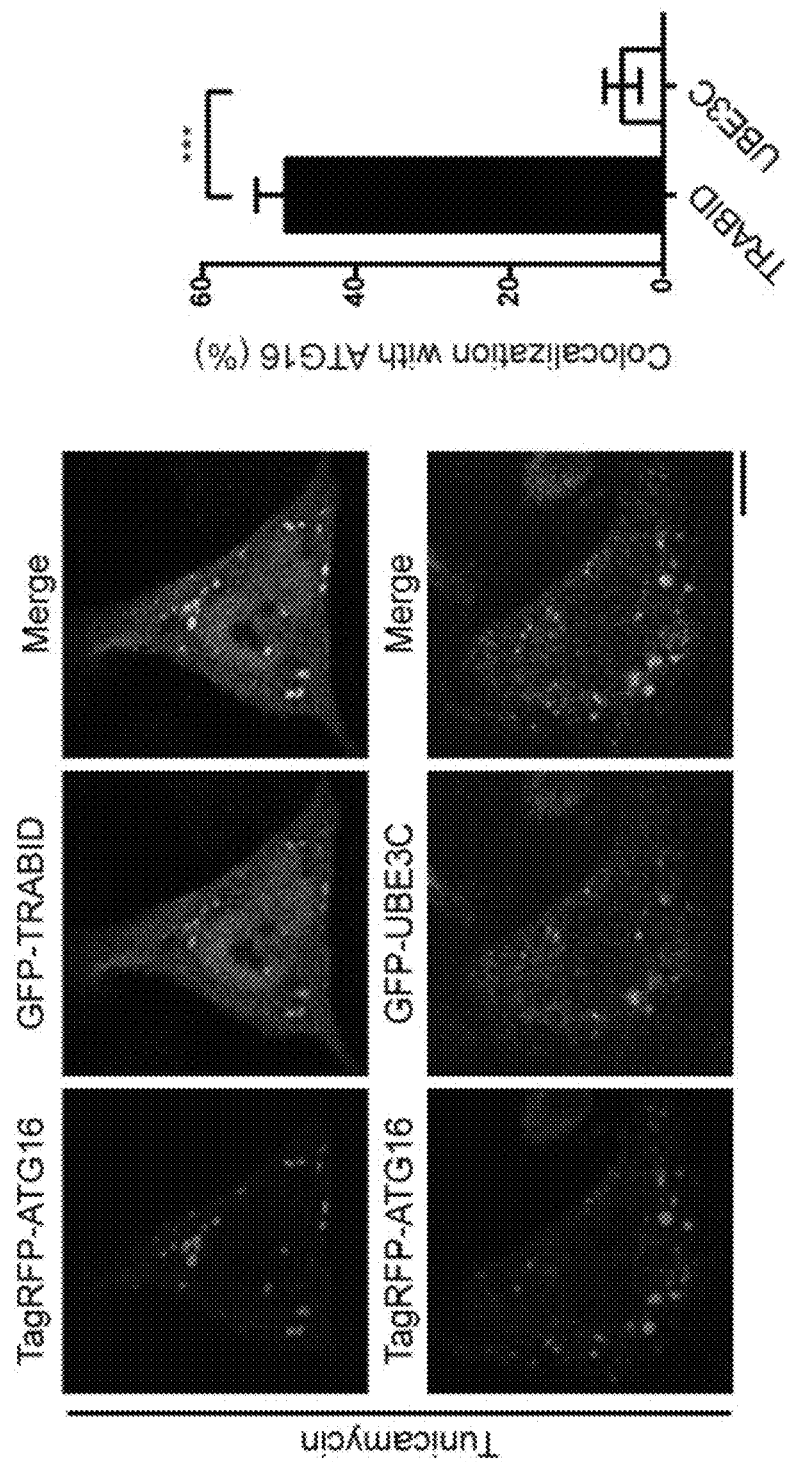
Figure 5J:
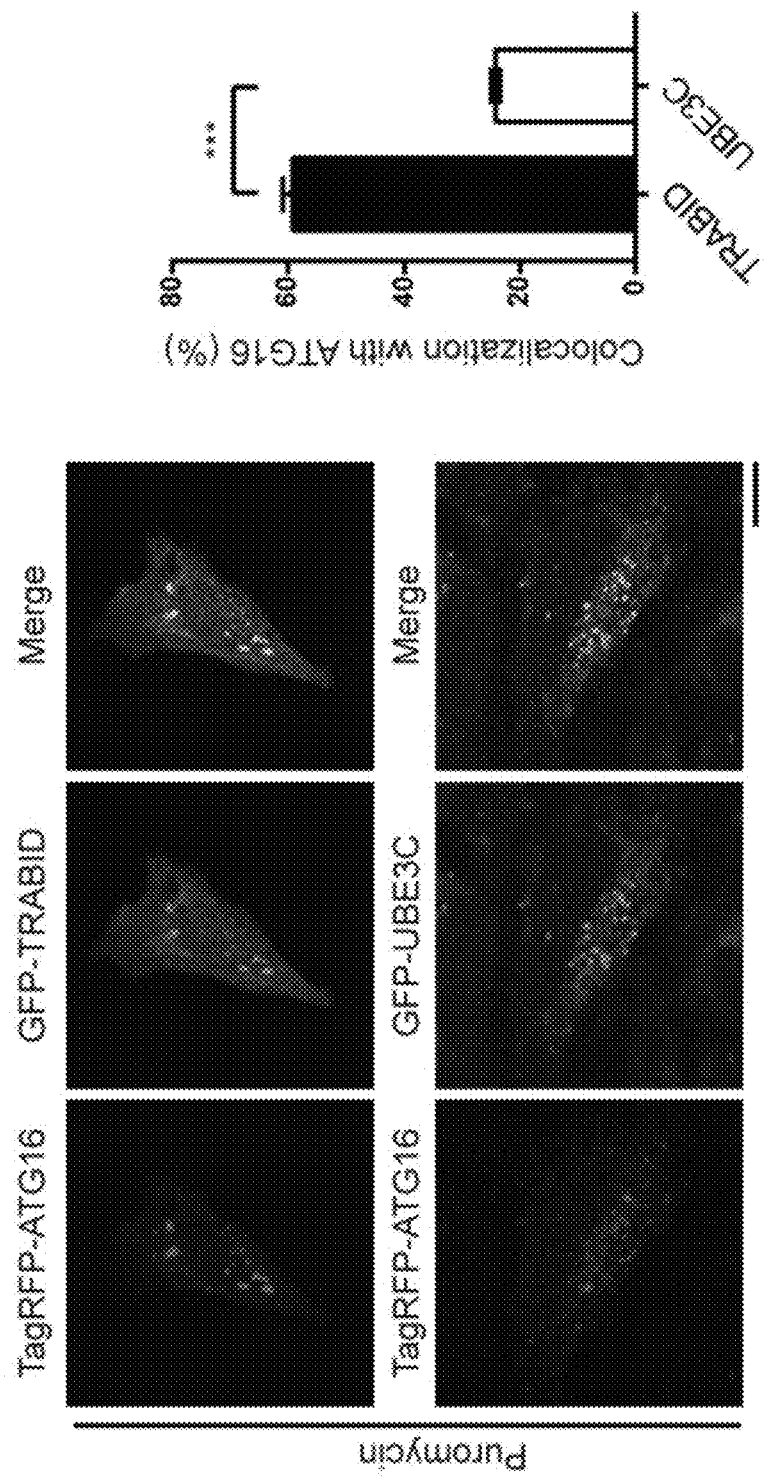

In unstressed or starved cells, both TRABID and UBE3C exhibited a remarkable colocalization with ATG16 puncta, which represent phagophores (FIG. 5G and FIG. 5H, upper panel). Given the localization of VPS34 complex I to phagophore, this finding was consistent with a concerted action of UBE3C and TRABID on VPS34 regulation under these circumstances. However, upon tunicamycin treatment, UBE3C showed a poor colocalization with ATG16 puncta, while TRABID recruitment to phagophores was retained (FIG. 5I). This finding was recapitulated by using three different fluorescent tags to mark UBE3C, TRABID and ATG16 in the same cell (FIG. 5H, lower panel). Furthermore, similar findings were observed from puromycin-treated cells, in which TRABID showed a higher colocalization with ATG16 puncta than UBE3C (FIG. 5J).

Figure 5K:
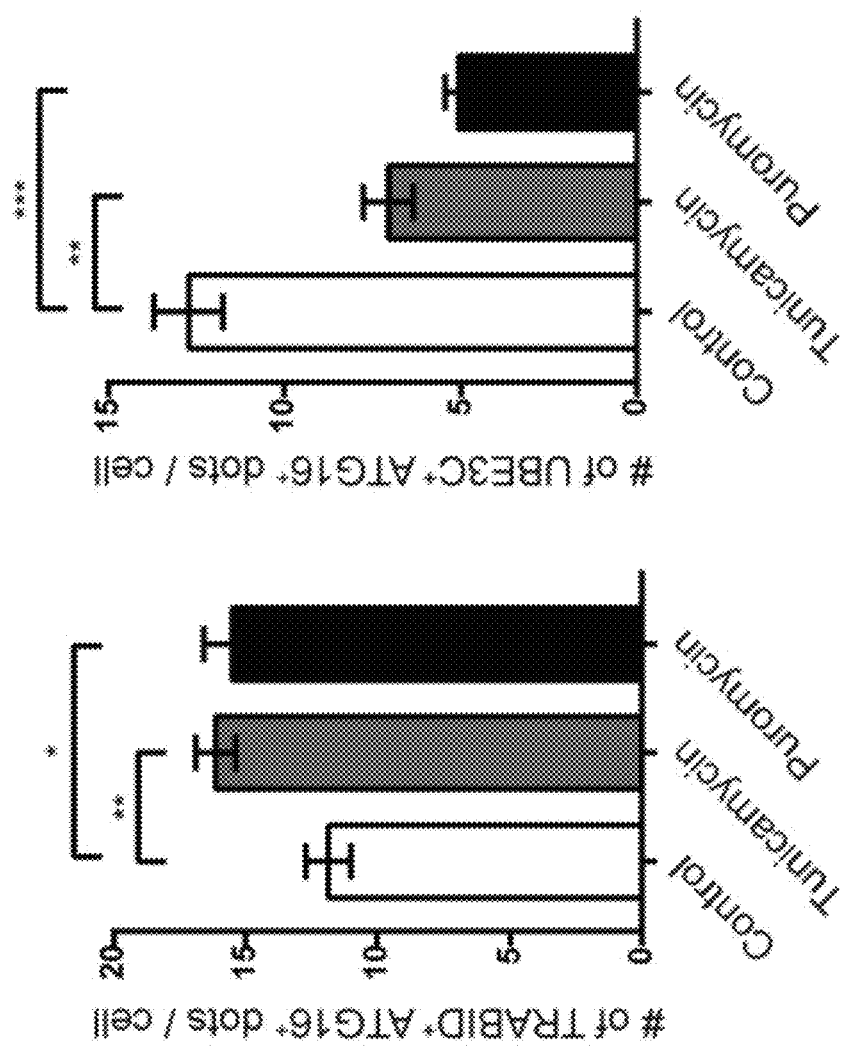
FIG. 5K shows quantitative data for the absolute numbers of GFP-TRABID/TagRFP-ATG16 and GFP-UBE3C/TagRFP-ATG16 double positive dots in cells treated with indicated agents.
Figure 5L:
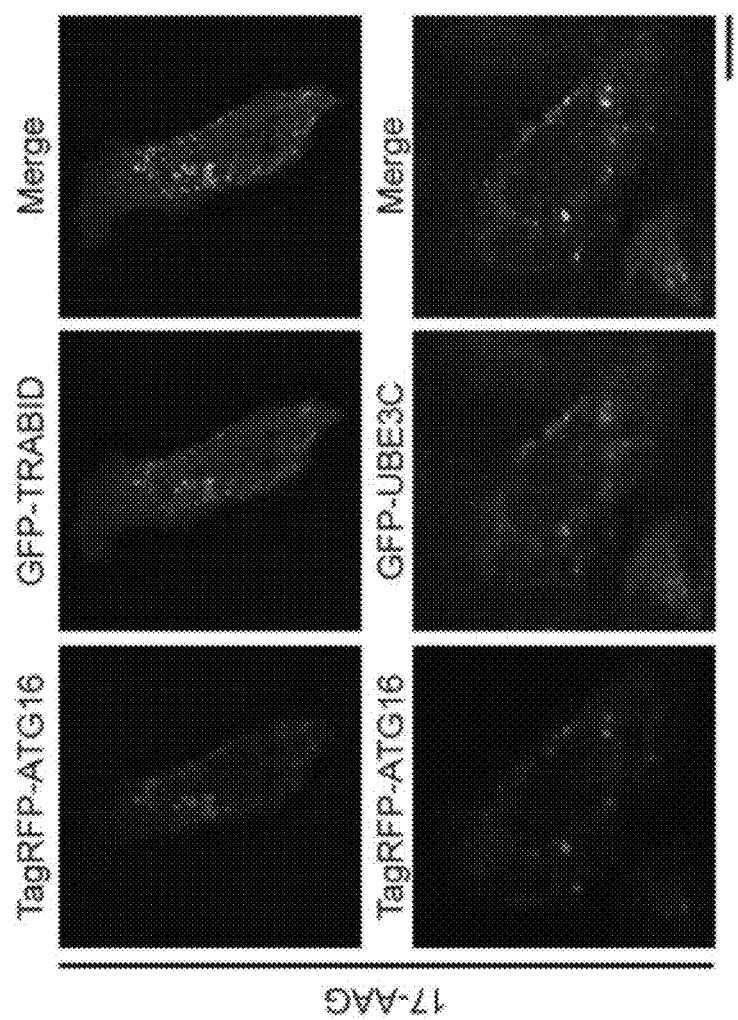
FIGS. 5L and 5M show the results of confocal analysis of the colocalization of TagRFP-ATG16 with GFP-TRABID or GFP-UBE3C in transfected HeLa cells treated with 17-AAG or MG132 for 1 h. Bar: 10 μm.
Figure 5M:
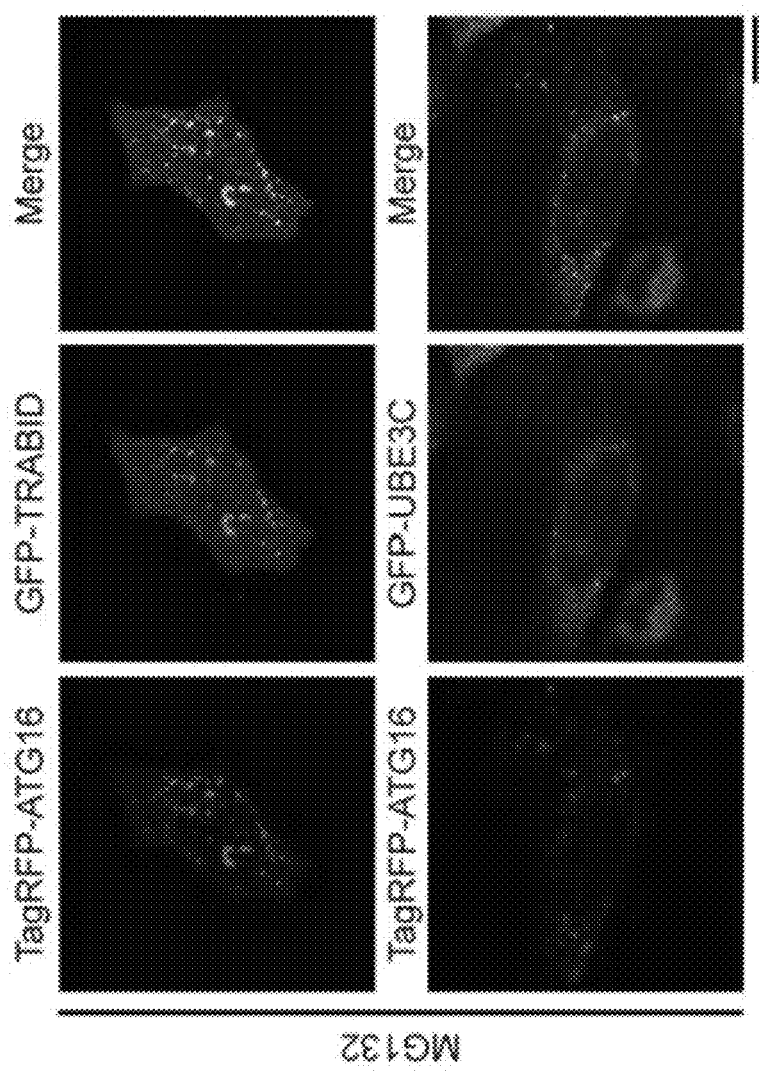

Accordingly, while TRABID/ATG16 double positive puncta were increased in response to tunicamycin or puromycin treatment, UBE3C/ATG16 double positive dots were decreased (FIG. 5K). In cells treated with proteotoxic stressor 17-AAG or MG132, the impairment of phagophore targeting of UBE3C, but not TRABID, was also observed (FIGS. 5L and 5M). Thus, the reduced association of UBE3C with VPS34 under ER and proteotoxic stresses was likely due to a spatial separation of the two proteins.

Figure 5N:
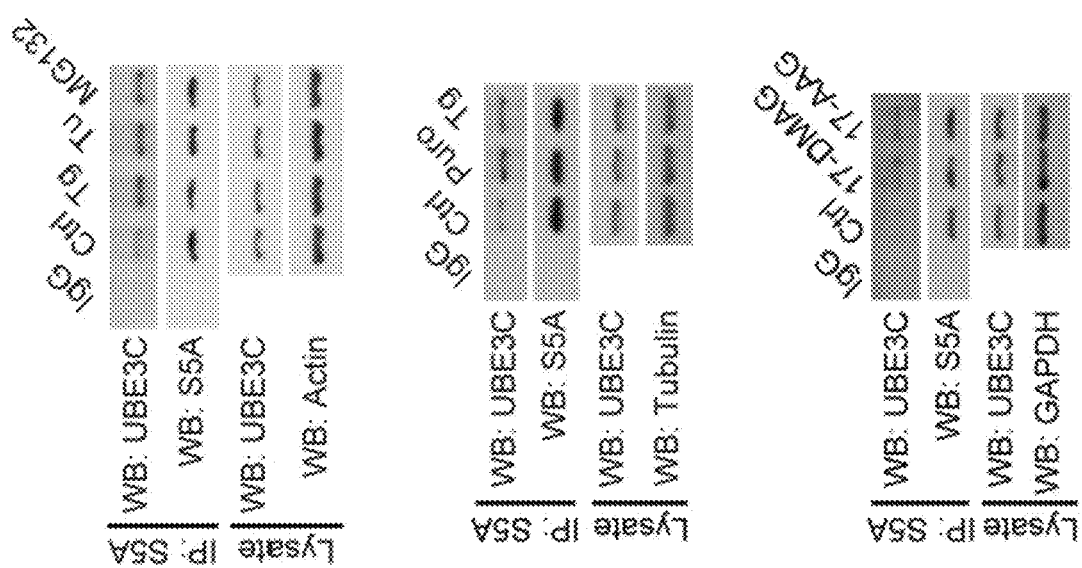

Further, since ER and proteotoxic stresses can increase cellular misfolded and ubiquitinated proteins, their effects on UBE3C association with proteasome was investigated. As shown in FIG. 5N, agents that induce ER or proteotoxic stress all increased the association of UBE3C with proteasome, as detected by co-immunoprecipitation of UBE3C with the proteasome subunit SSA. Together, these findings were consistent with a notion that ER and proteotoxic stresses induced a switch of UBE3C localization from phagophore to proteasome, thereby relieving its inhibitory effect on autophagy.

Example 8: Enforced Targeting of UBE3C to VPS34 Attenuates Autophagy Induction by ER and Proteotoxic Stresses to Compromise ER and Protein Quality Control To substantiate that the reduced association of UBE3C with VPS34 contributes to autophagy induction under ER and proteotoxic stresses and to explore the physiological impacts of this regulation, this regulation was blocked by enforced targeting of UBE3C to VPS34. To this end, a chemically induced dimerization strategy was utilized. Specifically, UBE3C KO cells were transfected with constructs for FKBP12-UBE3C and FRB-VPS34 fusion proteins (termed targeting cells). In the control experiment, cells were transfected with FKBP12-UBE3C and VPS34 (without fusion with FRB; termed control cells).

Figures 6A, 6B:
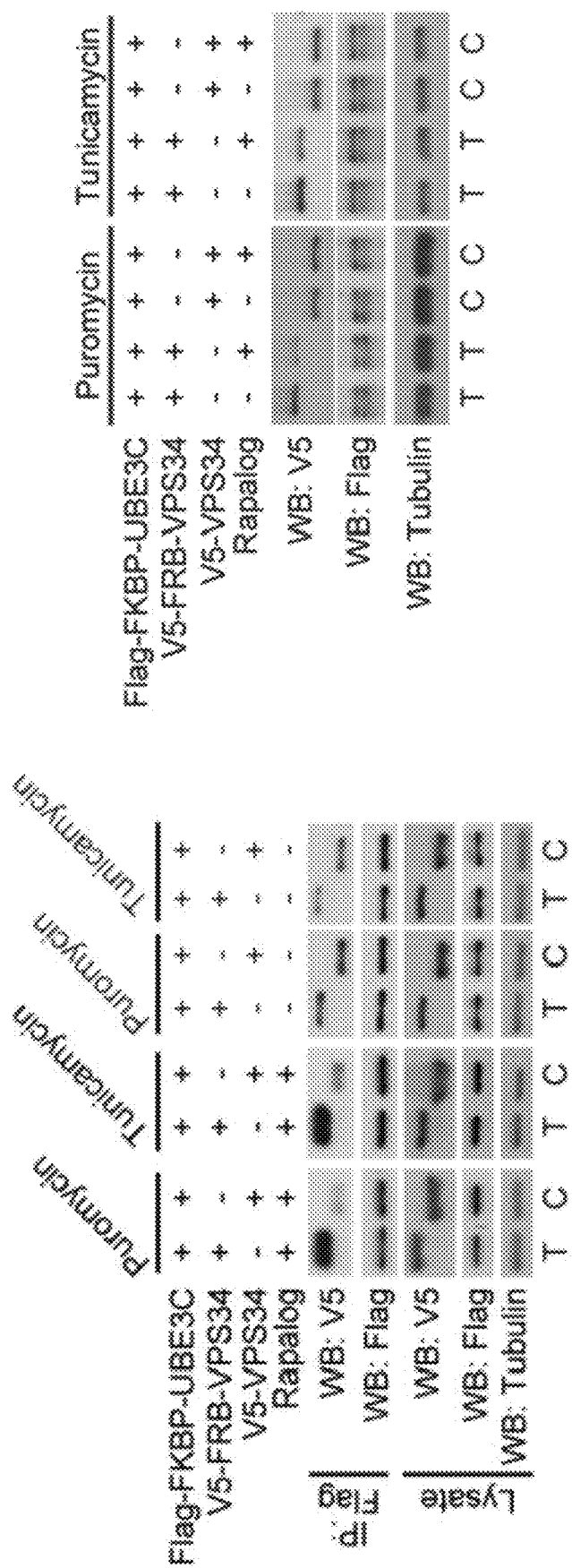
FIGS. 6A to 6J are graphs illustrating that enforced binding of UBE3C to VPS34 under ER or proteotoxic stress compromises proteostasis and ER quality control.

As shown in FIG. 6A, when the targeting and control cells were treated with rapalog together with tunicamycin or puromycin, a stronger interaction between transfected UBE3C and VPS34 was observed in the targeting than control cells, and these differences were not seen in cells without rapalog treatment. Accordingly, rapalog treatment reduced VPS34 steady-state level in puromycin or tunicamycin-treated targeting cells but not in control cells (FIG. 6B). Thus, a system that can reverse the impairment of UBE3C targeting to VPS34 during ER and proteotoxic stresses was established.

Figure 6C:
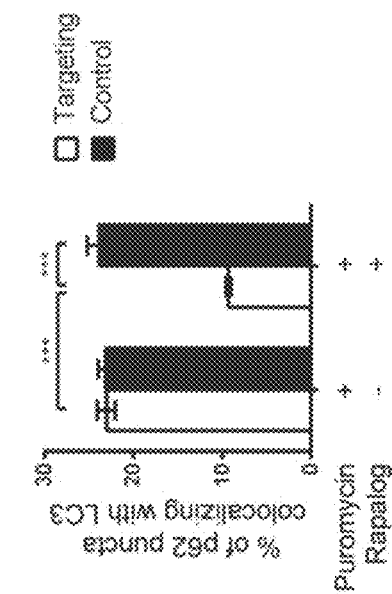
Figure 6C:
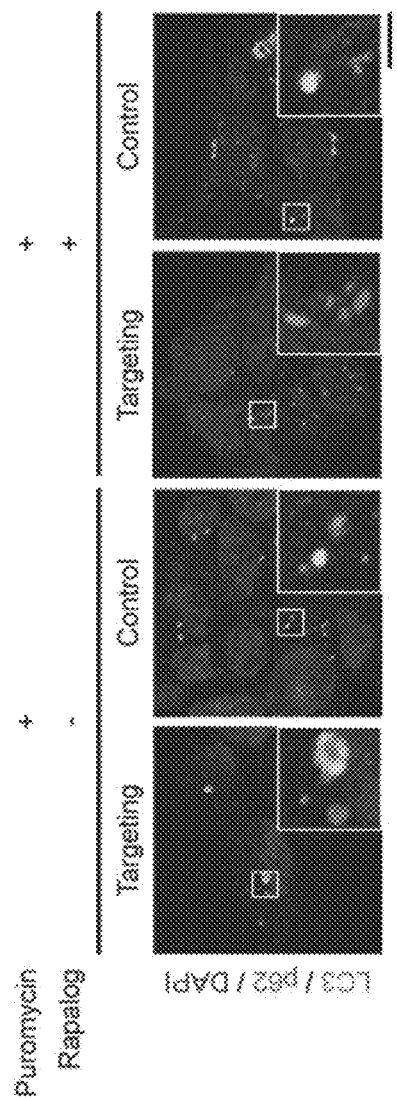
Figure 6D:
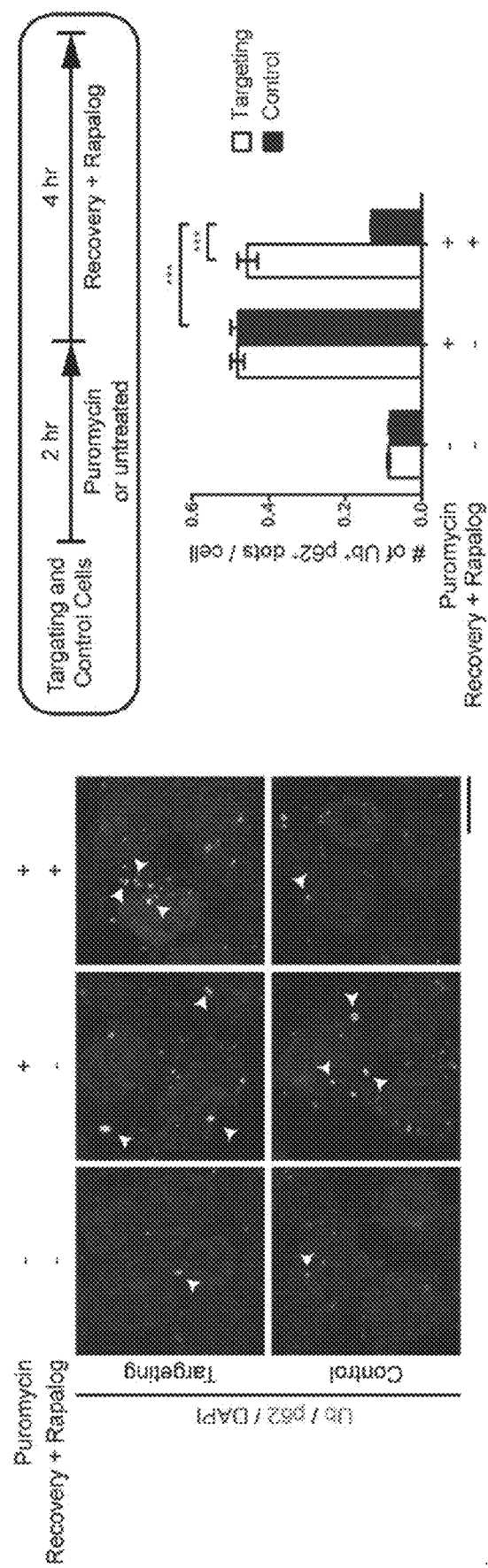
Figure 6E:
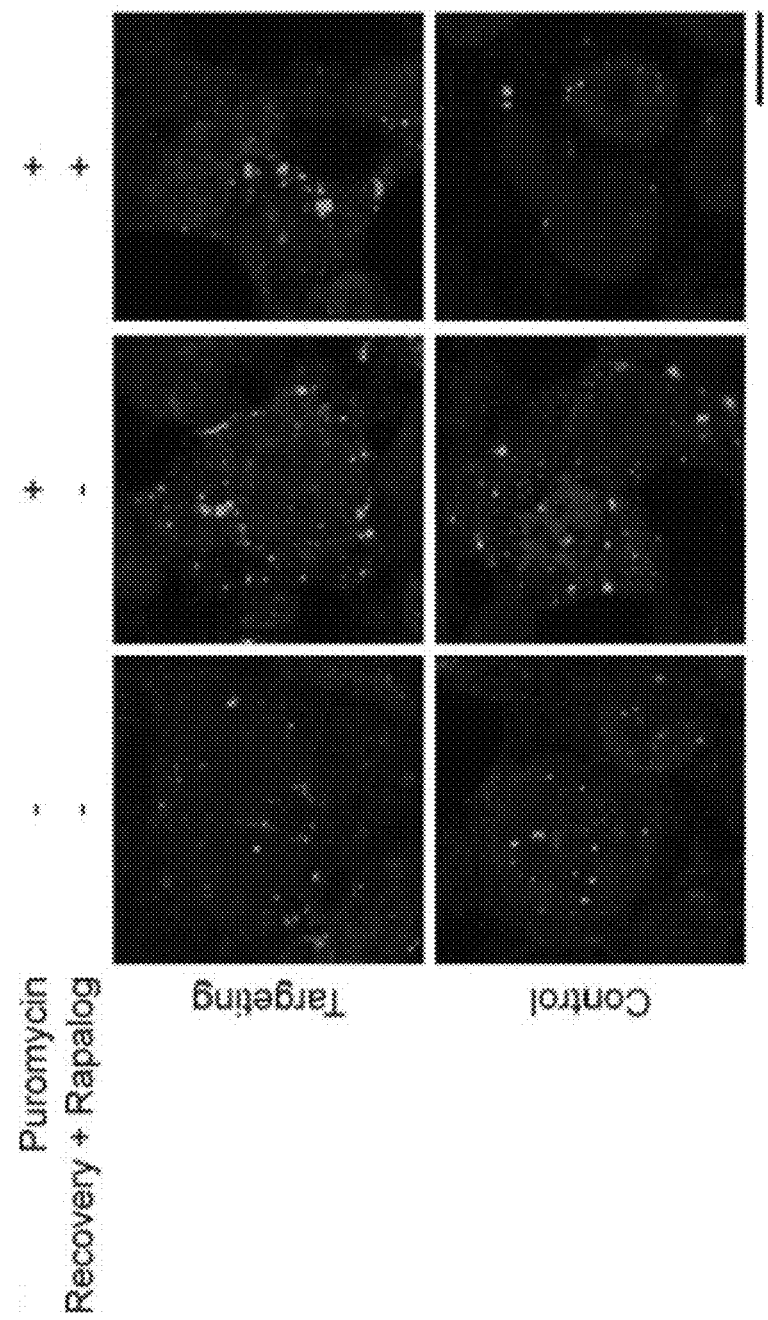
Figure 6F:
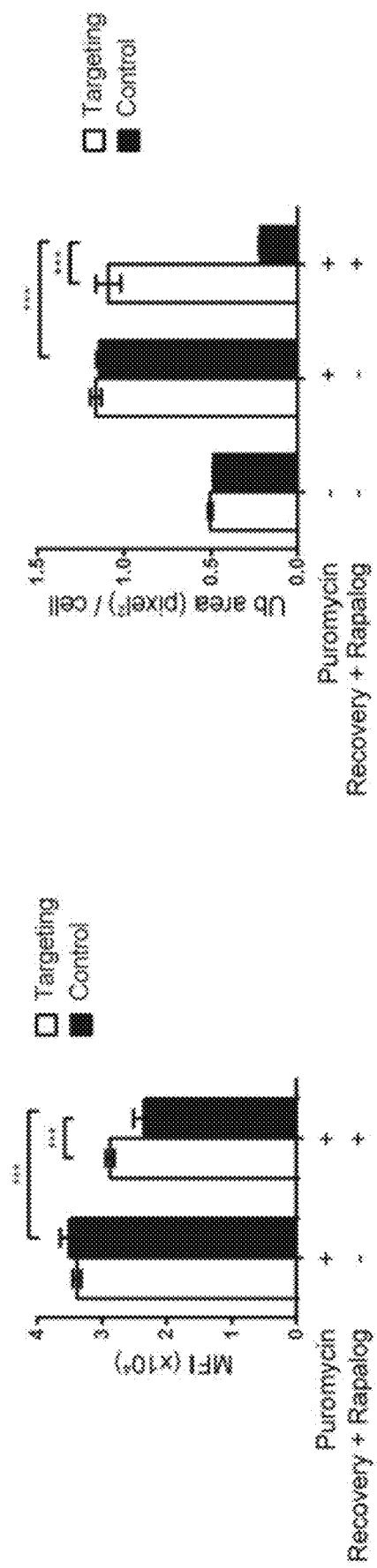

Next, such system was utilized to assess the impacts of ER/proteotoxic stress-induced UBE3C relocation on autophagy activity and cell homeostasis. First, aggrephagy activity in targeting and control cells treated with puromycin was evaluated. As shown in FIG. 6C, rapalog induced a reduction in the co-localization of p62 (a ubiquitin-binding autophagy receptor) puncta with LC3 puncta in puromycin-treated targeting cells but not control cells, indicating that enforced targeting of UBE3C to VPS34 diminished aggrephagy activity. To evaluate the impact of this decreased aggrephagy activity on the clearance of ALIS (aggresome-like induced structure), targeting and control cells were treated with puromycin, followed by washing out puromycin, and then inducing UBE3C/VPS34 interaction by rapalog during the recovery phase (FIG. 6D, upper right panel). Remarkably, while control cells showed a significant decrease of ubiquitin positive aggregates and ubiquitin/p62 double positive aggregates after 4 h of recovery from puromycin treatment, ALIS clearance was impaired in the targeting cells (FIGS. 6D and 6E). A similar finding was observed by using PROTEOSTAT dye for detecting cellular protein aggregates (FIG. 6F). Thus, enforced targeting of UBE3C to VPS34 impairs the clearance of puromycin-induced protein aggregates via selective autophagy.

Figure 6G:
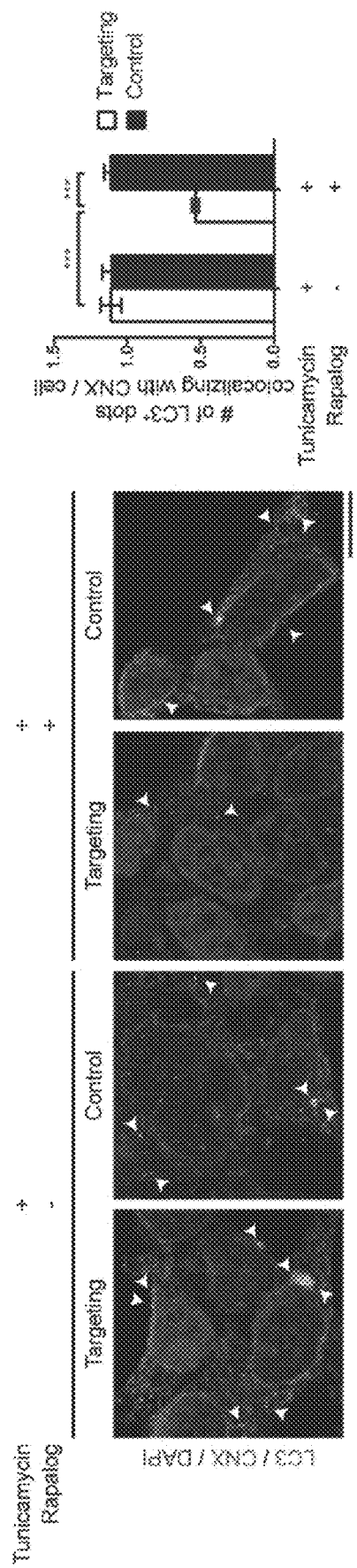
Figure 6H:
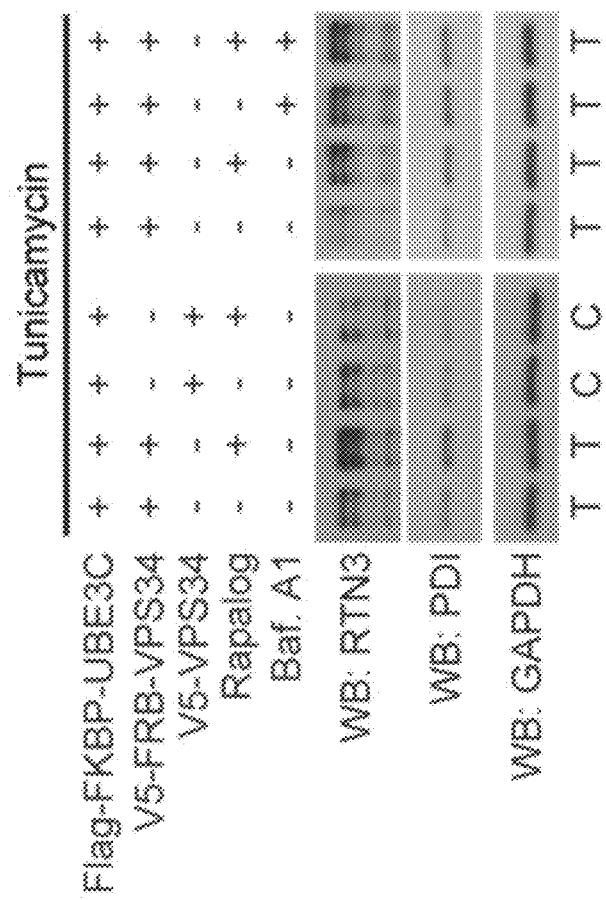

In addition to inducing protein aggregates, ER stress could also stimulate ER-phagy through ubiquitin-dependent and independent mechanisms; therefore, the impact of ER stress-induced dissociation of UBE3C from VPS34 on ER-phagy was determined. FIG. 6G showed that enforced targeting of UBE3C to VPS34 in tunicamycin-treated cells led to a reduced co-localization of LC3 puncta with ER marker, calnexin. This was accompanied with a decreased lysosomal degradation of ER-resident proteins, RTN3 and PDI (FIG. 6H).

Figure 6J:
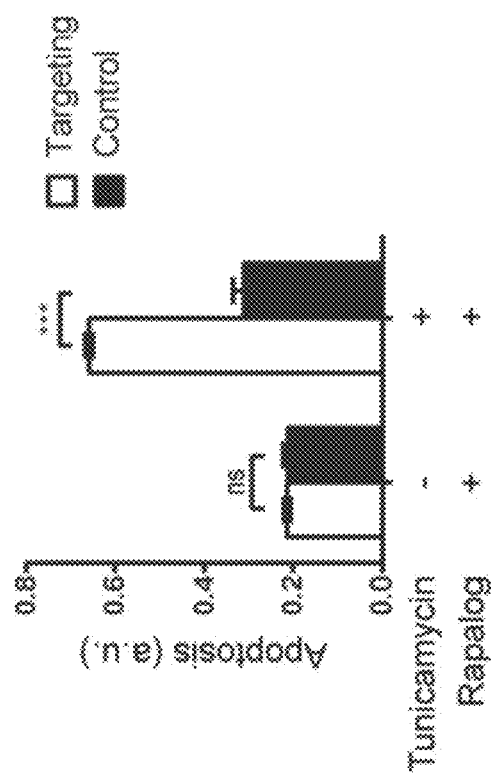
Figure 6I:
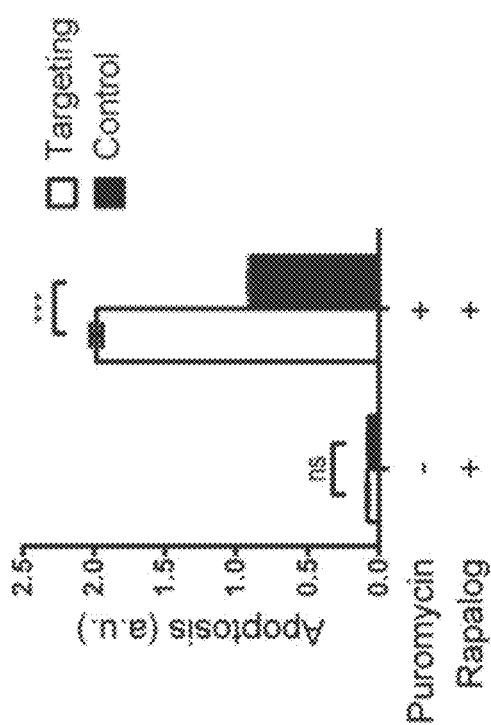

All these observations indicated an impairment of ER-phagy. Upon rapalog treatment, the targeting cells were more susceptible to puromycin- or tunicamycin-induced apoptosis than the control cells, but their responses to these ER/proteotoxic stressors were comparable in the absence of rapalog (FIGS. 6I and 6J). Together, such data supported an idea that ER/proteotoxic stress-induced dissociation of UBE3C from VPS34 facilitates the induction of selective autophagy for protein and ER quality control, thereby maintaining cell survival.

Example 9: Dysregulation of TRABID/VPS34 Axis Contributes to Liver Steatosis

Figure 7A:
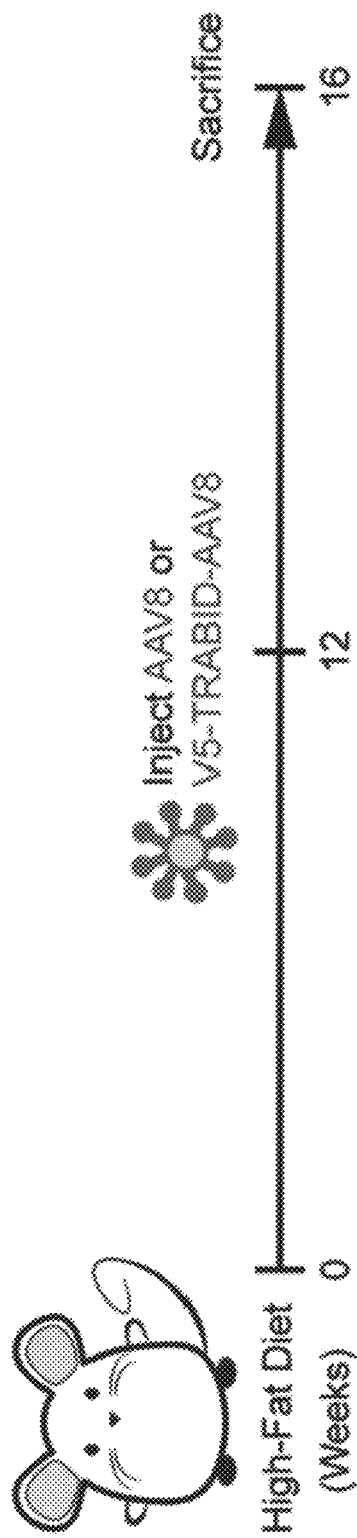

To interrogate the in vivo function of TRABID-mediated VPS34 stabilization in liver metabolism, a mouse model of NAFLD was established by feeding mice with a high-fat diet (HFD). After 12 weeks of feeding, the mice were retro-orbitally injected with recombinant adeno-associated virus (rAAV) expressing TRABID or vector control and sacrificed at 4 weeks later (FIG. 7A).

Figure 7B:
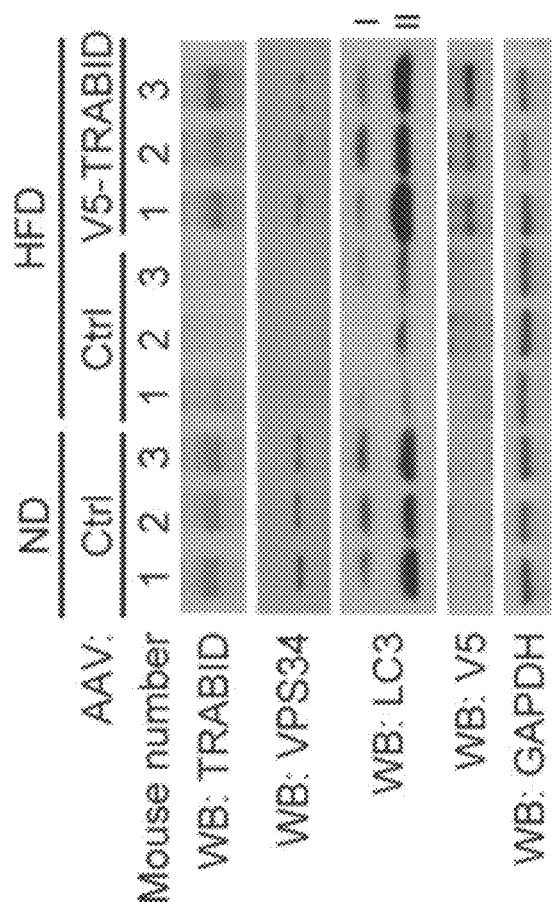
Figure 7C:
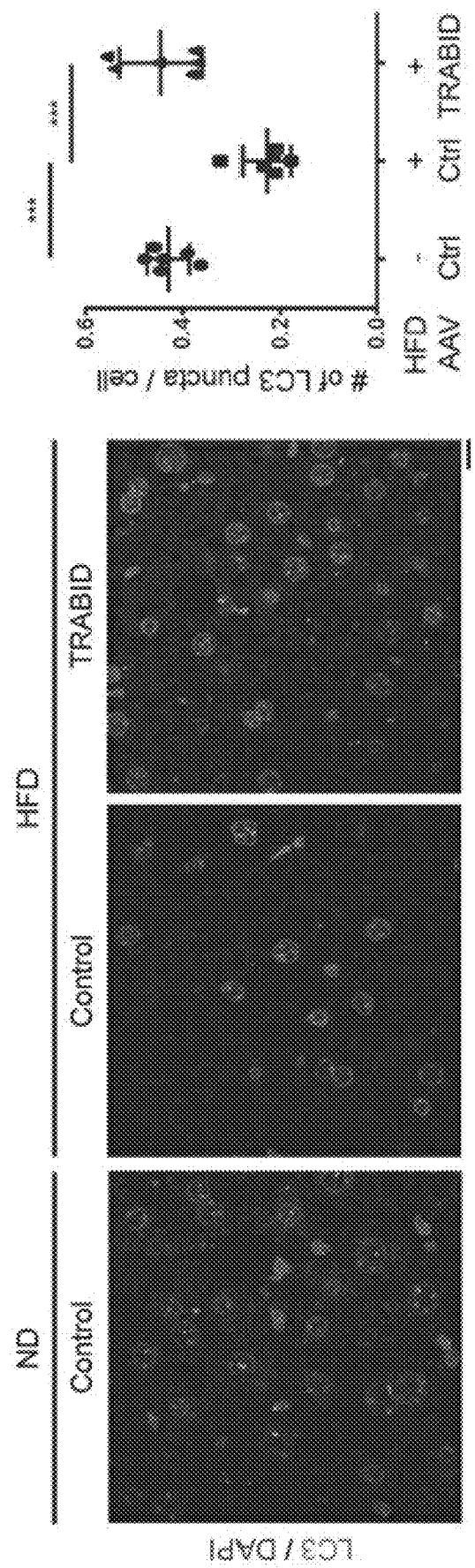
Figure 7D:
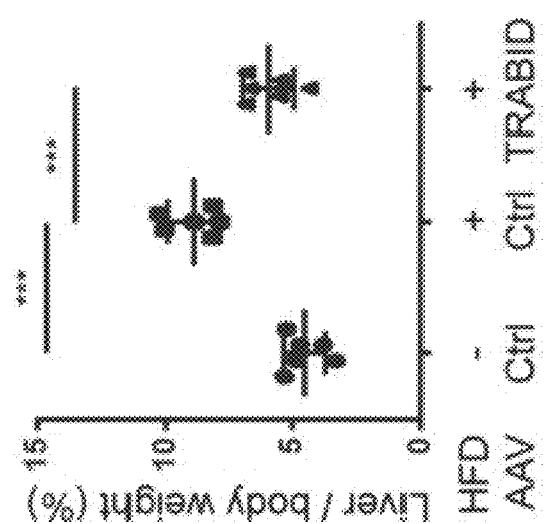
Figure 7E:
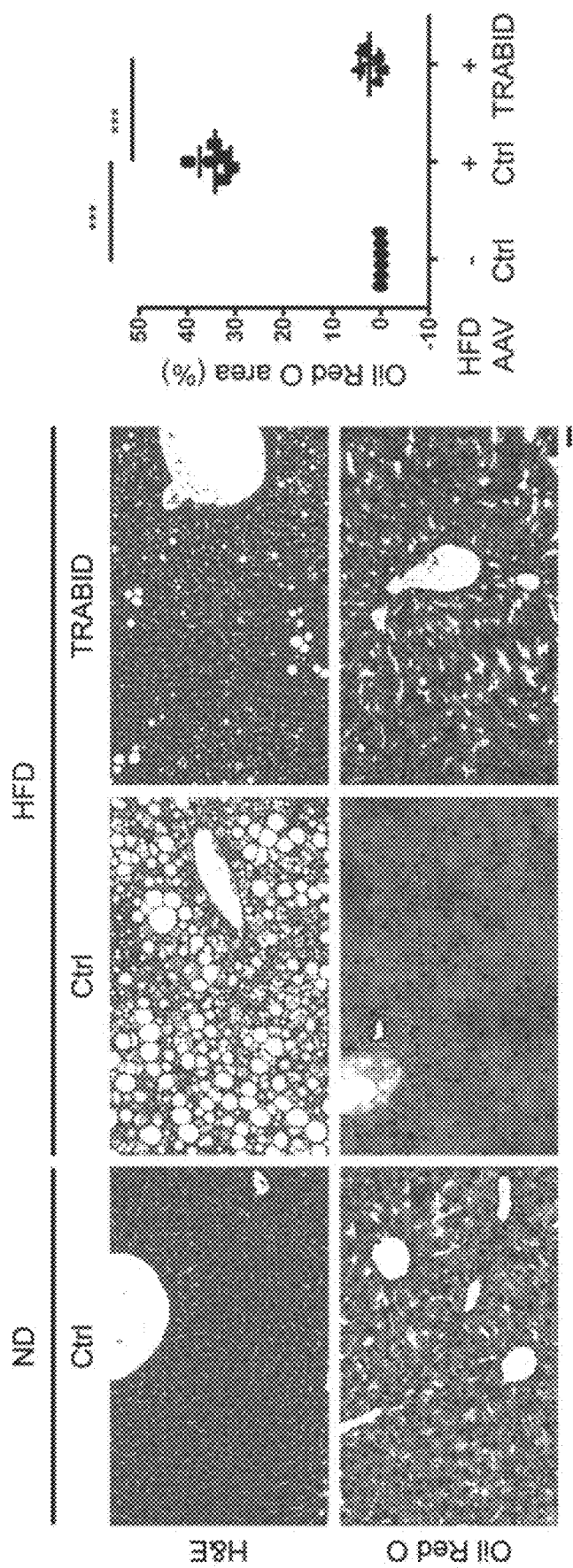
Figure 7G:
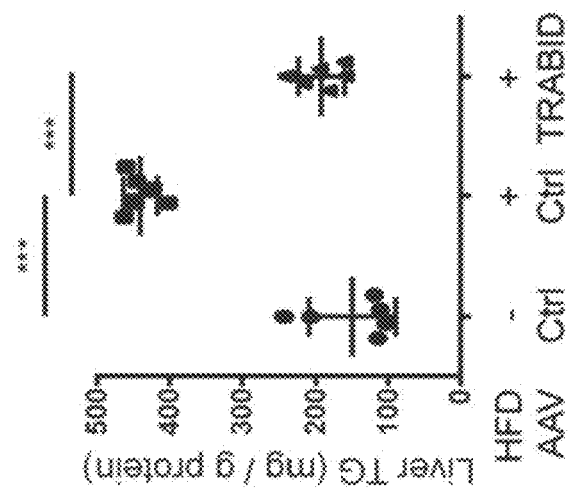
Figure 7F:
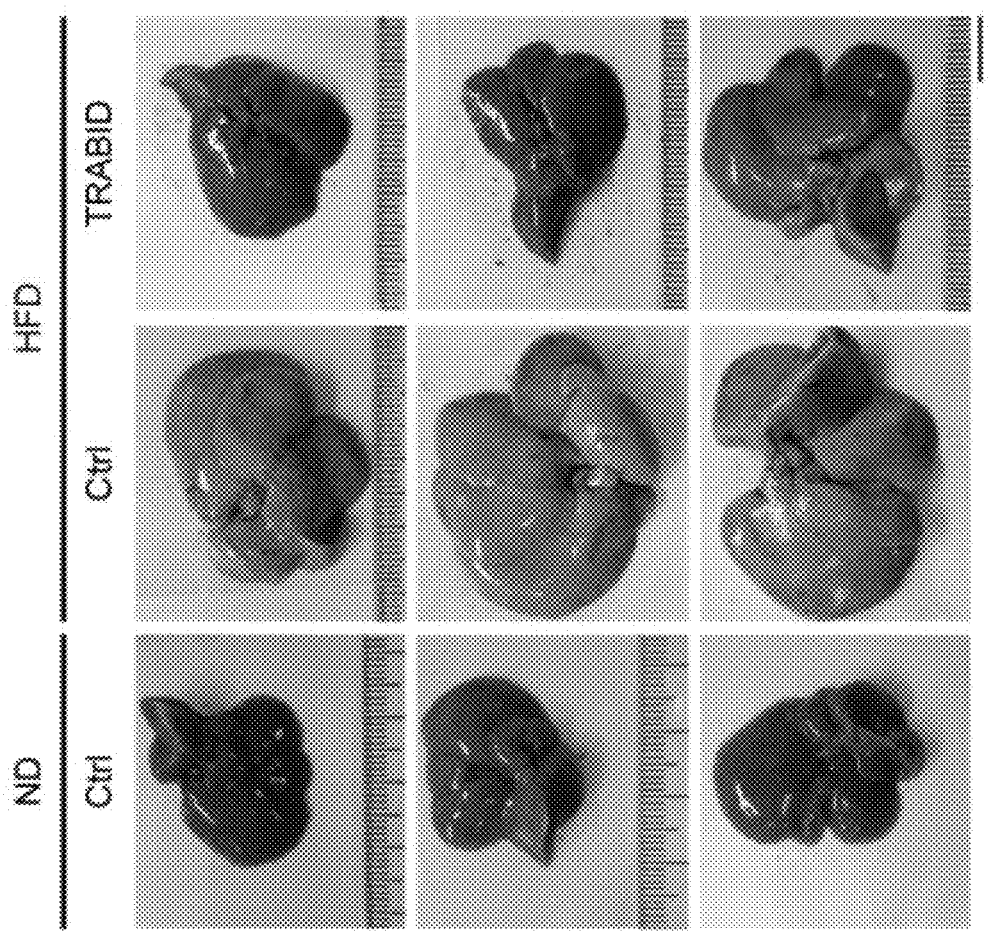
Figure 7H:
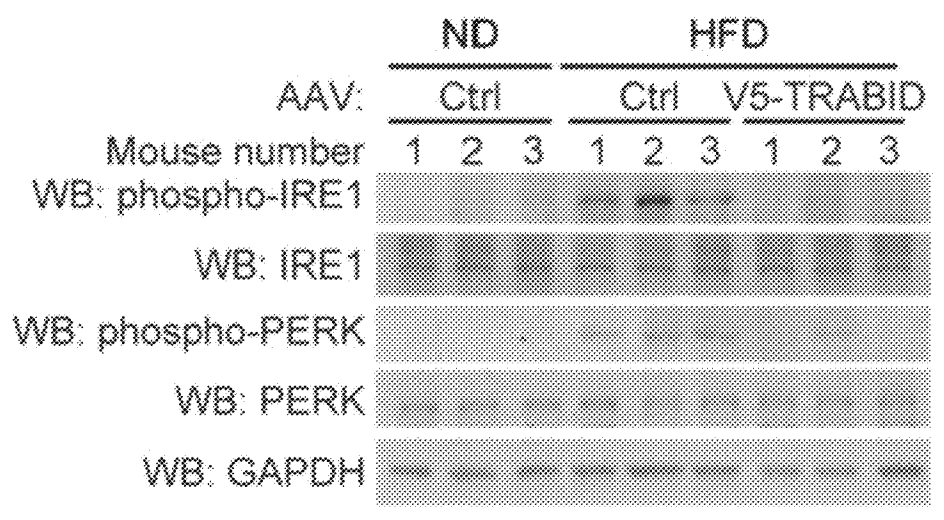
Figure 7J:
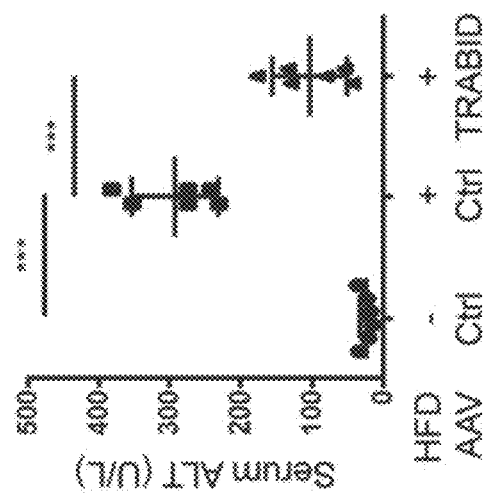
Figure 7I:
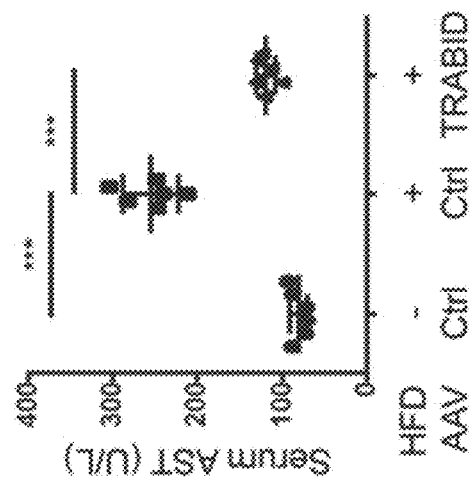

As shown in FIGS. 7B and 7C, HFD decreased liver autophagy activity, as demonstrated by reduced LC3 lipidation and LC3 puncta. These changes were associated with the downregulation of both VPS34 and TRABID (FIG. 7B), suggesting that impairment of TRABID-mediated VPS34 stabilization contributes to NAFLD. In line with this notion, four-week treatment of rAAV-TRABID not only restored VPS34 expression and autophagy activity, but greatly alleviated HFD-induced increase of liver/body weight (FIG. 7D) and lipid accumulation in the liver, which was evident by gross anatomical view of the livers as well as H&E staining and Oil Red O staining of the liver sections (FIGS. 7E and 7F). The HFD-induced increase of hepatic triglyceride content was also reversed by rAAV-TRABID (FIG. 7G). Furthermore, administration of rAAV-TRABID attenuated HFD-induced ER stress, as measured by p-IRE1 and p-PERK levels in the liver and mitigated liver damage, as monitored by alanine aminotransferase (ALT) and aspartate aminotransferase (AST) activities in the serum (FIGS. 7H to 7J). It thus can be seen that administration of rAAV-TRABID alleviates the progression of NAFLD, suggesting a potential of role of TRABID overexpression or activation in NAFLD therapy.

These results highlight the observation of TRABID-mediated VPS34 stabilization in maintaining normal liver metabolism and uncover the contribution of TRABID downregulation to the pathogenesis of liver steatosis through VPS34 destabilization and autophagy deficiency.

Example 10: rAAV-TRABID Decreased the Visceral Fat Content Induced by HFD

Figure 8:
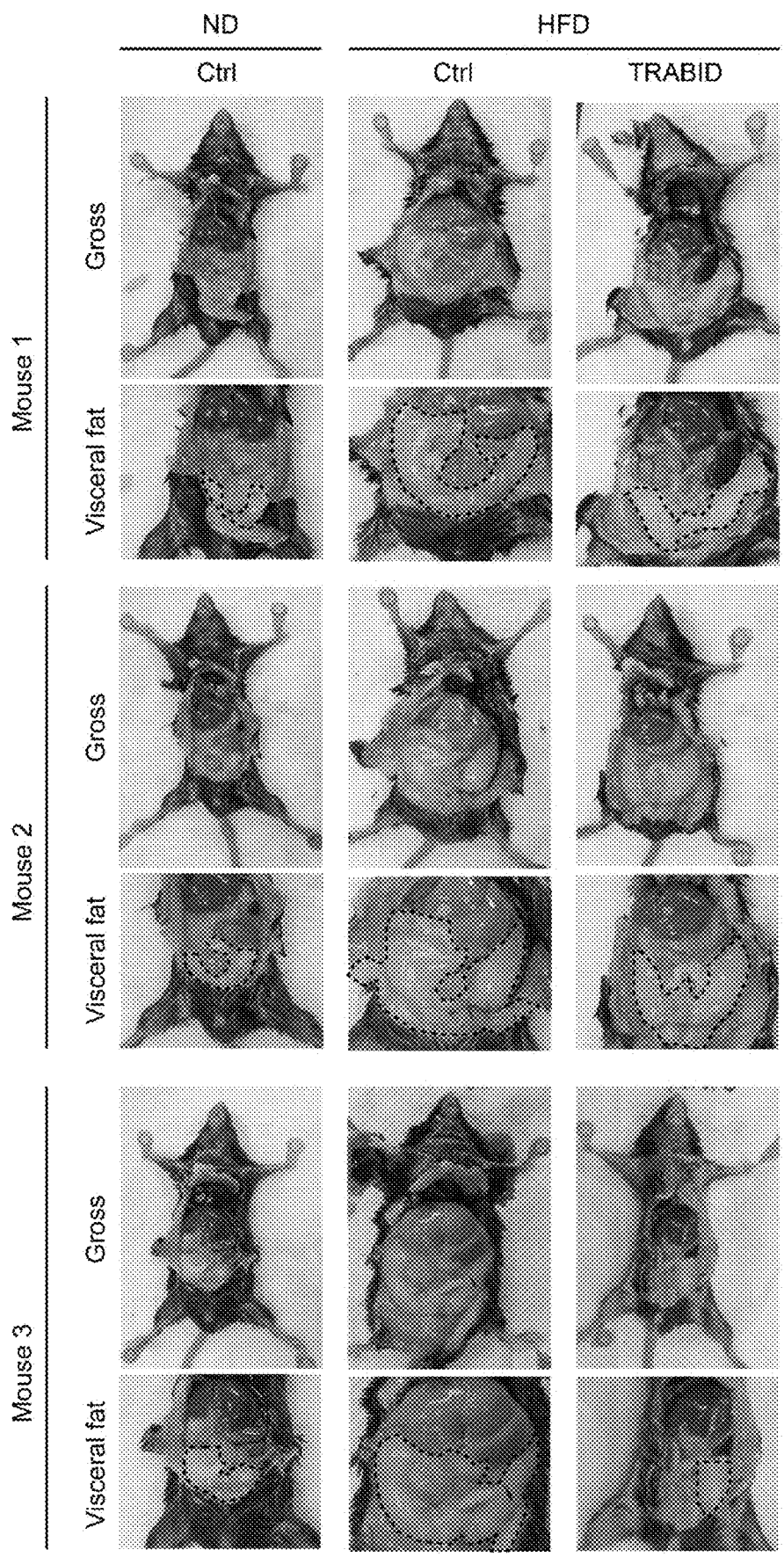
FIG. 8 shows pictures illustrating that TRABID treatment reduces the visceral fat content induced by high fat diet (HFD).

In addition to mitigating NAFLD-related phenotypes in mice fed with HFD, the rAAV-TRABID administration also decreased visceral fat content. As shown in FIG. 8, visceral fat (marked by dashed lines) in the abdominal region of mice was significantly elevated by HFD feeding, and this was partially reversed by treatment of mice with rAAV-TRABID.

These results suggest that the effect of TRABID on lipid metabolism can extend beyond the liver to reach to a whole-body level. Thus, increasing TRABID expression would offer a promise in preventing or treating obesity-related disorders.

From the above, the experiments indicate that the switch of UBE3C localization from phagophore to proteasome plays a role for cells to cope with the stressed conditions by favoring TRABID-mediated VPS34 stabilization and autophagy induction, as prevention of this switch by an enforced association of UBE3C with VPS34 impairs autophagy induction and compromises proteostasis, ER quality control and cell survival. In the liver, TRABID-mediated VPS34 stabilization affects lipid metabolism and is downregulated in a mouse model of NAFLD. Thus, VPS34 K29/K48 branched ubiquitination can be positively or negatively regulated from the axis of UBE3C or TRABID under different physiological or pathological conditions, thereby inhibiting or stimulating autophagy activity to impact on cell and tissue homeostasis.

The present disclosure unexpectedly provides a previously unappreciated K29/K48 branched ubiquitination on the autophagy regulator VPS34, identifies the enzymes UBE3C and TRABID to reciprocally control this ubiquitination, elucidates the enhanced proteasomal degradation fate of this ubiquitination and reveals the impacts of this ubiquitination on ER and protein quality control and liver metabolism. Hence, the present disclosure provides an effective strategy for metabolic disorders such as obesity or fatty liver disease, which is useful in improving autophagy deficiency and lipid metabolism, so as to control the fat accumulation.

While some of the embodiments of the present disclosure have been described in detail above, it is, however, possible for those of ordinary skill in the art to make various modifications and changes to the embodiments shown without substantially departing from the teaching and advantages of the present disclosure. Such modifications and changes are encompassed in the scope of the present disclosure as set forth in the appended claims.

REFERENCE

[1] Liu, C. C. et al. Cul3-KLHL20 ubiquitin ligase governs the turnover of ULK1 and VPS34 complexes to control autophagy termination. *Mol. Cell.* 61, 84-97 (2016).
[2] Yuan, W. C. et al. K33-linked polyubiquitination of coronin 7 by Cul3-KLHL20 ubiquitin E3 ligase regulates protein trafficking. *Mol. Cell.* 54, 586-600 (2014).
[3] Swatek, K. N. et al. Insights into ubiquitin chain architecture using Ub-clipping. *Nature* 572, 533-537 (2019).
[4] Wang, M. & Pickart, C. M. Different HECT domain ubiquitin ligases employ distinct mechanisms of polyubiquitin chain synthesis. *EMBO J.* 24, 4324-4333 (2005).
[5] Yau, R. & Rape, M. The increasing complexity of the ubiquitin code. *Nat. Cell Biol.* 18, 579-586 (2016).
[6] Meyer, H. J. & Rape, M. Enhanced protein degradation by branched ubiquitin chains. *Cell* 157, 910-921 (2014).

What is claimed is:

1. A method for treating a fatty liver disease in a subject in need thereof, comprising administering to the subject a therapeutically effective amount of a viral vector comprising a nucleic acid encoding tumor-necrosis factor receptor-associated factor (TRAF)-binding protein domain (TRABID) protein.

2. The method according to claim 1, wherein the TRABID protein comprises the amino acid sequence of SEQ ID NO:1 or SEQ ID NO:3.

3. The method according to claim 1, wherein the nucleic acid encoding the TRABID protein comprises the nucleic acid sequence of SEQ ID NO:2 or SEQ ID NO:4.

4. The method according to claim 1, wherein the fatty liver disease is selected from the group consisting of non-alcoholic fatty liver disease (NAFLD), alcoholic fatty liver disease, alcoholic steatohepatitis, non-alcoholic steatohepatitis (NASH), and liver steatosis.

5. The method according to claim 1, further comprising administering at least one additional therapy for the fatty liver disease to the subject, wherein the additional therapy is selected from the group consisting of insulin, an insulin analog, an α-glucosidase inhibitor, a glucagon-like peptide-1 (GLP-1) analog, a sodium glucose transporter-2 (SGLT2) inhibitor, sulfonylurea, meglitinide, and thiazolidinedione.

6. The method according to claim 1, wherein the administration is administering to the subject a recombinant adeno-associated virus (rAAV) viral vector comprising the nucleic acid encoding the TRABID protein or the functional variant thereof.

7. The method according to claim 6, wherein the viral vector further comprises an AAV8 capsid.

8. A method for reducing excessive fat in the liver of a subject in need thereof, comprising administering to the subject a therapeutically effective amount of a viral vector comprising a nucleic acid encoding tumor-necrosis factor receptor-associated factor (TRAF)-binding protein domain (TRABID) protein.

9. The method according to claim 8, wherein the method reduces body fat accumulation in the subject, reduces excessive fat in the liver of the subject, reduces the weight of the subject, or any combination thereof.

10. The method according to claim 8, wherein the TRABID protein comprises the amino acid sequence of SEQ ID NO:1 or SEQ ID NO:3.

11. The method according to claim 8, wherein the nucleic acid encoding the TRABID protein comprises the nucleic acid sequence of SEQ ID NO:2 or SEQ ID NO:4.

12. The method according to claim 8, wherein the administration is administering to the subject a recombinant adeno-associated virus (rAAV) viral vector comprising the nucleic acid encoding the TRABID protein.

13. The method according to claim 8, wherein the administration promotes at least one of autophagy activity or lipid metabolism in the subject.

14. The method according to claim 8, wherein the administration reduces a serum level of at least one of alanine aminotransferase (ALT) or aspartate aminotransferase (AST) in the subject.

15. The method according to claim 8, wherein the subject is a mammal.

16. The method according to claim 15, wherein the mammal is selected from the group consisting of a rodent, a mouse, a monkey, a guinea pig, a dog, a cat, cow, a sheep, a pig, a horse, a rabbit, and a human.

* * * * *